United States Patent [19]

Nagase et al.

[11] Patent Number: 5,714,483
[45] Date of Patent: Feb. 3, 1998

[54] ANTITUSSIVE

[75] Inventors: Hiroshi Nagase, Kamakura; Junzo Kamei, Tokyo; Koji Kawai, Kamakura; Takashi Endo, Chigasaki, all of Japan

[73] Assignee: TORAY Industries, Inc., Tokyo, Japan

[21] Appl. No.: 290,837

[22] PCT Filed: Dec. 22, 1993

[86] PCT No.: PCT/JP93/01855

§ 371 Date: Oct. 13, 1994

§ 102(e) Date: Oct. 13, 1994

[87] PCT Pub. No.: WO94/14445

PCT Pub. Date: Jul. 7, 1994

[30] Foreign Application Priority Data

Dec. 22, 1992 [JP] Japan ................... 4-341947

[51] Int. Cl.$^6$ ......................................... A61K 31/535
[52] U.S. Cl. ................................................ 514/229.5
[58] Field of Search ....................................... 514/229.5

[56] References Cited

U.S. PATENT DOCUMENTS

| | | |
|---|---|---|
| 4,816,586 | 3/1989 | Portoghese . |
| 5,332,818 | 7/1994 | Nagase et al. . |

FOREIGN PATENT DOCUMENTS

| | | |
|---|---|---|
| 76319 | 11/1992 | Australia . |
| 0155424 | 12/1984 | European Pat. Off. . |
| 0456833 | 11/1991 | European Pat. Off. . |
| 4-342529 | 11/1992 | Japan . |
| WO-A9107966 | 6/1991 | WIPO . |

OTHER PUBLICATIONS

Eur. J. Pharmacol., vol. 249, No. 2, J. Kamei et al., "Antitussive effects of naltrindole, . . . "; 1993: 161–165.
Eur. J. Pharmacol., vol. 218, No. 1, P. Portoghese et al., "A highly selective $\delta_1$–opioid receptor antagonist: . . . "; 1992: 195–196.
J. Med. Chem., vol. 34, No. 5, P. Portoghese et al., "Role of Spacer . . . " 1991: 1715–1720.
J. Med. Chem., vol. 33, No. 6, P. Portoghese et al., "Design of Peptidomimetic . . . " 1990: 1714–1720.
CA 117:83213 1992.

*Primary Examiner*—Paul J. Killos
*Attorney, Agent, or Firm*—Birch, Stewart, Kolasch & Birch, LLP

[57] ABSTRACT

An antitussive having high activity, which is free from side effects such as psychotomimetic, which may also be administered orally is disclosed. The antitussive according to the present invention comprises as an effective ingredient a δ-opioid antagonist or a pharmaceutically acceptable salt thereof.

11 Claims, 2 Drawing Sheets

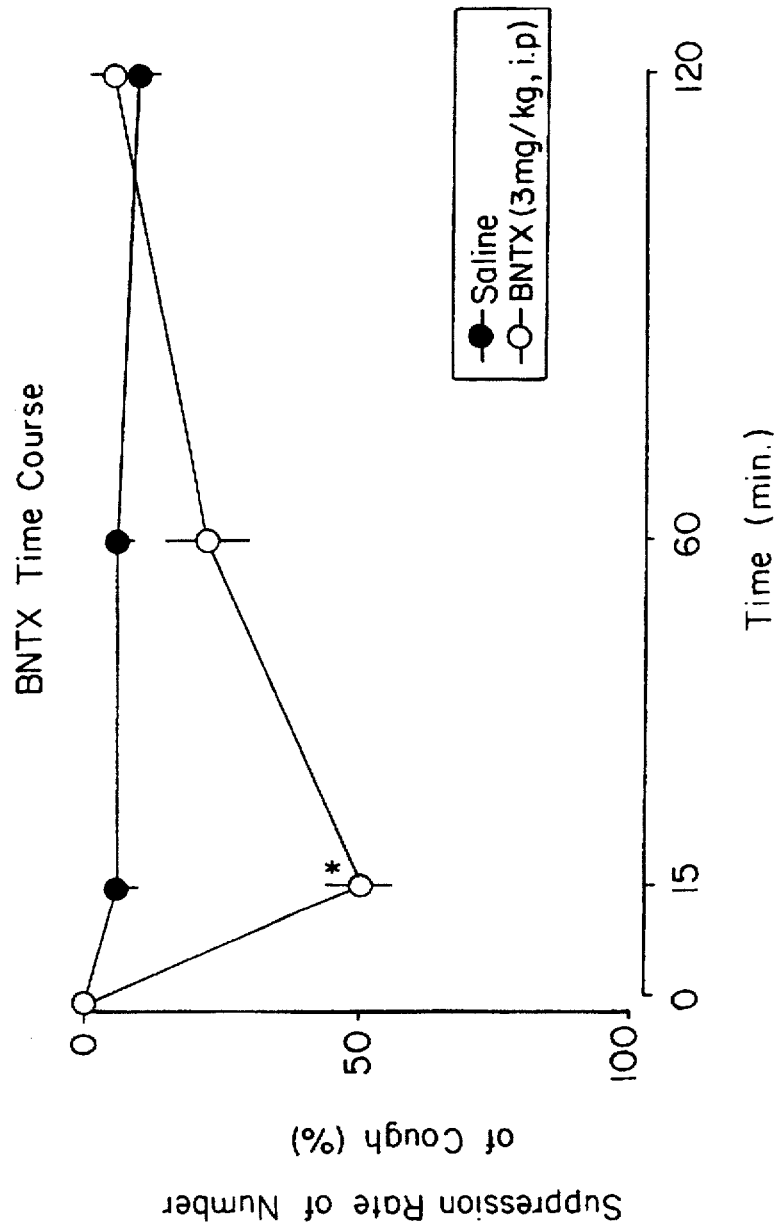

ANTITUSSIVE

TECHNICAL FIELD

The present invention relates to an antitussive.

BACKGROUND ART

Conventional antitussives are provided by mixing drugs which variously affect central nervous system, such as codeine and dextromethorphan. However, these drugs have serious side effects such as drug dependence and psychotomimetic, so that close attention should be paid when using these antitussives.

In recent years, antitissive effect of μ and κ agonists of opioid is drawing attention. However, conventional agonists such as morphine and codeine have problems that they cause drug dependence and conventional κ-agonists have problems that they cause aversion and psychotomimetic. Under these circumstances, an excellent antitussive free from psychotomimetic, drug dependence and aversion is demanded.

DISCLOSURE OF THE INVENTION

An object of the present invention is to provide a novel antitussive having high activity, of which action mechanism is different from that of the above-mentioned conventional antitussives having serious side effects such as drug dependence, psychotomimetic and aversion, which is free from the side effects that the conventional antitussives have, and which may also be used as an oral drug.

The present inventors intensively studied to develop the above-mentioned ideal antitussive to discover that antagonists of δ opioid receptor have strong antitussive effect, which have an action mechanism totally different from that of the conventional morphine, codeine and dextromethorphan, thereby completing the present invention. Unlike the agonists of opioid, the δ-antagonists do not cause drug dependence, psychotomimetic and aversion, so that selective antitussive effect can be expected.

That is, the present invention provides an antitussive comprising as an effective ingredient a δ-opioid antagonist or a pharmaceutically acceptable salt thereof.

By the present invention, an antitussive of which action mechanism is totally different from that of the conventional antitussives having serious side effects such as drug dependence, psychotomimetic and aversion, which has a high activity and which may also be orally administered was provided.

BRIEF DESCRIPTION OF THE DRAWINGS

FIG. 3 shows the influence by Compound 3 (BNTX) on capsaicin-induced cough.

BEST MODE FOR CARRYING OUT THE INVENTION

Figure 1:
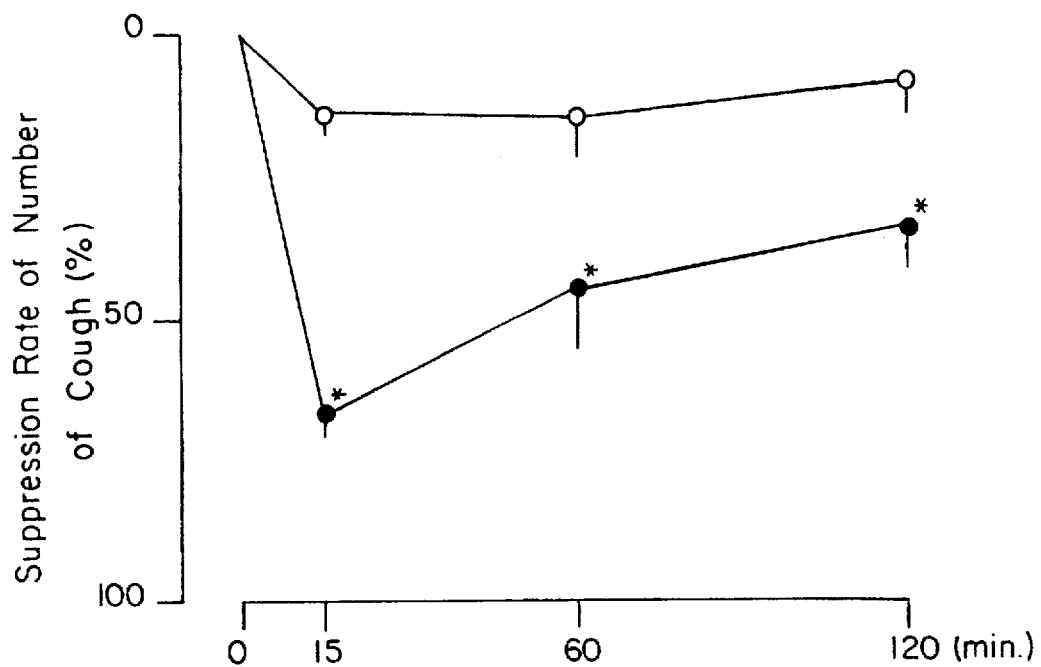
FIG. 1 shows the influence by Compound 1 (naltrindole: NTI) on capsaicin-induced cough.

As mentioned above, the antitussive according to the present invention comprises as an effective ingredient a δ-antagonist or a pharmaceutically acceptable salt thereof.

Examples of the δ-antagonists include those represented by the following formula (I):

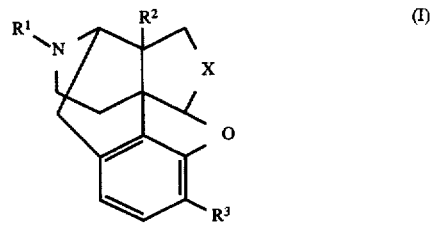

{wherein $R^1$ represents $C_1$–$C_5$ alkyl, $C_4$–$C_7$ cycloalkylalkyl, $C_5$–$C_7$ cycloalkenylalkyl, $C_6$–$C_{12}$ aryl, $C_7$–$C_{13}$ aralkyl, $C_4$–$C_7$ alkenyl, allyl, $C_1$–$C_5$ furan-2-ylalkyl or $C_1$–$C_5$ thiophene-2-ylalkyl; $R^2$ represents hydrogen, hydroxy, $C_1$–$C_5$ alkanoyloxy, $C_1$–$C_5$ alkoxy, $C_7$–$C_{13}$ arylcarbonyloxy or $C_7$–$C_{13}$ aralkyloxy; $R^3$ represents hydrogen, hydroxy, $C_1$–$C_5$ alkanoyloxy, $C_1$–$C_5$ alkoxy, $C_7$–$C_{13}$ arylcarbonyloxy or $C_7$–$C_{13}$ aralkyloxy; X represents

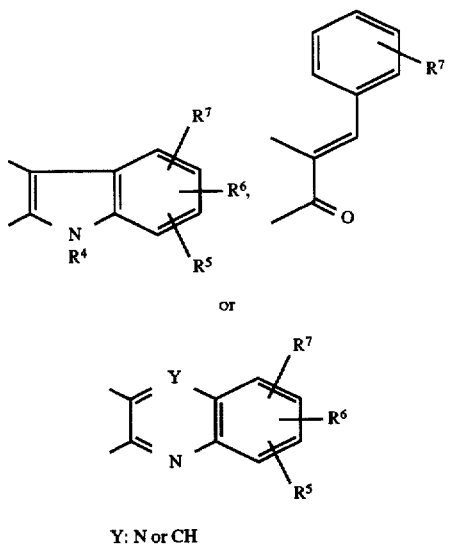

Y: N or CH (wherein $R^4$ represents hydrogen, $C_1$–$C_5$ alkyl or $C_7$–$C_{13}$ aralkyl; $R^5$, $R^6$ and $R^7$ independently represent hydrogen, fluorine, chlorine, bromine, nitro, $C_1$–$C_5$ alkyl, $C_1$–$C_5$ alkoxy, isothiocyanato, iodine, trifluoromethyl, trifluoromethoxy, cyano, phenyl, $C_1$–$C_3$ hydroxyalkyl, $SR^8$, $SOR^8$, $SO_2R^8$, $(CH_2)_mCO_2R^8$ (wherein m represents an integer of 0–3, $R^8$ represents $C_1$–$C_5$ alkyl), $SO_2NR^9R^{10}$, $CONR^9R^{10}$, $(CH_2)_nNR^9R^{10}$ (wherein n represents an integer of 0–3, $R^9$ and $R^{10}$ independently represent hydrogen, $C_1$–$C_5$ alkyl or $C_4$–$C_6$ cycloalkylalkyl), or $R^7$ represents the same meaning mentioned above and binds $R^5$ and $R^6$ to form ① $C_3$–$C_6$ alkylene (with the proviso that one or more of the hydrogen atoms in the alkylene moiety may be substituted with $R^{11}$ (wherein $R^{11}$ represents $C_1$–$C_5$ alkyl, $C_1$–$C_5$ alkoxy, $C_1$–$C_5$ alkanoyl, $C_1$–$C_5$ hydroxyalkyl, $SR^8$, $SOR^8$, $SO_2R^8$, $(CH_2)_mCO_2R^8$, $SO_2NR^9R^{10}$, $CONR^9R^{10}$, $(CH_2)_nNR^9R^{10}$ (wherein m, n, $R^8$, $R^9$ and $R^{10}$ represent the same meanings as mentioned above), said alkylene being bound to adjacent carbon atoms in the benzene ring to form a ring), or ② —S=T—U=V— (wherein S, T, U and V represent nitrogen or CH (wherein this hydrogen may be substituted with $R^{12}$ (wherein $R^{12}$ represents fluorine, chlorine, bromine, nitro, $C_1$–$C_5$ alkyl, $C_1$–$C_5$ alkoxy, isothiocyanato, iodine, trifluoromethyl, trifluoromethoxy, cyano, phenyl, $C_1$–$C_3$ hydroxyalkyl, $SR^8$, $SOR^8$, $SO_2R^8$, $(CH_2)_mCO_2R^8$, $SO_2NR^9R^{10}$, $CONR^9R^{10}$, $(CH_2)_nNR^9R^{10}$ (wherein m, n, $R^8$, $R^9$ and $R^{10}$ represent the same meanings as mentioned above)), said —S=T—U=V— being bound to adjacent carbon atoms in the benzene ring to form a ring); the formula (I) including (+) isomers, (−) isomers and racemates}.

The compounds of the formula (I) include those represented by the following formulae (Ia), (Ib) and (Ic).

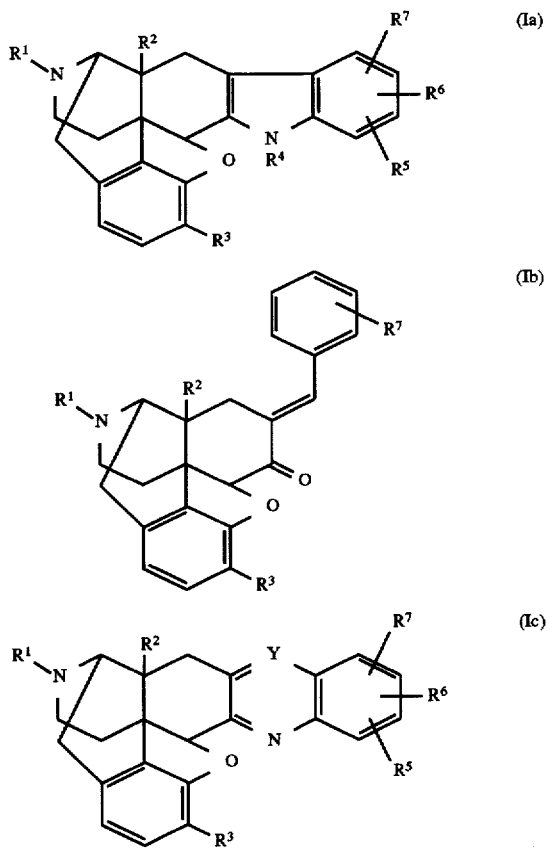

Y: N or CH (In formulae (Ia), (Ib) and (Ic), $R^1$, $R^2$, $R^3$, $R^4$, $R^5$, $R^6$ and $R^7$ represent the same meanings as in formula (I)).

Among the compounds represented by the formula (Ia), indole derivatives represented by the formula (II) in which $R^5$ and $R^6$ are bound are preferred compounds.

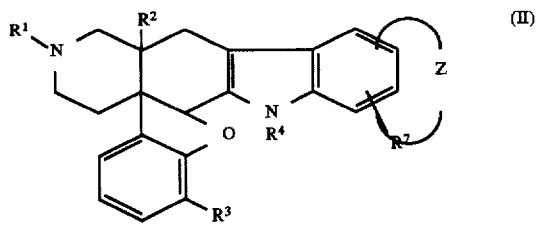

(wherein $R^1$, $R^2$, $R^3$, $R^4$ and $R^7$ represent the same meanings as in formula (I), Z represents $C_3$–$C_6$ alkylene (with the proviso that one or more hydrogen atoms on the alkylene moiety may be substituted with $R^{11}$ (wherein $R^{11}$ represents the same meaning as mentioned above), or —S=T—U=V— (wherein S, T, U and V represent the same meanings as mentioned above, and hydrogen atom(s) therein may be substituted with $R^{12}$ (wherein $R^{12}$ represents the same meaning as mentioned above), said alkylene or —S=T—U=V— being bound to the adjacent carbon atoms in the benzene ring to form a ring).

Further, the compounds represented by the formula (IIa) wherein $R^1$, $R^2$, $R^3$, $R^4$ and $R^7$ represent the same meanings as mentioned above; Z represents —S=T—U=V— (wherein S, T, U and V represent the same meanings as mentioned above, and hydrogen atom(s) therein may be substituted with $R^{12}$ (wherein $R^{12}$ represents the same meaning as mentioned above), said —S=T—U=V— being bound to the adjacent carbon atoms in the benzene ring to form a ring), are preferred.

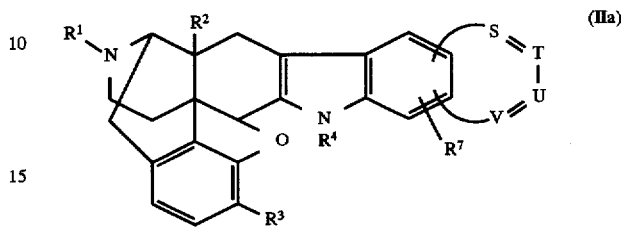

Here, $R^1$ may preferably be $C_1$–$C_5$ alkyl, $C_4$–$C_7$ cycloalkylalkyl, $C_7$–$C_{13}$ aralkyl, $C_4$–$C_7$ alkenyl, allyl or furan-2-ylalkyl. Among these, methyl, ethyl, propyl, cyclopropylmethyl, cyclobutylmethyl, benzyl, phenetyl, butenyl, allyl, furan-2-ylmethyl are especially preferred. $R^2$ and $R^3$ may preferably be hydrogen, hydroxy, $C_1$–$C_5$ alkanoyloxy, $C_1$–$C_5$ alkoxy or $C_7$–$C_{13}$ aralkyloxy. Among these, hydrogen, hydroxy, acetoxy, methoxy, ethoxy, propoxy and benzyloxy are especially preferred. $R^4$ may preferably be hydrogen or $C_1$–$C_5$ alkyl. Among these, hydrogen and methyl are especially preferred. $R^7$ may preferably be hydrogen, halogene, nitro, $C_1$–$C_5$ alkyl, $C_1$–$C_5$ alkoxy or $CO_2R^8$ (wherein $R^8$ represents $C_1$–$C_5$ alkyl). Among these, hydrogen, fluorine, chlorine, bromine, nitro, methyl, methoxy and methoxycarbonyl are especially preferred.

Further, the compounds represented by formula (III):

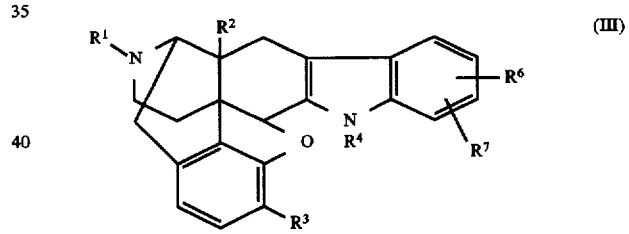

in which $R^5$ is hydrogen are also preferred. In this case, $R^6$ and $R^7$ may preferably be hydrogen, halogen, nitro, $C_1$–$C_5$ alkyl, $C_1$–$C_5$ alkoxy, isothiocyanato, trifluoromethyl, trifluoromethoxy, cyano, phenyl, $C_1$–$C_3$ hydroxyalkyl $SR^8$, $SOR^8$, $SO_2R^8$, $(CH_2)_mCO_2R^8$ (wherein m represents an integer of 0–3, $R^8$ represents $C_1$–$C_5$ alkyl), $SO_2NR^9R^{10}$, $CONR^9R^{10}$, $(CH_2)_nNR^9R^{10}$ (wherein n represents an integer of 0–3, $R^9$ and $R^{10}$ independently represent hydrogen, $C_1$–$C_5$ alkyl, $C_4$–$C_6$ cycloalkylalkyl), or amino. Among these, hydrogen, fluorine, chlorine, bromine, iodine, nitro, methyl, methoxy, isothiocyanato, trifluoromethyl, trifluoromethoxy, cyano, phenyl, hydroxymethyl, hydroxyethyl, methylthio, methylsulfinyl, methylsulfonyl, methoxycarbonyl, ethoxycarbonyl, propoxycarbonyl, methoxycarbonylmethyl, ethoxycarbonylmethyl, sulfamoyl, dimethylsulfamoyl, cyclopropylmethylsulfamoyl, dimethylcarbamoyl, cyclopropylmethylcarbamoyl, dimethylaminomethyl, dimethylaminoethyl, cyclopropylmethylaminomethyl and amino are especially preferred.

Among the compounds represented by formula (Ia), the compound in which $R^1$ is cyclopropylmethyl, $R^2$ and $R^3$ are hydroxy, and $R^4$, $R^5$, $R^6$ and $R^7$ are hydrogen, that is, the Compound 1 is named
17-cyclopropylmethyl-6,7-didehydro-4,5α-epoxy-3,14β-dihydroxy-6,7,2',3'-indolomorphinan.

According to this nomenclature, specific examples of the compounds employed in the present invention include
17-allyl-6,7-didehydro-4,5α-epoxy-3,14β-dihydroxy-6,7,2',3'-indolomorphinan,
17-cyclopropylmethyl-6,7-didehydro-4,5α-epoxy-14β-hydroxy-3-methoxy-6,7,2',3'-indolomorphinan,
17-allyl-6,7-didehydro-4,5α-epoxy-14β-hydroxy-3-methoxy-6,7,2',3'-indolomorphinan,
17-cyclopropylmethyl-6,7-didehydro-4,5α-epoxy-3,14β-dihydroxy-4'-methyl-6,7,2',3'-indolomorphinan,
17-allyl-6,7-didehydro-4,5α-epoxy-3,14β-dihydroxy-4'-methyl-6,7,2',3'-indolomorphinan,
17-cyclopropylmethyl-6,7-didehydro-4,5α-epoxy-14β-hydroxy-3-methoxy-4'-methyl-6,7,2',3'-indolomorphinan,
17-allyl-6,7-didehydro-4,5α-epoxy-14β-hydroxy-3-methoxy-4'-methyl-6,7,2',3'-indolomorphinan,
17-cyclopropylmethyl-6,7-didehydro-4,5α-epoxy-3,14β-dihydroxy-5'-methyl-6,7,2',3'-indolomorphinan,
17-allyl-6,7-didehydro-4,5α-epoxy-3,14β-dihydroxy-5'-methyl-6,7,2',3'-indolomorphinan,
17-cyclopropylmethyl-6,7-didehydro-4,5α-epoxy-14β-hydroxy-3-methoxy-5'-methyl-6,7,2',3'-indolomorphinan,
17-allyl-6,7-didehydro-4,5α-epoxy-14β-hydroxy-3-methoxy-5'-methyl-6,7,2',3'-indolomorphinan,
17-cyclopropylmethyl-6,7-didehydro-4,5α-epoxy-3,14β-dihydroxy-6'-methyl-6,7,2',3'-indolomorphinan,
17-allyl-6,7-didehydro-4,5α-epoxy-3,14β-dihydroxy-6'-methyl-6,7,2',3'-indolomorphinan,
17-cyclopropylmethyl-6,7-didehydro-4,5α-epoxy-14β-hydroxy-3-methoxy-6'-methyl-6,7,2',3'-indolomorphinan,
17-allyl-6,7-didehydro-4,5α-epoxy-14β-hydroxy-3-methoxy-6'-methyl-6,7,2',3'-indolomorphinan,
17-cyclopropylmethyl-6,7-didehydro-4,5α-epoxy-3,14β-dihydroxy-7'-methyl-6,7,2',3'-indolomorphinan,
17-allyl-6,7-didehydro-4,5α-epoxy-3,14β-dihydroxy-7'-methyl-6,7,2',3'-indolomorphinan,
17-cyclopropylmethyl-6,7-didehydro-4,5α-epoxy-14β-hydroxy-3-methoxy-7'-methyl-6,7,2',3'-indolomorphinan,
17-allyl-6,7-didehydro-4,5α-epoxy-14β-hydroxy-3-methoxy-7'-methyl-6,7,2',3'-indolomorphinan,
17-cyclopropylmethyl-6,7-didehydro-4,5α-epoxy-3,14β-dihydroxy-4'-chloro-6,7,2',3'-indolomorphinan,
17-allyl-6,7-didehydro-4,5α-epoxy-3,14β-dihydroxy-4'-chloro-6,7,2',3'-indolomorphinan,
17-cyclopropylmethyl-6,7-didehydro-4,5α-epoxy-14β-hydroxy-3-methoxy-4'-chloro-6,7,2',3'-indolomorphinan,
17-allyl-6,7-didehydro-4,5α-epoxy-14β-hydroxy-3-methoxy-4'-chloro-6,7,2',3'-indolomorphinan,
17-cyclopropylmethyl-6,7-didehydro-4,5α-epoxy-3,14β-dihydroxy-5'-chloro-6,7,2',3'-indolomorphinan,
17-allyl-6,7-didehydro-4,5α-epoxy-3,14β-dihydroxy-5'-chloro-6,7,2',3'-indolomorphinan,
17-cyclopropylmethyl-6,7-didehydro-4,5α-epoxy-14β-hydroxy-3-methoxy-5'-chloro-6,7,2',3'-indolomorphinan,
17-allyl-6,7-didehydro-4,5α-epoxy-14β-hydroxy-3-methoxy-5'-chloro-6,7,2',3'-indolomorphinan,
17-cyclopropylmethyl-6,7-didehydro-4,5α-epoxy-3,14β-dihydroxy-6'-chloro-6,7,2',3'-indolomorphinan,
17-allyl-6,7-didehydro-4,5α-epoxy-3,14β-dihydroxy-6'-chloro-6,7,2',3'-indolomorphinan,
17-cyclopropylmethyl-6,7-didehydro-4,5α-epoxy-14β-hydroxy-3-methoxy-6'-chloro-6,7,2',3'-indolomorphinan,
17-allyl-6,7-didehydro-4,5α-epoxy-14β-hydroxy-3-methoxy-6'-chloro-6,7,2',3'-indolomorphinan,
17-cyclopropylmethyl-6,7-didehydro-4,5α-epoxy-3,14β-dihydroxy-7'-chloro-6,7,2',3'-indolomorphinan,
17-allyl-6,7-didehydro-4,5α-epoxy-3,14β-dihydroxy-7'-chloro-6,7,2',3'-indolomorphinan,
17-cyclopropylmethyl-6,7-didehydro-4,5α-epoxy-14β-hydroxy-3-methoxy-7'-chloro-6,7,2',3'-indolomorphinan,
17-allyl-6,7-didehydro-4,5α-epoxy-14β-hydroxy-3-methoxy-7'-chloro-6,7,2',3'-indolomorphinan,
17-cyclopropylmethyl-6,7-didehydro-4,5α-epoxy-3,14β-dihydroxy-4'-fluoro-6,7,2',3'-indolomorphinan,
17-allyl-6,7-didehydro-4,5α-epoxy-3,14β-dihydroxy-4'-fluoro-6,7,2',3'-indolomorphinan,
17-cyclopropylmethyl-6,7-didehydro-4,5α-epoxy-14β-hydroxy-3-methoxy-4'-fluoro-6,7,2',3'-indolomorphinan,
17-allyl-6,7-didehydro-4,5α-epoxy-14β-hydroxy-3-methoxy-4'-fluoro-6,7,2',3'-indolomorphinan,
17-cyclopropylmethyl-6,7-didehydro-4,5α-epoxy-3,14β-dihydroxy-5'-fluoro-6,7,2',3'-indolomorphinan,
17-allyl-6,7-didehydro-4,5α-epoxy-3,14β-dihydroxy-5'-fluoro-6,7,2',3'-indolomorphinan,
17-cyclopropylmethyl-6,7-didehydro-4,5α-epoxy-14β-hydroxy-3-methoxy-5'-fluoro-6,7,2',3'-indolomorphinan,
17-allyl-6,7-didehydro-4,5α-epoxy-14β-hydroxy-3-methoxy-5'-fluoro-6,7,2',3'-indolomorphinan,
17-cyclopropylmethyl-6,7-didehydro-4,5α-epoxy-3,14β-dihydroxy-6'-fluoro-6,7,2',3'-indolomorphinan,
17-allyl-6,7-didehydro-4,5α-epoxy-3,14β-dihydroxy-6'-fluoro-6,7,2',3'-indolomorphinan,
17-cyclopropylmethyl-6,7-didehydro-4,5α-epoxy-14β-hydroxy-3-methoxy-6'-fluoro-6,7,2',3'-indolomorphinan,
17-allyl-6,7-didehydro-4,5α-epoxy-14β-hydroxy-3-methoxy-6'-fluoro-6,7,2',3'-indolomorphinan,
17-cyclopropylmethyl-6,7-didehydro-4,5α-epoxy-3,14β-dihydroxy-7'-fluoro-6,7,2',3'-indolomorphinan,
17-allyl-6,7-didehydro-4,5α-epoxy-3,14β-dihydroxy-7'-fluoro-6,7,2',3'-indolomorphinan,
17-cyclopropylmethyl-6,7-didehydro-4,5α-epoxy-14β-hydroxy-3-methoxy-7'-fluoro-6,7,2',3'-indolomorphinan,
17-allyl-6,7-didehydro-4,5α-epoxy-14β-hydroxy-3-methoxy-7'-fluoro-6,7,2',3'-indolomorphinan,
17-cyclopropylmethyl-6,7-didehydro-4,5=-epoxy-3,14β-dihydroxy-4'-bromo-6,7,2',3'-indolomorphinan,
17-allyl-6,7-didehydro-4,5α-epoxy-3,14β-dihydroxy-4'-bromo-6,7,2',3'-indolomorphinan,
17-cyclopropylmethyl-6,7-didehydro-4,5α-epoxy-14β-hydroxy-3-methoxy-4'-bromo-6,7,2',3'-indolomorphinan,
17-allyl-6,7-didehydro-4,5α-epoxy-14β-hydroxy-3-methoxy-4'-bromo-6,7,2',3'-indolomorphinan,
17-cyclopropylmethyl-6,7-didehydro-4,5α-epoxy-3,14β-dihydroxy-5'-bromo-6,7,2',3'-indolomorphinan,
17-allyl-6,7-didehydro-4,5α-epoxy-3,14β-dihydroxy-5'-bromo-6,7,2',3'-indolomorphinan,
17-cyclopropylmethyl-6,7-didehydro-4,5α-epoxy-14β-hydroxy-3-methoxy-5'-bromo-6,7,2',3'-indolomorphinan,
17-allyl-6,7-didehydro-4,5α-epoxy-14β-hydroxy-3-methoxy-5'-bromo-6,7,2',3'-indolomorphinan, 17-cyclopropylmethyl-6,7-didehydro-4,5α-epoxy-3,14β-dihydroxy-6'-bromo-6,7,2',3'-indolomorphinan, 17-allyl-6,7-didehydro-4,5α-epoxy-3,14β-dihydroxy-6'-bromo-6,7,2',3'-indolomorphinan, 17-cyclopropylmethyl-6,7-didehydro-4,5α-epoxy-14β-hydroxy-3-methoxy-6'-bromo-6,7,2',3'-indolomorphinan, 17-allyl-6,7-didehydro-4,5α-epoxy-14β-hydroxy-3-methoxy-6'-bromo-6,7,2',3'-indolomorphinan, 17-cyclopropylmethyl-6,7-didehydro-4,5α-epoxy-3,14β-dihydroxy-7'-bromo-6,7,2',3'-indolomorphinan, 17-allyl-6,7-didehydro-4,5α-epoxy-3,14β-dihydroxy-7'-bromo-6,7,2',3'-indolomorphinan, 17-cyclopropylmethyl-6,7-didehydro-4,5α-epoxy-14β-hydroxy-3-methoxy-7'-bromo-6,7,2',3'-indolomorphinan, 17-allyl-6,7-didehydro-4,5α-epoxy-14β-hydroxy-3-methoxy-7'-bromo-6,7,2',3'-indolomorphinan, 17-cyclopropylmethyl-6,7-didehydro-4,5α-epoxy-3,14β-dihydroxy-4'-trifluoromethyl-6,7,2',3'-indolomorphinan, 17-allyl-6,7-didehydro-4,5α-epoxy-3,14β-dihydroxy-4,-trifluoromethyl-6,7,2',3'-indolomorphinan, 17-cyclopropylmethyl-6,7-didehydro-4,5α-epoxy-14β-hydroxy-3-methoxy-4'-trifluoromethyl-6,7,2',3'-indolomorphinan, 17-allyl-6,7-didehydro-4,5α-epoxy-14β-hydroxy-3-methoxy-4'-trifluoromethyl-6,7,2',3'-indolomorphinan, 17-cyclopropylmethyl-6,7-didehydro-4,5α-epoxy-3,14β-dihydroxy-5'-trifluoromethyl-6,7,2',3'-indolomorphinan, 17-allyl-6,7-didehydro-4,5α-epoxy-3,14β-dihydroxy-5'-trifluoromethyl-6,7,2',3'-indolomorphinan, 17-cyclopropylmethyl-6,7-didehydro-4,5α-epoxy-14β-hydroxy-3-methoxy-5'-trifluoromethyl-6,7,2',3'-indolomorphinan, 17-allyl-6,7-didehydro-4,5α-epoxy-14β-hydroxy-3-methoxy-5'-trifluoromethyl-6,7,2',3'-indolomorphinan, 17-cyclopropylmethyl-6,7-didehydro-4,5α-epoxy-3,14β-dihydroxy-6'-trifluoromethyl-6,7,2',3'-indolomorphinan, 17-allyl-6,7-didehydro-4,5α-epoxy-3,14β-dihydroxy-6'-trifluoromethyl-6,7,2',3'-indolomorphinan, 17-cyclopropylmethyl-6,7-didehydro-4,5α-epoxy-14β-hydroxy-3-methoxy-6'-trifluoromethyl-6,7,2',3'-indolomorphinan, 17-allyl-6,7-didehydro-4,5α-epoxy-14β-hydroxy-3-methoxy-6'-trifluoromethyl-6,7,2',3'-indolomorphinan, 17-cyclopropylmethyl-6,7-didehydro-4,5α-epoxy-3,14β-dihydroxy-7'-trifluoromethyl-6,7,2',3'-indolomorphinan, 17-allyl-6,7-didehydro-4,5α-epoxy-3,14β-dihydroxy-7'-trifluoromethyl-6,7,2',3'-indolomorphinan, 17-cyclopropylmethyl-6,7-didehydro-4,5α-epoxy-14β-hydroxy-3-methoxy-7'-trifluoromethyl-6,7,2',3'-indolomorphinan, 17-allyl-6,7-didehydro-4,5α-epoxy-14β-hydroxy-3-methoxy-7'-trifluoromethyl-6,7,2',3'-indolomorphinan, 17-cyclopropylmethyl-6,7-didehydro-4,5α-epoxy-3,14β-dihydroxy-4'-methoxycarbonyl-6,7,2',3'-indolomorphinan, 17-allyl-6,7-didehydro-4,5α-epoxy-3,14β-dihydroxy-4'-methoxycarbonyl-6,7,2',3'-indolomorphinan, 17-cyclopropylmethyl-6,7-didehydro-4,5α-epoxy-14β-hydroxy-3-methoxy-4'-methoxycarbonyl-6,7,2',3'-indolomorphinan, 17-allyl-6,7-didehydro-4,5α-epoxy-14β-hydroxy-3-methoxy-4'-methoxycarbonyl-6,7,2',3'-indolomorphinan, 17-cyclopropylmethyl-6,7-didehydro-4,5α-epoxy-3,14β-dihydroxy-5'-methoxycarbonyl-6,7,2',3'-indolomorphinan, 17-allyl-6,7-didehydro-4,5α-epoxy-3,14β-dihydroxy-5'-methoxycarbonyl-6,7,2',3'-indolomorphinan, 17-cyclopropylmethyl-6,7-didehydro-4,5α-epoxy-14β-hydroxy-3-methoxy-5'-methoxycarbonyl-6,7,2',3'-indolomorphinan, 17-allyl-6,7-didehydro-4,5α-epoxy-14β-hydroxy-3-methoxy-5'-methoxycarbonyl-6,7,2',3'-indolomorphinan, 17-cyclopropylmethyl-6,7-didehydro-4,5α-epoxy-3,14β-dihydroxy-6'-methoxycarbonyl-6,7,2',3'-indolomorphinan, 17-allyl-6,7-didehydro-4,5α-epoxy-3,14β-dihydroxy-6'-methoxycarbonyl-6,7,2',3'-indolomorphinan, 17-cyclopropylmethyl-6,7-didehydro-4,5α-epoxy-14β-hydroxy-3-methoxy-6'-methoxycarbonyl-6,7,2',3'-indolomorphinan, 17-allyl-6,7-didehydro-4,5α-epoxy-14β-hydroxy-3-methoxy-6'-methoxycarbonyl-6,7,2',3'-indolomorphinan, 17-cyclopropylmethyl-6,7-didehydro-4,5α-epoxy-3,14β-dihydroxy-7'-methoxycarbonyl-6,7,2',3'-indolomorphinan, 17-allyl-6,7-didehydro-4,5α-epoxy-3,14β-dihydroxy-7'-methoxycarbonyl-6,7,2',3'-indolomorphinan, 17-cyclopropylmethyl-6,7-didehydro-4,5α-epoxy-14β-hydroxy-3-methoxy-7'-methoxycarbonyl-6,7,2',3'-indolomorphinan, 17-allyl-6,7-didehydro-4,5α-epoxy-14β-hydroxy-3-methoxy-7'-methoxycarbonyl-6,7,2',3'-indolomorphinan, 17-cyclopropylmethyl-6,7-didehydro-4,5α-epoxy-3,14β-dihydroxy-4'-ethoxycarbonyl-6,7,2',3'-indolomorphinan, 17-allyl-6,7-didehydro-4,5α-epoxy-3,14β-dihydroxy-4'-ethoxycarbonyl-6,7,2',3'-indolomorphinan, 17-cyclopropylmethyl-6,7-didehydro-4,5α-epoxy-14β-hydroxy-3-methoxy-4'-ethoxycarbonyl-6,7,2',3'-indolomorphinan, 17-allyl-6,7-didehydro-4,5α-epoxy-14β-hydroxy-3-methoxy-4'-ethoxycarbonyl-6,7,2',3'-indolomorphinan, 17-cyclopropylmethyl-6,7-didehydro-4,5α-epoxy-3,14β-dihydroxy-5'-ethoxycarbonyl-6,7,2',3'-indolomorphinan, 17-allyl-6,7-didehydro-4,5α-epoxy-3,14β-dihydroxy-5'-ethoxycarbonyl-6,7,2',3'-indolomorphinan, 17-cyclopropylmethyl-6,7-didehydro-4,5α-epoxy-14β-hydroxy-3-methoxy-5'-ethoxycarbonyl-6,7,2',3'-indolomorphinan, 17-allyl-6,7-didehydro-4,5α-epoxy-14β-hydroxy-3-methoxy-5'-ethoxycarbonyl-6,7,2',3'-indolomorphinan, 17-cyclopropylmethyl-6,7-didehydro-4,5α-epoxy-3,14β-dihydroxy-6'-ethoxycarbonyl-6,7,2',3'-indolomorphinan, 17-allyl-6,7-didehydro-4,5α-epoxy-3,14β-dihydroxy-6'-ethoxycarbonyl-6,7,2',3'-indolomorphinan, 17-cyclopropylmethyl-6,7-didehydro-4,5α-epoxy-14β-hydroxy-3-methoxy-6'-ethoxycarbonyl-6,7,2',3'-indolomorphinan, 17-allyl-6,7-didehydro-4,5α-epoxy-14β-hydroxy-3-methoxy-6'-ethoxycarbonyl-6,7,2',3'-indolomorphinan, 17-cyclopropylmethyl-6,7-didehydro-4,5α-epoxy-3,14β-dihydroxy-7'-ethoxycarbonyl-6,7,2',3'-indolomorphinan, 17-allyl-6,7-didehydro-4,5α-epoxy-3,14β-dihydroxy-7'-ethoxycarbonyl-6,7,2',3'-indolomorphinan, 17-cyclopropylmethyl-6,7-didehydro-4,5α-epoxy-14β-hydroxy-3-methoxy-7'-ethoxycarbonyl-6,7,2',3'-indolomorphinan, 17-allyl-6,7-didehydro-4,5α-epoxy-14β-hydroxy-3-methoxy-7'-ethoxycarbonyl-6,7,2',3'-indolomorphinan, 17-cyclopropylmethyl-6,7-didehydro-4,5α-epoxy-3,14β-dihydroxy-4'-propoxycarbonyl-6,7,2',3'-indolomorphinan, 17-allyl-6,7-didehydro-4,5α-epoxy-3,14β-dihydroxy-4'-propoxycarbonyl-6,7,2',3'-indolomorphinan, 17-cyclopropylmethyl-6,7-didehydro-4,5α-epoxy-14β-hydroxy-3-methoxy-4'-propoxycarbonyl-6,7,2',3'-indolomorphinan, 17-allyl-6,7-didehydro-4,5α-epoxy-14β-hydroxy-3-methoxy-4'-propoxycarbonyl-6,7,2',3'-indolomorphinan, 17-cyclopropylmethyl-6,7-didehydro-4,5α-epoxy-3,14β-dihydroxy-5'-propoxycarbonyl-6,7,2',3'-indolomorphinan, 17-allyl-6,7-didehydro-4,5α-epoxy-3,14β-dihydroxy-5'-propoxycarbonyl-6,7,2',3'-indolomorphinan, 17-cyclopropylmethyl-6,7-didehydro-4,5α-epoxy-14β-hydroxy-3-methoxy-5'-propoxycarbonyl-6,7,2',3'-indolomorphinan, 17-allyl-6,7-didehydro-4,5α-epoxy-14β-hydroxy-3-methoxy-5'-propoxycarbonyl-6,7,2',3'-indolomorphinan, 17-cyclopropylmethyl-6,7-didehydro-4,5α-epoxy-3,14β-dihydroxy-6'-propoxycarbonyl-6,7,2',3'-indolomorphinan, 17-allyl-6,7-didehydro-4,5α-epoxy-3,14β-dihydroxy-6'-propoxycarbonyl-6,7,2',3'-indolomorphinan, 17-cyclopropylmethyl-6,7-didehydro-4,5α-epoxy-14β-hydroxy-3-methoxy-6'-propoxycarbonyl-6,7,2',3'-indolomorphinan, 17-allyl-6,7-didehydro-4,5α-epoxy-14β-hydroxy-3-methoxy-6'-propoxycarbonyl-6,7,2',3'-indolomorphinan, 17-cyclopropylmethyl-6,7-didehydro-4,5α-epoxy-3,14β-dihydroxy-7'-propoxycarbonyl-6,7,2',3'-indolomorphinan, 17-allyl-6,7-didehydro-4,5α-epoxy-3,14β-dihydroxy-7'-propoxycarbonyl-6,7,2',3'-indolomorphinan, 17-cyclopropylmethyl-6,7-didehydro-4,5α-epoxy-14β-hydroxy-3-methoxy-7'-propoxycarbonyl-6,7,2',3'-indolomorphinan, 17-allyl-6,7-didehydro-4,5α-epoxy-14β-hydroxy-3-methoxy-7'-propoxycarbonyl-6,7,2',3'-indolomorphinan, 17-cyclopropylmethyl-6,7-didehydro-4,5α-epoxy-3,14β-dihydroxy-4'-trifluoromethoxy-6,7,2',3'-indolomorphinan, 17-allyl-6,7-didehydro-4,5α-epoxy-3,14β-dihydroxy-4'-trifluoromethoxy-6,7,2',3'-indolomorphinan, 17-cyclopropylmethyl-6,7-didehydro-4,5α-epoxy-14β-hydroxy-3-methoxy-4'-trifluoromethoxy-6,7,2',3'-indolomorphinan, 17-allyl-6,7-didehydro-4,5α-epoxy-14β-hydroxy-3-methoxy-4'-trifluoromethoxy-6,7,2',3'-indolomorphinan, 17-cyclopropylmethyl-6,7-didehydro-4,5α-epoxy-3,14β-dihydroxy-5'-trifluoromethoxy-6,7,2',3'-indolomorphinan, 17-allyl-6,7-didehydro-4,5α-epoxy-3,14β-dihydroxy-5'-trifluoromethoxy-6,7,2',3'-indolomorphinan, 17-cyclopropylmethyl-6,7-didehydro-4,5α-epoxy-14β-hydroxy-3-methoxy-5'-trifluoromethoxy-6,7,2',3'-indolomorphinan, 17-allyl-6,7-didehydro-4,5α-epoxy-14β-hydroxy-3-methoxy-5'-trifluoromethoxy-6,7,2',3'-indolomorphinan, 17-cyclopropylmethyl-6,7-didehydro-4,5α-epoxy-3,14β-dihydroxy-6'-trifluoromethoxy-6,7,2',3'-indolomorphinan, 17-allyl-6,7-didehydro-4,5α-epoxy-3,14β-dihydroxy-6'-trifluoromethoxy-6,7,2',3'-indolomorphinan, 17-cyclopropylmethyl-6,7-didehydro-4,5α-epoxy-14β-hydroxy-3-methoxy-6'-trifluoromethoxy-6,7,2',3'-indolomorphinan, 17-allyl-6,7-didehydro-4,5α-epoxy-14β-hydroxy-3-methoxy-6'-trifluoromethoxy-6,7,2',3'-indolomorphinan, 17-cyclopropylmethyl-6,7-didehydro-4,5α-epoxy-3,14β-dihydroxy-7'-trifluoromethoxy-6,7,2',3'-indolomorphinan, 17-allyl-6,7-didehydro-4,5α-epoxy-3,14β-dihydroxy-7'-trifluoromethoxy-6,7,2',3'-indolomorphinan, 17-cyclopropylmethyl-6,7-didehydro-4,5α-epoxy-14β-hydroxy-3-methoxy-7'-trifluoromethoxy-6,7,2',3'-indolomorphinan, 17-allyl-6,7-didehydro-4,5α-epoxy-14β-hydroxy-3-methoxy-7'-trifluoromethoxy-6,7,2',3'-indolomorphinan, 17-cyclopropylmethyl-6,7-didehydro-4,5α-epoxy-3,14β-dihydroxy-4'-methoxy-6,7,2',3'-indolomorphinan, 17-allyl-6,7-didehydro-4,5α-epoxy-3,14β-dihydroxy-4'-methoxy-6,7,2',3'-indolomorphinan, 17-cyclopropylmethyl-6,7-didehydro-4,5α-epoxy-14β-hydroxy-3-methoxy-4'-methoxy-6,7,2',3'-indolomorphinan, 17-allyl-6,7-didehydro-4,5α-epoxy-14β-hydroxy-3-methoxy-4'-methoxy-6,7,2',3'-indolomorphinan, 17-cyclopropylmethyl-6,7-didehydro-4,5α-epoxy-3,14β-dihydroxy-5'-methoxy-6,7,2',3'-indolomorphinan, 17-allyl-6,7-didehydro-4,5α-epoxy-3,14β-dihydroxy-5'-methoxy-6,7,2',3'-indolomorphinan, 17-cyclopropylmethyl-6,7-didehydro-4,5α-epoxy-14β-hydroxy-3-methoxy-5'-methoxy-6,7,2',3'-indolomorphinan, 17-allyl-6,7-didehydro-4,5α-epoxy-14β-hydroxy-3-methoxy-5'-methoxy-6,7,2',3'-indolomorphinan, 17-cyclopropylmethyl-6,7-didehydro-4,5α-epoxy-3,14β-dihydroxy-6'-methoxy-6,7,2',3'-indolomorphinan, 17-allyl-6,7-didehydro-4,5α-epoxy-3,14β-dihydroxy-6'-methoxy-6,7,2',3'-indolomorphinan, 17-cyclopropylmethyl-6,7-didehydro-4,5α-epoxy-14β-hydroxy-3-methoxy-6'-methoxy-6,7,2',3'-indolomorphinan, 17-allyl-6,7-didehydro-4,5α-epoxy-14β-hydroxy-3-methoxy-6'-methoxy-6,7,2',3'-indolomorphinan, 17-cyclopropylmethyl-6,7-didehydro-4,5α-epoxy-3,14β-dihydroxy-7'-methoxy-6,7,2',3'-indolomorphinan, 17-allyl-6,7-didehydro-4,5α-epoxy-3,14β-dihydroxy-7'-methoxy-6,7,2',3'-indolomorphinan, 17-cyclopropylmethyl-6,7-didehydro-4,5α-epoxy-14β-hydroxy-3-methoxy-7'-methoxy-6,7,2',3'-indolomorphinan, 17-allyl-6,7-didehydro-4,5α-epoxy-14β-hydroxy-3-methoxy-7'-methoxy-6,7,2',3'-indolomorphinan, 17-cyclopropylmethyl-6,7-didehydro-4,5α-epoxy-3,14β-dihydroxy-4'-methylthio-6,7,2',3'-indolomorphinan, 17-allyl-6,7-didehydro-4,5α-epoxy-3,14β-dihydroxy-4'-methylthio-6,7,2',3'-indolomorphinan, 17-cyclopropylmethyl-6,7-didehydro-4,5α-epoxy-14β-hydroxy-3-methoxy-4'-methylthio-6,7,2',3'-indolomorphinan, 17-allyl-6,7-didehydro-4,5α-epoxy-14β-hydroxy-3-methoxy-4'-methylthio-6,7,2',3'-indolomorphinan, 17-cyclopropylmethyl-6,7-didehydro-4,5α-epoxy-3,14β-dihydroxy-5'-methylthio-6,7,2',3'-indolomorphinan, 17-allyl-6,7-didehydro-4,5α-epoxy-3,14β-dihydroxy-5'-methylthio-6,7,2',3'-indolomorphinan, 17-cyclopropylmethyl-6,7-didehydro-4,5α-epoxy-14β-hydroxy-3-methoxy-5'-methylthio-6,7,2',3'-indolomorphinan, 17-allyl-6,7-didehydro-4,5α-epoxy-14β-hydroxy-3-methoxy-5'-methylthio-6,7,2',3'-indolomorphinan, 17-cyclopropylmethyl-6,7-didehydro-4,5α-epoxy-3,14β-dihydroxy-6'-methylthio-6,7,2',3'-indolomorphinan, 17-allyl-6,7-didehydro-4,5α-epoxy-3,14β-dihydroxy-6'-methylthio-6,7,2',3'-indolomorphinan, 17-cyclopropylmethyl-6,7-didehydro-4,5α-epoxy-14β-hydroxy-3-methoxy-6'-methylthio-6,7,2',3'-indolomorphinan, 17-allyl-6,7-didehydro-4,5α-epoxy-14β-hydroxy-3-methoxy-6'-methylthio-6,7,2',3'-indolomorphinan, 17-cyclopropylmethyl-6,7-didehydro-4,5α-epoxy-3,14β-dihydroxy-7'-methylthio-6,7,2',3'-indolomorphinan, 17-allyl-6,7-didehydro-4,5α-epoxy-3,14β-dihydroxy-7'-methylthio-6,7,2',3'-indolomorphinan, 17-cyclopropylmethyl-6,7-didehydro-4,5α-epoxy-14β-hydroxy-3-methoxy-7'-methylthio-6,7,2',3'-indolomorphinan, 17-allyl-6,7-didehydro-4,5α-epoxy-14β-hydroxy-3-methoxy-7'-methylthio-6,7,2',3'-indolomorphinan, 17-cyclopropylmethyl-6,7-didehydro-4,5α-epoxy-3,14β-dihydroxy-4'-nitro-6,7,2',3'-indolomorphinan, 17-allyl-6,7-didehydro-4,5α-epoxy-3,14β-dihydroxy-4'-nitro-6,7,2',3'-indolomorphinan, 17-cyclopropylmethyl-6,7-didehydro-4,5α-epoxy-14β-hydroxy-3-methoxy-4'-nitro-6,7,2',3'-indolomorphinan, 17-allyl-6,7-didehydro-4,5α-epoxy-14β-hydroxy-3-methoxy-4'-nitro-6,7,2',3'-indolomorphinan, 17-cyclopropylmethyl-6,7-didehydro-4,5α-epoxy-3,14β-dihydroxy-5'-nitro-6,7,2',3'-indolomorphinan, 17-allyl-6,7-didehydro-4,5α-epoxy-3,14β-dihydroxy-5'-nitro-6,7,2',3'-indolomorphinan, 17-cyclopropylmethyl-6,7-didehydro-4,5α-epoxy-14β-hydroxy-3-methoxy-5'-nitro-6,7,2',3'-indolomorphinan, 17-allyl-6,7-didehydro-4,5α-epoxy-14β-hydroxy-3-methoxy-5'-nitro-6,7,2',3'-indolomorphinan, 17-cyclopropylmethyl-6,7-didehydro-4,5α-epoxy-3,14β-dihydroxy-6'-nitro-6,7,2',3'-indolomorphinan, 17-allyl-6,7-didehydro-4,5α-epoxy-3,14β-dihydroxy-6'-nitro-6,7,2',3'-indolomorphinan, 17-cyclopropylmethyl-6,7-didehydro-4,5α-epoxy-14β-hydroxy-3-methoxy-6'-nitro-6,7,2',3'-indolomorphinan, 17-allyl-6,7-didehydro-4,5α-epoxy-14β-hydroxy-3-methoxy-6'-nitro-6,7,2',3'-indolomorphinan, 17-cyclopropylmethyl-6,7-didehydro-4,5α-epoxy-3,14β-dihydroxy-7'-nitro-6,7,2',3'-indolomorphinan, 17-allyl-6,7-didehydro-4,5α-epoxy-3,14β-dihydroxy-7'-nitro-6,7,2',3'-indolomorphinan, 17-cyclopropylmethyl-6,7-didehydro-4,5α-epoxy-14β-hydroxy-3-methoxy-7'-nitro-6,7,2',3'-indolomorphinan, 17-allyl-6,7-didehydro-4,5α-epoxy-14β-hydroxy-3-methoxy-7'-nitro-6,7,2',3'-indolomorphinan, 17-cyclopropylmethyl-6,7-didehydro-4,5α-epoxy-3,14β-dihydroxy-4'-iodo-6,7,2',3'-indolomorphinan, 17-allyl-6,7-didehydro-4,5α-epoxy-3,14β-dihydroxy-4'-iodo-6,7,2',3'-indolomorphinan, 17-cyclopropylmethyl-6,7-didehydro-4,5α-epoxy-14β-hydroxy-3-methoxy-4'-iodo-6,7,2',3'-indolomorphinan, 17-allyl-6,7-didehydro-4,5α-epoxy-14β-hydroxy-3-methoxy-4'-iodo-6,7,2',3'-indolomorphinan, 17-cyclopropylmethyl-6,7-didehydro-4,5α-epoxy-3,14β-dihydroxy-5'-iodo-6,7,2',3'-indolomorphinan, 17-allyl-6,7-didehydro-4,5α-epoxy-3,14β-dihydroxy-5'-iodo-6,7,2',3'-indolomorphinan, 17-cyclopropylmethyl-6,7-didehydro-4,5α-epoxy-14β-hydroxy-3-methoxy-5'-iodo-6,7,2',3'-indolomorphinan, 17-allyl-6,7-didehydro-4,5α-epoxy-14β-hydroxy-3-methoxy-5'-iodo-6,7,2',3'-indolomorphinan, 17-cyclopropylmethyl-6,7-didehydro-4,5α-epoxy-3,14β-dihydroxy-6'-iodo-6,7,2',3'-indolomorphinan, 17-allyl-6,7-didehydro-4,5α-epoxy-3,14β-dihydroxy-6'-iodo-6,7,2',3'-indolomorphinan, 17-cyclopropylmethyl-6,7-didehydro-4,5α-epoxy-14β-hydroxy-3-methoxy-6'-iodo-6,7,2',3'-indolomorphinan, 17-allyl-6,7-didehydro-4,5α-epoxy-14β-hydroxy-3-methoxy-6'-iodo-6,7,2',3'-indolomorphinan, 17-cyclopropylmethyl-6,7-didehydro-4,5α-epoxy-3,14β-dihydroxy-7'-iodo-6,7,2',3'-indolomorphinan, 17-allyl-6,7-didehydro-4,5α-epoxy-3,14β-dihydroxy-7'-iodo-6,7,2',3'-indolomorphinan, 17-cyclopropylmethyl-6,7-didehydro-4,5α-epoxy-14β-hydroxy-3-methoxy-7'-iodo-6,7,2',3'-indolomorphinan, 17allyl-6,7-didehydro-4,5α-epoxy-14β-hydroxy-3-methoxy-7'-iodo-6,7,2',3'-indolomorphinan, 17-cyclopropylmethyl-6,7-didehydro-4,5α-epoxy-3,14β-dihydroxy-4'-amino-6,7,2',3'-indolomorphinan, 17-allyl-6,7-didehydro-4,5α-epoxy-3,14β-dihydroxy-4'-amino-6,7,2',3'-indolomorphinan, 17-cyclopropylmethyl-6,7-didehydro-4,5α-epoxy-14β-hydroxy-3-methoxy-4'-amino-6,7,2',3'-indolomorphinan, 17-allyl-6,7-didehydro-4,5α-epoxy-14β-hydroxy-3-methoxy-4'-amino-6,7,2',3'-indolomorphinan, 17-cyclopropylmethyl-6,7-didehydro-4,5α-epoxy-3,14β-dihydroxy-5'-amino-6,7,2',3'-indolomorphinan, 17-allyl-6,7-didehydro-4,5α-epoxy-3,14β-dihydroxy-5'-amino-6,7,2',3'-indolomorphinan, 17-cyclopropylmethyl-6,7-didehydro-4,5α-epoxy-14β-hydroxy-3-methoxy-5'-amino-6,7,2',3'-indolomorphinan, 17-allyl-6,7-didehydro-4,5α-epoxy-14β-hydroxy-3-methoxy-5'-amino-6,7,2',3'-indolomorphinan, 17-cyclopropylmethyl-6,7-didehydro-4,5α-epoxy-3,14β-dihydroxy-6'-amino-6,7,2',3'-indolomorphinan, 17-allyl-6,7-didehydro-4,5α-epoxy-3,14β-dihydroxy-6'-amino-6,7,2',3'-indolomorphinan, 17-cyclopropylmethyl-6,7-didehydro-4,5α-epoxy-14β-hydroxy-3-methoxy-6'-amino-6,7,2',3'-indolomorphinan, 17-allyl-6,7-didehydro-4,5α-epoxy-14β-hydroxy-3-methoxy-6'-amino-6,7,2',3'-indolomorphinan, 17-cyclopropylmethyl-6,7-didehydro-4,5α-epoxy-3,14β-dihydroxy-7'-amino-6,7,2',3'-indolomorphinan, 17-allyl-6,7-didehydro-4,5α-epoxy-3,14β-dihydroxy-7'-amino-6,7,2',3'-indolomorphinan, 17-cyclopropylmethyl-6,7-didehydro-4,5α-epoxy-14β-hydroxy-3-methoxy-7'-amino-6,7,2',3'-indolomorphinan, 17-allyl-6,7-didehydro-4,5α-epoxy-14β-hydroxy-3-methoxy-7'-amino-6,7,2',3'-indolomorphinan, 17-cyclopropylmethyl-6,7-didehydro-4,5α-epoxy-3,14β-dihydroxy-4'-phenyl-6,7,2',3'-indolomorphinan, 17-allyl-6,7-didehydro-4,5α-epoxy-3,14β-dihydroxy-4'-phenyl-6,7,2',3'-indolomorphinan, 17-cyclopropylmethyl-6,7-didehydro-4,5α-epoxy-14β-hydroxy-3-methoxy-4'-phenyl-6,7,2',3'-indolomorphinan, 17-allyl-6,7-didehydro-4,5α-epoxy-14β-hydroxy-3-methoxy-4'-phenyl-6,7,2',3'-indolomorphinan, 17-cyclopropylmethyl-6,7-didehydro-4,5α-epoxy-3,14β-dihydroxy-5'-phenyl-6,7,2',3'-indolomorphinan, 17-allyl-6,7-didehydro-4,5α-epoxy-3,14β-dihydroxy-5'-phenyl-6,7,2',3'-indolomorphinan, 17-cyclopropylmethyl-6,7-didehydro-4,5α-epoxy-14β-hydroxy-3-methoxy-5'-phenyl-6,7,2',3'-indolomorphinan, 17-allyl-6,7-didehydro-4,5α-epoxy-14β-hydroxy-3-methoxy-5'-phenyl-6,7,2',3'-indolomorphinan, 17-cyclopropylmethyl-6,7-didehydro-4,5α-epoxy-3,14β-dihydroxy-6'-phenyl-6,7,2',3'-indolomorphinan, 17-allyl-6,7-didehydro-4,5α-epoxy-3,14β-dihydroxy-6'-phenyl-6,7,2',3'-indolomorphinan, 17-cyclopropylmethyl-6,7-didehydro-4,5α-epoxy-14β-hydroxy-3-methoxy-6'-phenyl-6,7,2',3'-indolomorphinan, 17-allyl-6,7-didehydro-4,5α-epoxy-14β-hydroxy-3-methoxy-6'-phenyl-6,7,2',3'-indolomorphinan, 17-cyclopropylmethyl-6,7-didehydro-4,5α-epoxy-3,14β-dihydroxy-7'-phenyl-6,7,2',3'-indolomorphinan, 17-allyl-6,7-didehydro-4,5α-epoxy-3,14β-dihydroxy-7'-phenyl-6,7,2',3'-indolomorphinan, 17-cyclopropylmethyl-6,7-didehydro-4,5α-epoxy-14β-hydroxy-3-methoxy-7'-phenyl-6,7,2',3'-indolomorphinan, 17-allyl-6,7-didehydro-4,5α-epoxy-14β-hydroxy-3-methoxy-7'-phenyl-6,7,2',3'-indolomorphinan,
17-cyclopropylmethyl-6,7-didehydro-4,5α-epoxy-3,14β-dihydroxy-4'-cyano-6,7,2',3'-indolomorphinan,
17-allyl-6,7-didehydro-4,5α-epoxy-3,14β-dihydroxy-4'-cyano-6,7,2',3'-indolomorphinan,
17-cyclopropylmethyl-6,7-didehydro-4,5α-epoxy-14β-hydroxy-3-methoxy-4'-cyano-6,7,2',3'-indolomorphinan,
17-allyl-6,7-didehydro-4,5α-epoxy-14β-hydroxy-3-methoxy-4'-cyano-6,7,2',3'-indolomorphinan,
17-cyclopropylmethyl-6,7-didehydro-4,5α-epoxy-3,14β-dihydroxy-5'-cyano-6,7,2',3'-indolomorphinan,
17-allyl-6,7-didehydro-4,5α-epoxy-3,14β-dihydroxy-5'-cyano-6,7,2',3'-indolomorphinan,
17-cyclopropylmethyl-6,7-didehydro-4,5α-epoxy-14β-hydroxy-3-methoxy-5'-cyano-6,7,2',3'-indolomorphinan,
17-allyl-6,7-didehydro-4,5α-epoxy-14β-hydroxy-3-methoxy-5'-cyano-6,7,2',3'-indolomorphinan,
17-cyclopropylmethyl-6,7-didehydro-4,5α-epoxy-3,14β-dihydroxy-6'-cyano-6,7,2',3'-indolomorphinan,
17-allyl-6,7-didehydro-4,5α-epoxy-3,14β-dihydroxy-6'-cyano-6,7,2',3'-indolomorphinan,
17-cyclopropylmethyl-6,7-didehydro-4,5α-epoxy-14β-hydroxy-3-methoxy-6'-cyano-6,7,2',3'-indolomorphinan,
17-allyl-6,7-didehydro-4,5α-epoxy-14β-hydroxy-3-methoxy-6'-cyano-6,7,2',3'-indolomorphinan,
17-cyclopropylmethyl-6,7-didehydro-4,5α-epoxy-3,14β-dihydroxy-7'-cyano-6,7,2',3'-indolomorphinan,
17-allyl-6,7-didehydro-4,5α-epoxy-3,14β-dihydroxy-7'-cyano-6,7,2',3'-indolomorphinan,
17-cyclopropylmethyl-6,7-didehydro-4,5α-epoxy-14β-hydroxy-3-methoxy-7'-cyano-6,7,2',3'-indolomorphinan,
17-allyl-6,7-didehydro-4,5α-epoxy-14β-hydroxy-3-methoxy-7'-cyano-6,7,2',3'-indolomorphinan,
17-cyclopropylmethyl-6,7-didehydro-4,5α-epoxy-3,14β-dihydroxy-4'-isothiocyanato-6,7,2',3'-indolomorphinan,
17-allyl-6,7-didehydro-4,5α-epoxy-3,14β-dihydroxy-4'-isothiocyanato-6,7,2',3'-indolomorphinan,
17-cyclopropylmethyl-6,7-didehydro-4,5α-epoxy-14β-hydroxy-3-methoxy-4'-isothiocyanato-6,7,2',3'-indolomorphinan,
17-allyl-6,7-didehydro-4,5α-epoxy-14β-hydroxy-3-methoxy-4'-isothiocyanato-6,7,2',3'-indolomorphinan,
17-cyclopropylmethyl-6,7-didehydro-4,5α-epoxy-3,14β-dihydroxy-5'-isothiocyanato-6,7,2',3'-indolomorphinan,
17-allyl-6,7-didehydro-4,5α-epoxy-3,14β-dihydroxy-5'-isothiocyanato-6,7,2',3'-indolomorphinan,
17-cyclopropylmethyl-6,7-didehydro-4,5α-epoxy-14β-hydroxy-3-methoxy-5'-isothiocyanato-6,7,2',3'-indolomorphinan,
17-allyl-6,7-didehydro-4,5α-epoxy-14β-hydroxy-3-methoxy-5'-isothiocyanato-6,7,2',3'-indolomorphinan,
17-cyclopropylmethyl-6,7-didehydro-4,5α-epoxy-3,14β-dihydroxy-6'-isothiocyanato-6,7,2',3'-indolomorphinan,
17-allyl-6,7-didehydro-4,5α-epoxy-3,14β-dihydroxy-6'-isothiocyanato-6,7,2',3'-indolomorphinan,
17-cyclopropylmethyl-6,7-didehydro-4,5α-epoxy-14β-hydroxy-3-methoxy-6'-isothiocyanato-6,7,2',3'-indolomorphinan,
17-allyl-6,7-didehydro-4,5α-epoxy-14β-hydroxy-3-methoxy-6'-isothiocyanato-6,7,2',3'-indolomorphinan,
17-cyclopropylmethyl-6,7-didehydro-4,5α-epoxy-3,14β-dihydroxy-7'-isothiocyanato-6,7,2',3'-indolomorphinan,
17-allyl-6,7-didehydro-4,5α-epoxy-3,14β-dihydroxy-7'-isothiocyanato-6,7,2',3'-indolomorphinan,
17-cyclopropylmethyl-6,7-didehydro-4,5α-epoxy-14β-hydroxy-3-methoxy-7'-isothiocyanato-6,7,2',3'-indolomorphinan,
17-allyl-6,7-didehydro-4,5α-epoxy-14β-hydroxy-3-methoxy-7'-isothiocyanato-6,7,2',3'-indolomorphinan,
17-cyclopropylmethyl-6,7-didehydro-4,5α-epoxy-3,14β-dihydroxy-4'-methylsulfonyl-6,7,2',3'-indolomorphinan,
17-allyl-6,7-didehydro-4,5α-epoxy-3,14β-dihydroxy-4'-methylsulfonyl-6,7,2',3'-indolomorphinan,
17-cyclopropylmethyl-6,7-didehydro-4,5α-epoxy-14β-hydroxy-3-methoxy-4'-methylsulfonyl-6,7,2',3'-indolomorphinan,
17-allyl-6,7-didehydro-4,5α-epoxy-14β-hydroxy-3-methoxy-4'-methylsulfonyl-6,7,2',3'-indolomorphinan,
17-cyclopropylmethyl-6,7-didehydro-4,5α-epoxy-3,14β-dihydroxy-5'-methylsulfonyl-6,7,2',3'-indolomorphinan,
17-allyl-6,7-didehydro-4,5α-epoxy-3,14β-dihydroxy-5'-methylsulfonyl-6,7,2',3'-indolomorphinan,
17-cyclopropylmethyl-6,7-didehydro-4,5α-epoxy-14β-hydroxy-3-methoxy-5'-methylsulfonyl-6,7,2',3'-indolomorphinan,
17-allyl-6,7-didehydro-4,5α-epoxy-14β-hydroxy-3-methoxy-5'-methylsulfonyl-6,7,2',3'-indolomorphinan,
17-cyclopropylmethyl-6,7-didehydro-4,5α-epoxy-3,14β-dihydroxy-6'-methylsulfonyl-6,7,2',3'-indolomorphinan,
17-allyl-6,7-didehydro-4,5α-epoxy-3,14β-dihydroxy-6'-methylsulfonyl-6,7,2',3'-indolomorphinan,
17-cyclopropylmethyl-6,7-didehydro-4,5α-epoxy-14β-hydroxy-3-methoxy-6'-methylsulfonyl-6,7,2',3'-indolomorphinan,
17-allyl-6,7-didehydro-4,5α-epoxy-14β-hydroxy-3-methoxy-6'-methylsulfonyl-6,7,2',3'-indolomorphinan,
17-cyclopropylmethyl-6,7-didehydro-4,5α-epoxy-3,14β-dihydroxy-7'-methylsulfonyl-6,7,2',3'-indolomorphinan,
17-allyl-6,7-didehydro-4,5α-epoxy-3,14β-dihydroxy-7'-methylsulfonyl-6,7,2',3'-indolomorphinan,
17-cyclopropylmethyl-6,7-didehydro-4,5α-epoxy-14β-hydroxy-3-methoxy-7'-methylsulfonyl-6,7,2',3'-indolomorphinan,
17-allyl-6,7-didehydro-4,5α-epoxy-14β-hydroxy-3-methoxy-7'-methylsulfonyl-6,7,2',3'-indolomorphinan,
17-cyclopropylmethyl-6,7-didehydro-4,5α-epoxy-3,14β-dihydroxy-4'-methylsulfinyl-6,7,2',3'-indolomorphinan,
17-allyl-6,7-didehydro-4,5α-epoxy-3,14β-dihydroxy-4'-methylsulfinyl-6,7,2',3'-indolomorphinan,
17-cyclopropylmethyl-6,7-didehydro-4,5α-epoxy-14β-hydroxy-3-methoxy-4'-methylsulfinyl-6,7,2',3'-indolomorphinan,
17-allyl-6,7-didehydro-4,5α-epoxy-14β-hydroxy-3-methoxy-4'-methylsulfinyl-6,7,2',3'-indolomorphinan,
17-cyclopropylmethyl-6,7-didehydro-4,5α-epoxy-3,14β-dihydroxy-5'-methylsulfinyl-6,7,2',3'-indolomorphinan,
17-allyl-6,7-didehydro-4,5α-epoxy-3,14β-dihydroxy-5'-methylsulfinyl-6,7,2',3'-indolomorphinan,
17-cyclopropylmethyl-6,7-didehydro-4,5α-epoxy-14β-hydroxy-3-methoxy-5'-methylsulfinyl-6,7,2',3'-indolomorphinan,
17-allyl-6,7-didehydro-4,5α-epoxy-14β-hydroxy-3-methoxy-5'-methylsulfinyl-6,7,2',3'-indolomorphinan,
17-cyclopropylmethyl-6,7-didehydro-4,5α-epoxy-3,14β-dihydroxy-6'-methylsulfinyl-6,7,2',3'-indolomorphinan,
17-allyl-6,7-didehydro-4,5α-epoxy-3,14β-dihydroxy-6'-methylsulfinyl-6,7,2',3'-indolomorphinan,
17-cyclopropylmethyl-6,7-didehydro-4,5α-epoxy-14β-hydroxy-3-methoxy-6'-methylsulfinyl-6,7,2',3'-indolomorphinan,
17-allyl-6,7-didehydro-4,5α-epoxy-14β-hydroxy-3-methoxy-6'-methylsulfinyl-6,7,2',3'-indolomorphinan,
17-cyclopropylmethyl-6,7-didehydro-4,5α-epoxy-3,14β-dihydroxy-7'-methylsulfinyl-6,7,2',3'-indolomorphinan, 17-allyl-6,7-didehydro-4,5α-epoxy-3,14β-dihydroxy-7'-methylsulfinyl-6,7,2',3'-indolomorphinan, 17-cyclopropylmethyl-6,7-didehydro-4,5α-epoxy-14β-hydroxy-3-methoxy-7'-methylsulfinyl-6,7,2',3'-indolomorphinan, 17-allyl-6,7-didehydro-4,5α-epoxy-14β-hydroxy-3-methoxy-7'-methylsulfinyl-6,7,2',3'-indolomorphinan, 17-cyclopropylmethyl-6,7-didehydro-4,5α-epoxy-3,14β-dihydroxy-4'-sulfamoyl-6,7,2',3'-indolomorphinan, 17-allyl-6,7-didehydro-4,5α-epoxy-3,14β-dihydroxy-4'-sulfamoyl-6,7,2',3'-indolomorphinan, 17-cyclopropylmethyl-6,7-didehydro-4,5α-epoxy-14β-hydroxy-3-methoxy-4'-sulfamoyl-6,7,2',3'-indolomorphinan, 17-allyl-6,7-didehydro-4,5α-epoxy-14β-hydroxy-3-methoxy-4'-sulfamoyl-6,7,2',3'-indolomorphinan, 17-cyclopropylmethyl-6,7-didehydro-4,5α-epoxy-3,14β-dihydroxy-5'-sulfamoyl-6,7,2',3'-indolomorphinan, 17-allyl-6,7-didehydro-4,5α-epoxy-3,14β-dihydroxy-5'-sulfamoyl-6,7,2',3'-indolomorphinan, 17-cyclopropylmethyl-6,7-didehydro-4,5α-epoxy-14β-hydroxy-3-methoxy-5'-sulfamoyl-6,7,2',3'-indolomorphinan, 17-allyl-6,7-didehydro-4,5α-epoxy-14β-hydroxy-3-methoxy-5'-sulfamoyl-6,7,2',3'-indolomorphinan, 17-cyclopropylmethyl-6,7-didehydro-4,5α-epoxy-3,14β-dihydroxy-6'-sulfamoyl-6,7,2',3'-indolomorphinan, 17-allyl-6,7-didehydro-4,5α-epoxy-3,14β-dihydroxy-6'-sulfamoyl-6,7,2',3'-indolomorphinan, 17-cyclopropylmethyl-6,7-didehydro-4,5α-epoxy-14β-hydroxy-3-methoxy-6'-sulfamoyl-6,7,2',3'-indolomorphinan, 17-allyl-6,7-didehydro-4,5α-epoxy-14β-hydroxy-3-methoxy-6'-sulfamoyl-6,7,2',3'-indolomorphinan, 17-cyclopropylmethyl-6,7-didehydro-4,5α-epoxy-3,14β-dihydroxy-7'-sulfamoyl-6,7,2',3'-indolomorphinan, 17-allyl-6,7-didehydro-4,5α-epoxy-3,14β-dihydroxy-7'-sulfamoyl-6,7,2',3'-indolomorphinan, 17-cyclopropylmethyl-6,7-didehydro-4,5α-epoxy-14β-hydroxy-3-methoxy-7'-sulfamoyl-6,7,2',3'-indolomorphinan, 17-allyl-6,7-didehydro-4,5α-epoxy-14β-hydroxy-3-methoxy-7'-sulfamoyl-6,7,2',3'-indolomorphinan, 17-cyclopropylmethyl-6,7-didehydro-4,5α-epoxy-3,14β-dihydroxy-4'-dimethylsulfamoyl-6,7,2',3'-indolomorphinan, 17-allyl-6,7-didehydro-4,5α-epoxy-3,14β-dihydroxy-4'-dimethylsulfamoyl-6,7,2',3'-indolomorphinan, 17-cyclopropylmethyl-6,7-didehydro-4,5α-epoxy-14β-hydroxy-3-methoxy-4'-dimethylsulfamoyl-6,7,2',3'-indolomorphinan, 17-allyl-6,7-didehydro-4,5α-epoxy-14β-hydroxy-3-methoxy-4'-dimethylsulfamoyl-6,7,2',3'-indolomorphinan, 17-cyclopropylmethyl-6,7-didehydro-4,5α-epoxy-3,14β-dihydroxy-5'-dimethylsulfamoyl-6,7,2',3'-indolomorphinan, 17-allyl-6,7-didehydro-4,5α-epoxy-3,14β-dihydroxy-5'-dimethylsulfamoyl-6,7,2',3'-indolomorphinan, 17-cyclopropylmethyl-6,7-didehydro-4,5α-epoxy-14β-hydroxy-3-methoxy-5'-dimethylsulfamoyl-6,7,2',3'-indolomorphinan, 17-allyl-6,7-didehydro-4,5α-epoxy-14β-hydroxy-3-methoxy-5'-dimethylsulfamoyl-6,7,2',3'-indolomorphinan, 17-cyclopropylmethyl-6,7-didehydro-4,5α-epoxy-3,14β-dihydroxy-6'-dimethylsulfamoyl-6,7,2',3'-indolomorphinan, 17-allyl-6,7-didehydro-4,5α-epoxy-3,14β-dihydroxy-6'-dimethylsulfamoyl-6,7,2',3'-indolomorphinan, 17-cyclopropylmethyl-6,7-didehydro-4,5α-epoxy-14β-hydroxy-3-methoxy-6'-dimethylsulfamoyl-6,7,2',3'-indolomorphinan, 17-allyl-6,7-didehydro-4,5α-epoxy-14β-hydroxy-3-methoxy-6'-dimethylsulfamoyl-6,7,2',3'-indolomorphinan, 17-cyclopropylmethyl-6,7-didehydro-4,5α-epoxy-3,14β-dihydroxy-7'-dimethylsulfamoyl-6,7,2',3'-indolomorphinan, 17-allyl-6,7-didehydro-4,5α-epoxy-3,14β-dihydroxy-7'-dimethylsulfamoyl-6,7,2',3'-indolomorphinan, 17-cyclopropylmethyl-6,7-didehydro-4,5α-epoxy-14β-hydroxy-3-methoxy-7'-dimethylsulfamoyl-6,7,2',3'-indolomorphinan, 17-allyl-6,7-didehydro-4,5α-epoxy-14β-hydroxy-3-methoxy-7'-dimethylsulfamoyl-6,7,2',3'-indolomorphinan, 17-cyclopropylmethyl-6,7-didehydro-4,5α-epoxy-3,14β-dihydroxy-4'-cyclopropylmethylsulfamoyl-6,7,2',3'-indolomorphinan, 17-allyl-6,7-didehydro-4,5α-epoxy-3,14β-dihydroxy-4'-cyclopropylmethylsulfamoyl-6,7,2',3'-indolomorphinan, 17-cyclopropylmethyl-6,7-didehydro-4,5α-epoxy-14β-hydroxy-3-methoxy-4'-cyclopropylmethylsulfamoyl-6,7,2',3'-indolomorphinan, 17-allyl-6,7-didehydro-4,5α-epoxy-14β-hydroxy-3-methoxy-4'-cyclopropylmethylsulfamoyl-6,7,2',3'-indolomorphinan, 17-cyclopropylmethyl-6,7-didehydro-4,5α-epoxy-3,14β-dihydroxy-5'-cyclopropylmethylsulfamoyl-6,7,2',3'-indolomorphinan, 17-allyl-6,7-didehydro-4,5α-epoxy-3,14β-dihydroxy-5'-cyclopropylmethylsulfamoyl-6,7,2',3'-indolomorphinan, 17-cyclopropylmethyl-6,7-didehydro-4,5α-epoxy-14β-hydroxy-3-methoxy-5'-cyclopropylmethylsulfamoyl-6,7,2',3'-indolomorphinan, 17-allyl-6,7-didehydro-4,5α-epoxy-14β-hydroxy-3-methoxy-5'-cyclopropylmethylsulfamoyl-6,7,2',3'-indolomorphinan, 17-cyclopropylmethyl-6,7-didehydro-4,5α-epoxy-3,14β-dihydroxy-6'-cyclopropylmethylsulfamoyl-6,7,2',3'-indolomorphinan, 17-allyl-6,7-didehydro-4,5α-epoxy-3,14β-dihydroxy-6'-cyclopropylmethylsulfamoyl-6,7,2',3'-indolomorphinan, 17-cyclopropylmethyl-6,7-didehydro-4,5α-epoxy-14β-hydroxy-3-methoxy-6'-cyclopropylmethylsulfamoyl-6,7,2',3'-indolomorphinan, 17-allyl-6,7-didehydro-4,5α-epoxy-14β-hydroxy-3-methoxy-6'-cyclopropylmethylsulfamoyl-6,7,2',3'-indolomorphinan, 17-cyclopropylmethyl-6,7-didehydro-4,5α-epoxy-3,14β-dihydroxy-7'-cyclopropylmethylsulfamoyl-6,7,2',3'-indolomorphinan, 17-allyl-6,7-didehydro-4,5α-epoxy-3,14β-dihydroxy-7'-cyclopropylmethylsulfamoyl-6,7,2',3'-indolomorphinan, 17-cyclopropylmethyl-6,7-didehydro-4,5α-epoxy-14β-hydroxy-3-methoxy-7'-cyclopropylmethylsulfamoyl-6,7,2',3'-indolomorphinan, 17-allyl-6,7-didehydro-4,5α-epoxy-14β-hydroxy-3-methoxy-7'-cyclopropylmethylsulfamoyl-6,7,2',3'-indolomorphinan, 17-cyclopropylmethyl-6,7-didehydro-4,5α-epoxy-3,14β-dihydroxy-4'-dimethylcarbamoyl-6,7,2',3'-indolomorphinan, 17-allyl-6,7-didehydro-4,5α-epoxy-3,14β-dihydroxy-4'-dimethylcarbamoyl-6,7,2',3'-indolomorphinan, 17-cyclopropylmethyl-6,7-didehydro-4,5α-epoxy-14β-hydroxy-3-methoxy-4'-dimethylcarbamoyl-6,7,2',3'-indolomorphinan, 17-allyl-6,7-didehydro-4,5α-epoxy-14β-hydroxy-3-methoxy-4'-dimethylcarbamoyl-6,7,2',3'-indolomorphinan, 17-cyclopropylmethyl-6,7-didehydro-4,5α-epoxy-3,14β-dihydroxy-5'-dimethylcarbamoyl-6,7,2',3'-indolomorphinan, 17-allyl-6,7-didehydro-4,5α-epoxy-3,14β-dihydroxy-5'-dimethylcarbamoyl-6,7,2',3'-indolomorphinan, 17-cyclopropylmethyl-6,7-didehydro-4,5α-epoxy-14β-hydroxy-3-methoxy-5'-dimethylcarbamoyl-6,7,2',3'-indolomorphinan, 17-allyl-6,7-didehydro-4,5α-epoxy-14β-hydroxy-3-methoxy-5'-dimethylcarbamoyl-6,7,2',3'-indolomorphinan, 17-cyclopropylmethyl-6,7-didehydro-4,5α-epoxy-3,14β-dihydroxy-6'-dimethylcarbamoyl-6,7,2',3'-indolomorphinan, 17-allyl-6,7-didehydro-4,5α-epoxy-3,14β-dihydroxy-6'-dimethylcarbamoyl-6,7,2',3'-indolomorphinan, 17-cyclopropylmethyl-6,7-didehydro-4,5α-epoxy-14β-hydroxy-3-methoxy-6'-dimethylcarbamoyl-6,7,2',3'-indolomorphinan, 17-allyl-6,7-didehydro-4,5α-epoxy-14β-hydroxy-3-methoxy-6'-dimethylcarbamoyl-6,7,2',3'-indolomorphinan, 17-cyclopropylmethyl-6,7-didehydro-4,5α-epoxy-3,14β-dihydroxy-7'-dimethylcarbamoyl-6,7,2',3'-indolomorphinan, 17-allyl-6,7-didehydro-4,5α-epoxy-3,14β-dihydroxy-7'-dimethylcarbamoyl-6,7,2',3'-indolomorphinan, 17-cyclopropylmethyl-6,7-didehydro-4,5α-epoxy-14β-hydroxy-3-methoxy-7'-dimethylcarbamoyl-6,7,2',3'-indolomorphinan, 17-allyl-6,7-didehydro-4,5α-epoxy-14β-hydroxy-3-methoxy-7'-dimethylcarbamoyl-6,7,2',3'-indolomorphinan, 17-cyclopropylmethyl-6,7-didehydro-4,5α-epoxy-3,14β-dihydroxy-4'-cyclopropylmethylcarbamoyl-6,7,2',3'-indolomorphinan, 17-allyl-6,7-didehydro-4,5α-epoxy-3,14β-dihydroxy-4'-cyclopropylmethylcarbamoyl-6,7,2',3'-indolomorphinan, 17-cyclopropylmethyl-6,7-didehydro-4,5α-epoxy-14β-hydroxy-3-methoxy-4'-cyclopropylmethylcarbamoyl-6,7,2',3'-indolomorphinan, 17-allyl-6,7-didehydro-4,5α-epoxy-14β-hydroxy-3-methoxy-4'-cyclopropylmethylcarbamoyl-6,7,2',3'-indolomorphinan, 17-cyclopropylmethyl-6,7-didehydro-4,5α-epoxy-3,14β-dihydroxy-5'-cyclopropylmethylcarbamoyl-6,7,2',3'-indolomorphinan, 17-allyl-6,7-didehydro-4,5α-epoxy-3,14β-dihydroxy-5'-cyclopropylmethylcarbamoyl-6,7,2',3'-indolomorphinan, 17-cyclopropylmethyl-6,7-didehydro-4,5α-epoxy-14β-hydroxy-3-methoxy-5'-cyclopropylmethylcarbamoyl-6,7,2',3'-indolomorphinan, 17-allyl-6,7-didehydro-4,5α-epoxy-14β-hydroxy-3-methoxy-5'-cyclopropylmethylcarbamoyl-6,7,2',3'-indolomorphinan, 17-cyclopropylmethyl-6,7-didehydro-4,5α-epoxy-3,14β-dihydroxy-6'-cyclopropylmethylcarbamoyl-6,7,2',3'-indolomorphinan, 17-allyl-6,7-didehydro-4,5α-epoxy-3,14β-dihydroxy-6'-cyclopropylmethylcarbamoyl-6,7,2',3'-indolomorphinan, 17-cyclopropylmethyl-6,7-didehydro-4,5α-epoxy-14β-hydroxy-3-methoxy-6'-cyclopropylmethylcarbamoyl-6,7,2',3'-indolomorphinan, 17-allyl-6,7-didehydro-4,5α-epoxy-14β-hydroxy-3-methoxy-6'-cyclopropylmethylcarbamoyl-6,7,2',3'-indolomorphinan, 17-cyclopropylmethyl-6,7-didehydro-4,5α-epoxy-3,14β-dihydroxy-7'-cyclopropylmethylcarbamoyl-6,7,2',3'-indolomorphinan, 17-allyl-6,7-didehydro-4,5α-epoxy-3,14β-dihydroxy-7'-cyclopropylmethylcarbamoyl-6,7,2',3'-indolomorphinan, 17-cyclopropylmethyl-6,7-didehydro-4,5α-epoxy-14β-hydroxy-3-methoxy-7'-cyclopropylmethylcarbamoyl-6,7,2',3'-indolomorphinan, 17-allyl-6,7-didehydro-4,5α-epoxy-14β-hydroxy-3-methoxy-7'-cyclopropylmethylcarbamoyl-6,7,2',3'-indolomorphinan, 17-cyclopropylmethyl-6,7-didehydro-4,5α-epoxy-3,14β-dihydroxy-4'-hydroxymethyl-6,7,2',3'-indolomorphinan, 17-allyl-6,7-didehydro-4,5α-epoxy-3,14β-dihydroxy-4'-hydroxymethyl-6,7,2',3'-indolomorphinan, 17-cyclopropylmethyl-6,7-didehydro-4,5α-epoxy-14β-hydroxy-3-methoxy-4'-hydroxymethyl-6,7,2',3'-indolomorphinan, 17-allyl-6,7-didehydro-4,5α-epoxy-14β-hydroxy-3-methoxy-4'-hydroxymethyl-6,7,2',3'-indolomorphinan, 17-cyclopropylmethyl-6,7-didehydro-4,5α-epoxy-3,14β-dihydroxy-5'-hydroxymethyl-6,7,2',3'-indolomorphinan, 17-allyl-6,7-didehydro-4,5α-epoxy-3,14β-dihydroxy-5'-hydroxymethyl-6,7,2',3'-indolomorphinan, 17-cyclopropylmethyl-6,7-didehydro-4,5α-epoxy-14β-hydroxy-3-methoxy-5'-hydroxymethyl-6,7,2',3'-indolomorphinan, 17-allyl-6,7-didehydro-4,5α-epoxy-14β-hydroxy-3-methoxy-5'-hydroxymethyl-6,7,2',3'-indolomorphinan, 17-cyclopropylmethyl-6,7-didehydro-4,5α-epoxy-3,14β-dihydroxy-6'-hydroxymethyl-6,7,2',3'-indolomorphinan, 17-allyl-6,7-didehydro-4,5α-epoxy-3,14β-dihydroxy-6'-hydroxymethyl-6,7,2',3'-indolomorphinan, 17-cyclopropylmethyl-6,7-didehydro-4,5α-epoxy-14β-hydroxy-3-methoxy-6'-hydroxymethyl-6,7,2',3'-indolomorphinan, 17-allyl-6,7-didehydro-4,5α-epoxy-14β-hydroxy-3-methoxy-6'-hydroxymethyl-6,7,2',3'-indolomorphinan, 17-cyclopropylmethyl-6,7-didehydro-4,5α-epoxy-3,14β-dihydroxy-7'-hydroxymethyl-6,7,2',3'-indolomorphinan, 17-allyl-6,7-didehydro-4,5α-epoxy-3,14β-dihydroxy-7'-hydroxymethyl-6,7,2',3'-indolomorphinan, 17-cyclopropylmethyl-6,7-didehydro-4,5α-epoxy-14β-hydroxy-3-methoxy-7'-hydroxymethyl-6,7,2',3'-indolomorphinan, 17-allyl-6,7-didehydro-4,5α-epoxy-14β-hydroxy-3-methoxy-7'-hydroxymethyl-6,7,2',3'-indolomorphinan, 17-cyclopropylmethyl-6,7-didehydro-4,5α-epoxy-3,14β-dihydroxy-4'-hydroxyethyl-6,7,2',3'-indolomorphinan, 17-allyl-6,7-didehydro-4,5α-epoxy-3,14β-dihydroxy-4'-hydroxyethyl-6,7,2',3'-indolomorphinan, 17-cyclopropylmethyl-6,7-didehydro-4,5α-epoxy-14β-hydroxy-3-methoxy-4'-hydroxyethyl-6,7,2',3'-indolomorphinan, 17-allyl-6,7-didehydro-4,5α-epoxy-14β-hydroxy-3-methoxy-4'-hydroxyethyl-6,7,2',3'-indolomorphinan, 17-cyclopropylmethyl-6,7-didehydro-4,5α-epoxy-3,14β-dihydroxy-5'-hydroxyethyl-6,7,2',3'-indolomorphinan, 17-allyl-6,7-didehydro-4,5α-epoxy-3,14β-dihydroxy-5'-hydroxyethyl-6,7,2',3'-indolomorphinan, 17-cyclopropylmethyl-6,7-didehydro-4,5α-epoxy-14β-hydroxy-3-methoxy-5'-hydroxyethyl-6,7,2',3'-indolomorphinan, 17-allyl-6,7-didehydro-4,5α-epoxy-14β-hydroxy-3-methoxy-5'-hydroxyethyl-6,7,2',3'-indolomorphinan, 17-cyclopropylmethyl-6,7-didehydro-4,5α-epoxy-3,14β-dihydroxy-6'-hydroxyethyl-6,7,2',3'-indolomorphinan, 17-allyl-6,7-didehydro-4,5α-epoxy-3,14β-dihydroxy-6'-hydroxyethyl-6,7,2',3'-indolomorphinan, 17-cyclopropylmethyl-6,7-didehydro-4,5α-epoxy-14β-hydroxy-3-methoxy-6'-hydroxyethyl-6,7,2',3'-indolomorphinan, 17-allyl-6,7-didehydro-4,5α-epoxy-14β-hydroxy-3-methoxy-6'-hydroxyethyl-6,7,2',3'-indolomorphinan, 17-cyclopropylmethyl-6,7-didehydro-4,5α-epoxy-3,14β-dihydroxy-7'-hydroxyethyl-6,7,2',3'-indolomorphinan, 17-allyl-6,7-didehydro-4,5α-epoxy-3,14β-dihydroxy-7'-hydroxyethyl-6,7,2',3'-indolomorphinan, 17-cyclopropylmethyl-6,7-didehydro-4,5α-epoxy-14β-hydroxy-3-methoxy-7'-hydroxyethyl-6,7,2',3'-indolomorphinan, 17-allyl-6,7-didehydro-4,5α-epoxy-14β-hydroxy-3-methoxy-7'-hydroxyethyl-6,7,2',3'-indolomorphinan, 17-cyclopropylmethyl-6,7-didehydro-4,5α-epoxy-3,14β-dihydroxy-4'-methoxycarbonylmethyl-6,7,2',3'-indolomorphinan, 17-allyl-6,7-didehydro-4,5α-epoxy-3,14β-dihydroxy-4'-methoxycarbonylmethyl-6,7,2',3'-indolomorphinan, 17-cyclopropylmethyl-6,7-didehydro-4,5α-epoxy-14β-hydroxy-3-methoxy-4'-methoxycarbonylmethyl-6,7,2',3'-indolomorphinan, 17-allyl-6,7-didehydro-4,5α-epoxy-14β-hydroxy-3-methoxy-4'-methoxycarbonylmethyl-6,7,2',3'-indolomorphinan, 17-cyclopropylmethyl-6,7-didehydro-4,5α-epoxy-3,14β-dihydroxy-5'-methoxycarbonylmethyl-6,7,2',3'-indolomorphinan, 17-allyl-6,7-didehydro-4,5α-epoxy-3,14β-dihydroxy-5'-methoxycarbonylmethyl-6,7,2',3'-indolomorphinan, 17-cyclopropylmethyl-6,7-didehydro-4,5α-epoxy-14β-hydroxy-3-methoxy-5'-methoxycarbonylmethyl-6,7,2',3'-indolomorphinan, 17-allyl-6,7-didehydro-4,5α-epoxy-14β-hydroxy-3-methoxy-5'-methoxycarbonylmethyl-6,7,2',3'-indolomorphinan, 17-cyclopropylmethyl-6,7-didehydro-4,5α-epoxy-3,14β-dihydroxy-6'-methoxycarbonylmethyl-6,7,2',3'-indolomorphinan, 17-allyl-6,7-didehydro-4,5α-epoxy-3,14β-dihydroxy-6'-methoxycarbonylmethyl-6,7,2',3'-indolomorphinan, 17-cyclopropylmethyl-6,7-didehydro-4,5α-epoxy-14β-hydroxy-3-methoxy-6'-methoxycarbonylmethyl-6,7,2',3'-indolomorphinan, 17-allyl-6,7-didehydro-4,5α-epoxy-14β-hydroxy-3-methoxy-6'-methoxycarbonylmethyl-6,7,2',3'-indolomorphinan, 17-cyclopropylmethyl-6,7-didehydro-4,5α-epoxy-3,14β-dihydroxy-7'-methoxycarbonylmethyl-6,7,2',3'-indolomorphinan, 17-allyl-6,7-didehydro-4,5α-epoxy-3,14β-dihydroxy-7'-methoxycarbonylmethyl-6,7,2',3'-indolomorphinan, 17-cyclopropylmethyl-6,7-didehydro-4,5α-epoxy-14β-hydroxy-3-methoxy-7'-methoxycarbonylmethyl-6,7,2',3'-indolomorphinan, 17-allyl-6,7-didehydro-4,5α-epoxy-14β-hydroxy-3-methoxy-7'-methoxycarbonylmethyl-6,7,2',3'-indolomorphinan, 17-cyclopropylmethyl-6,7-didehydro-4,5α-epoxy-3,14β-dihydroxy-4'-methoxycarbonylethyl-6,7,2',3'-indolomorphinan, 17-allyl-6,7-didehydro-4,5α-epoxy-3,14β-dihydroxy-4'-methoxycarbonylethyl-6,7,2',3'-indolomorphinan, 17-cyclopropylmethyl-6,7-didehydro-4,5α-epoxy-14β-hydroxy-3-methoxy-4'-methoxycarbonylethyl-6,7,2',3'-indolomorphinan, 17-allyl-6,7-didehydro-4,5α-epoxy-14β-hydroxy-3-methoxy-4'-methoxycarbonylethyl-6,7,2',3'-indolomorphinan, 17-cyclopropylmethyl-6,7-didehydro-4,5α-epoxy-3,14β-dihydroxy-5'-methoxycarbonylethyl-6,7,2',3'-indolomorphinan, 17-allyl-6,7-didehydro-4,5α-epoxy-3,14β-dihydroxy-5'-methoxycarbonylethyl-6,7,2',3'-indolomorphinan, 17-cyclopropylmethyl-6,7-didehydro-4,5α-epoxy-14β-hydroxy-3-methoxy-5'-methoxycarbonylethyl-6,7,2',3'-indolomorphinan, 17-allyl-6,7-didehydro-4,5α-epoxy-14β-hydroxy-3-methoxy-5'-methoxycarbonylethyl-6,7,2',3'-indolomorphinan, 17-cyclopropylmethyl-6,7-didehydro-4,5α-epoxy-3,14β-dihydroxy-6'-methoxycarbonylethyl-6,7,2',3'-indolomorphinan, 17-allyl-6,7-didehydro-4,5α-epoxy-3,14β-dihydroxy-6'-methoxycarbonylethyl-6,7,2',3'-indolomorphinan, 17-cyclopropylmethyl-6,7-didehydro-4,5α-epoxy-14β-hydroxy-3-methoxy-6'-methoxycarbonylethyl-6,7,2',3'-indolomorphinan, 17-allyl-6,7-didehydro-4,5α-epoxy-14β-hydroxy-3-methoxy-6'-methoxycarbonylethyl-6,7,2',3'-indolomorphinan, 17-cyclopropylmethyl-6,7-didehydro-4,5α-epoxy-3,14β-dihydroxy-7'-methoxycarbonylethyl-6,7,2',3'-indolomorphinan, 17-allyl-6,7-didehydro-4,5α-epoxy-3,14β-dihydroxy-7'-methoxycarbonylethyl-6,7,2',3'-indolomorphinan, 17-cyclopropylmethyl-6,7-didehydro-4,5α-epoxy-14β-hydroxy-3-methoxy-7'-methoxycarbonylethyl-6,7,2',3'-indolomorphinan, 17-allyl-6,7-didehydro-4,5α-epoxy-14β-hydroxy-3-methoxy-7'-methoxycarbonylethyl-6,7,2',3'-indolomorphinan, 17-cyclopropylmethyl-6,7-didehydro-4,5α-epoxy-3,14β-dihydroxy-4'-dimethylaminomethyl-6,7,2',3'-indolomorphinan, 17-allyl-6,7-didehydro-4,5α-epoxy-3,14β-dihydroxy-4'-dimethylaminomethyl-6,7,2',3'-indolomorphinan, 17-cyclopropylmethyl-6,7-didehydro-4,5α-epoxy-14β-hydroxy-3-methoxy-4'-dimethylaminomethyl-6,7,2',3'-indolomorphinan, 17-allyl-6,7-didehydro-4,5α-epoxy-14β-hydroxy-3-methoxy-4'-dimethylaminomethyl-6,7,2',3'-indolomorphinan, 17-cyclopropylmethyl-6,7-didehydro-4,5α-epoxy-3,14β-dihydroxy-5'-dimethylaminomethyl-6,7,2',3'-indolomorphinan, 17-allyl-6,7-didehydro-4,5α-epoxy-3,14β-dihydroxy-5'-dimethylaminomethyl-6,7,2',3'-indolomorphinan, 17-cyclopropylmethyl-6,7-didehydro-4,5α-epoxy-14β-hydroxy-3-methoxy-5'-dimethylaminomethyl-6,7,2',3'-indolomorphinan, 17-allyl-6,7-didehydro-4,5α-epoxy-14β-hydroxy-3-methoxy-5'-dimethylaminomethyl-6,7,2',3'-indolomorphinan, 17-cyclopropylmethyl-6,7-didehydro-4,5α-epoxy-3,14β-dihydroxy-6'-dimethylaminomethyl-6,7,2',3'-indolomorphinan, 17-allyl-6,7-didehydro-4,5α-epoxy-3,14β-dihydroxy-6'-dimethylaminomethyl-6,7,2',3'-indolomorphinan, 17-cyclopropylmethyl-6,7-didehydro-4,5α-epoxy-14β-hydroxy-3-methoxy-6'-dimethylaminomethyl-6,7,2',3'-indolomorphinan, 17-allyl-6,7-didehydro-4,5α-epoxy-14β-hydroxy-3-methoxy-6'-dimethylaminomethyl-6,7,2',3'-indolomorphinan, 17-cyclopropylmethyl-6,7-didehydro-4,5α-epoxy-3,14β-dihydroxy-7'-dimethylaminomethyl-6,7,2',3'-indolomorphinan, 17-allyl-6,7-didehydro-4,5α-epoxy-3,14β-dihydroxy-7'-dimethylaminomethyl-6,7,2',3'-indolomorphinan, 17-cyclopropylmethyl-6,7-didehydro-4,5α-epoxy-14β-hydroxy-3-methoxy-7'-dimethylaminomethyl-6,7,2',3'-indolomorphinan, 17-allyl-6,7-didehydro-4,5α-epoxy-14β-hydroxy-3-methoxy-7'-dimethylaminomethyl-6,7,2',3'-indolomorphinan, 17-cyclopropylmethyl-6,7-didehydro-4,5α-epoxy-3,14β-dihydroxy-4'-dimethylaminoethyl-6,7,2',3'-indolomorphinan, 17-allyl-6,7-didehydro-4,5α-epoxy-3,14β-dihydroxy-4'-dimethylaminoethyl-6,7,2',3'-indolomorphinan, 17-cyclopropylmethyl-6,7-didehydro-4,5α-epoxy-14β-hydroxy-3-methoxy-4'-dimethylaminoethyl-6,7,2',3'-indolomorphinan, 17-allyl-6,7-didehydro-4,5α-epoxy-14β-hydroxy-3-methoxy-4'-dimethylaminoethyl-6,7,2',3'-indolomorphinan, 17-cyclopropylmethyl-6,7-didehydro-4,5α-epoxy-3,14β-dihydroxy-5'-dimethylaminoethyl-6,7,2',3'-indolomorphinan, 17-allyl-6,7-didehydro-4,5α-epoxy-3,14β-dihydroxy-5'-dimethylaminoethyl-6,7,2',3'-indolomorphinan, 17-cyclopropylmethyl-6,7-didehydro-4,5α-epoxy-14β-hydroxy-3-methoxy-5'-dimethylaminoethyl-6,7,2',3'-indolomorphinan, 17-allyl-6,7-didehydro-4,5α-epoxy-14β-hydroxy-3-methoxy-5'-dimethylaminoethyl-6,7,2',3'-indolomorphinan, 17-cyclopropylmethyl-6,7-didehydro-4,5α-epoxy-3,14β-dihydroxy-6'-dimethylaminoethyl-6,7,2',3'-indolomorphinan, 17-allyl-6,7-didehydro-4,5α-epoxy-3,14β-dihydroxy-6'-dimethylaminoethyl-6,7,2',3'-indolomorphinan, 17-cyclopropylmethyl-6,7-didehydro-4,5α-epoxy-14β-hydroxy-3-methoxy-6'-dimethylaminoethyl-6,7,2',3'-indolomorphinan, 17-allyl-6,7-didehydro-4,5α-epoxy-14β-hydroxy-3-methoxy-6'-dimethylaminoethyl-6,7,2',3'-indolomorphinan, 17-cyclopropylmethyl-6,7-didehydro-4,5α-epoxy-3,14β-dihydroxy-7'-dimethylaminoethyl-6,7,2',3'-indolomorphinan, 17-allyl-6,7-didehydro-4,5α-epoxy-3,14β-dihydroxy-7'-dimethylaminoethyl-6,7,2',3'-indolomorphinan, 17-cyclopropylmethyl-6,7-didehydro-4,5α-epoxy-14β-hydroxy-3-methoxy-7'-dimethylaminoethyl-6,7,2',3'-indolomorphinan, 17-allyl-6,7-didehydro-4,5α-epoxy-14β-hydroxy-3-methoxy-7'-dimethylaminoethyl-6,7,2',3'-indolomorphinan, 17-cyclopropylmethyl-6,7-didehydro-4,5α-epoxy-3,14β-dihydroxy-4'-cyclopropylmethylaminomethyl-6,7,2',3'-indolomorphinan, 17-allyl-6,7-didehydro-4,5α-epoxy-3,14β-dihydroxy-4'-cyclopropylmethylaminomethyl-6,7,2',3'-indolomorphinan, 17-cyclopropylmethyl-6,7-didehydro-4,5α-epoxy-14β-hydroxy-3-methoxy-4'-cyclopropylmethylaminomethyl-6,7,2',3'-indolomorphinan, 17-allyl-6,7-didehydro-4,5α-epoxy-14β-hydroxy-3-methoxy-4'-cyclopropylmethylaminomethyl-6,7,2',3'-indolomorphinan, 17-cyclopropylmethyl-6,7-didehydro-4,5α-epoxy-3,14β-dihydroxy-5'-cyclopropylmethylaminomethyl-6,7,2',3'-indolomorphinan, 17-allyl-6,7-didehydro-4,5α-epoxy-3,14β-dihydroxy-5'-cyclopropylmethylaminomethyl-6,7,2',3'-indolomorphinan, 17-cyclopropylmethyl-6,7-didehydro-4,5α-epoxy-14β-hydroxy-3-methoxy-5'-cyclopropylmethylaminomethyl-6,7,2',3'-indolomorphinan, 17-allyl-6,7-didehydro-4,5α-epoxy-14β-hydroxy-3-methoxy-5'-cyclopropylmethylaminomethyl-6,7,2',3'-indolomorphinan, 17-cyclopropylmethyl-6,7-didehydro-4,5α-epoxy-3,14β-dihydroxy-6'-cyclopropylmethylaminomethyl-6,7,2',3'-indolomorphinan, 17-allyl-6,7-didehydro-4,5α-epoxy-3,14β-dihydroxy-6'-cyclopropylmethylaminomethyl-6,7,2',3'-indolomorphinan, 17-cyclopropylmethyl-6,7-didehydro-4,5α-epoxy-14β-hydroxy-3-methoxy-6'-cyclopropylmethylaminomethyl-6,7,2',3'-indolomorphinan, 17-allyl-6,7-didehydro-4,5α-epoxy-14β-hydroxy-3-methoxy-6'-cyclopropylmethylaminomethyl-6,7,2',3'-indolomorphinan, 17-cyclopropylmethyl-6,7-didehydro-4,5α-epoxy-3,14β-dihydroxy-7'-cyclopropylmethylaminomethyl-6,7,2',3'-indolomorphinan, 17-allyl-6,7-didehydro-4,5α-epoxy-3,14β-dihydroxy-7'-cyclopropylmethylaminomethyl-6,7,2',3'-indolomorphinan, 17-cyclopropylmethyl-6,7-didehydro-4,5α-epoxy-14β-hydroxy-3-methoxy-7'-cyclopropylmethylaminomethyl-6,7,2',3'-indolomorphinan and 17-allyl-6,7-didehydro-4,5α-epoxy-14β-hydroxy-3-methoxy-7'-cyclopropylmethylaminomethyl-6,7,2',3'-indolomorphinan.

Among the compounds represented by formula (II), the compound wherein $R^1$ is cyclopropylmethyl, $R^2$ and $R^3$ are hydroxy, $R^4$ and $R^7$ are hydrogen, Z is —$(CH_2)_4$— which is bound to 6'- and 7'-positions, that is, Compound 2 of the formula:

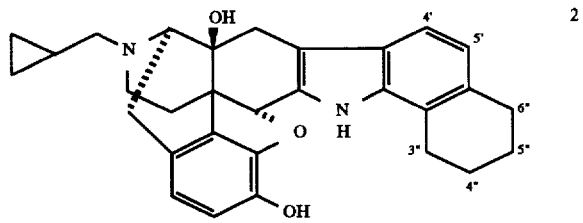

is named 17-cyclopropylmethyl-6,7-didehydro-4,5α-epoxy-3,14β-dihydroxy-6',7'-cyclohexeno-6,7,2',3'-indolomorphinan.

According to this nomenclature, specific examples of the compounds employed in the present invention include 17-allyl-6,7-didehydro-4,5α-epoxy-3,14β-dihydroxy-6',7'-cyclohexeno-6,7,2',3'-indolomorphinan, 17-cyclopropylmethyl-6,7-didehydro-4,5α-epoxy-14β-hydroxy-3-methoxy-6',7'-cyclohexeno-6,7,2'3'-indolomorphinan, 17-allyl-6,7-didehydro-4,5α-epoxy-14β-hydroxy-3-methoxy-6',7'-cyclohexeno-6,7,2',3'-indolomorphinan, 17-cyclopropylmethyl-6,7-didehydro-4,5α-epoxy-3,14β-dihydroxy-5',6'-cyclohexeno-6,7,2',3'-indolomorphinan, 17-allyl-6,7-didehydro-4,5α-epoxy-3,14β-dihydroxy-5',6'-cyclohexeno-6,7,2',3'-indolomorphinan, 17-cyclopropylmethyl-6,7-didehydro-4,5α-epoxy-14β-hydroxy-3-methoxy-5',6'-cyclohexeno-6,7,2',3'-indolomorphinan, 17-allyl-6,7-didehydro-4,5α-epoxy-14β-hydroxy-3-methoxy-5',6'-cyclohexeno-6,7,2',3'-indolomorphinan, 17-cyclopropylmethyl-6,7-didehydro-4,5α-epoxy-3,14β-dihydroxy-4',5'-cyclohexeno-6,7,2',3'-indolomorphinan, 17-allyl-6,7-didehydro-4,5α-epoxy-3,14β-dihydroxy-4',5'-cyclohexeno-6,7,2',3'-indolomorphinan, 17-cyclopropylmethyl-6,7-didehydro-4,5α-epoxy-14β-hydroxy-3-methoxy-4',5'-cyclohexeno-6,7,2',3'-indolomorphinan, 17-allyl-6,7-didehydro-4,5α-epoxy-14β-hydroxy-3-methoxy-4',5'-cyclohexeno-6,7,2',3'-indolomorphinan, 17-cyclopropylmethyl-6,7-didehydro-4,5α-epoxy-3,14β-dihydroxy-6',7'-cyclopenteno-6,7,2',3'-indolomorphinan, 17-allyl-6,7-didehydro-4,5α-epoxy-3,14β-dihydroxy-6',7'-cyclopenteno-6,7,2',3'-indolomorphinan, 17-cyclopropylmethyl-6,7-didehydro-4,5α-epoxy-14β-hydroxy-3-methoxy-6',7'-cyclopenteno-6,7,2',3'-indolomorphinan, 17-allyl-6,7-didehydro-4,5α-epoxy-14β-hydroxy-3-methoxy-6',7'-cyclopenteno-6,7,2',3'-indolomorphinan, 17-cyclopropylmethyl-6,7-didehydro-4,5α-epoxy-3,14β-dihydroxy-5',6'-cyclopenteno-6,7,2',3'-indolomorphinan, 17-allyl-6,7-didehydro-4,5α-epoxy-3,14β-dihydroxy-5',6'-cyclopenteno-6,7,2',3'-indolomorphinan, 17-cyclopropylmethyl-6,7-didehydro-4,5α-epoxy-14β-hydroxy-3-methoxy-5',6'-cyclopenteno-6,7,2',3'-indolomorphinan, 17-allyl-6,7-didehydro-4,5α-epoxy-14β-hydroxy-3-methoxy-5',6'-cyclopenteno-6,7,2',3'-indolomorphinan, 17-cyclopropylmethyl-6,7-didehydro-4,5α-epoxy-3,14β-dihydroxy-4',5'-cyclopenteno-6,7,2',3'-indolomorphinan, 17-allyl-6,7-didehydro-4,5α-epoxy-3,14β-dihydroxy-4',5'-cyclopenteno-6,7,2',3'-indolomorphinan, 17-cyclopropylmethyl-6,7-didehydro-4,5α-epoxy-14β-hydroxy-3-methoxy-4',5'-cyclopenteno-6,7,2',3'-indolomorphinan, 17-allyl-6,7-didehydro-4,5α-epoxy-14β-hydroxy-3-methoxy-4',5'-cyclopenteno-6,7,2',3'-indolomorphinan, 17-cyclopropylmethyl-6,7-didehydro-4,5α-epoxy-3,14β-dihydroxy-6',7'-cyclohepteno-6,7,2',3'-indolomorphinan, 17-allyl-6,7-didehydro-4,5α-epoxy-3,14β-dihydroxy-6',7'-cyclohepteno-6,7,2',3'-indolomorphinan, 17-cyclopropylmethyl-6,7-didehydro-4,5α-epoxy-14β-hydroxy-3-methoxy-6',7'-cyclohepteno-6,7,2',3'-indolomorphinan, 17-allyl-6,7-didehydro-4,5α-epoxy-14β-hydroxy-3-methoxy-6',7'-cyclohepteno-6,7,2',3'-indolomorphinan, 17-cyclopropylmethyl-6,7-didehydro-4,5α-epoxy-3,14β-dihydroxy-5',6'-cyclohepteno-6,7,2',3'-indolomorphinan, 17-allyl-6,7-didehydro-4,5α-epoxy-3,14β-dihydroxy-5',6'-cyclohepteno-6,7,2',3'-indolomorphinan, 17-cyclopropylmethyl-6,7-didehydro-4,5α-epoxy-14β-hydroxy-3-methoxy-5',6'-cyclohepteno-6,7,2',3'-indolomorphinan, 17-allyl-6,7-didehydro-4,5α-epoxy-14β-hydroxy-3-methoxy-5',6'-cyclohepteno-6,7,2',3'-indolomorphinan, 17-cyclopropylmethyl-6,7-didehydro-4,5α-epoxy-3,14β-dihydroxy-4',5'-cyclohepteno-6,7,2',3'-indolomorphinan, 17-allyl-6,7-didehydro-4,5α-epoxy-3,14β-dihydroxy-4',5'-cyclohepteno-6,7,2',3'-indolomorphinan, 17-cyclopropylmethyl-6,7-didehydro-4,5α-epoxy-14β-hydroxy-3-methoxy-4',5'-cyclohepteno-6,7,2',3'-indolomorphinan, 17-allyl-6,7-didehydro-4,5α-epoxy-14β-hydroxy-3-methoxy-4',5'-cyclohepteno-6,7,2',3'-indolomorphinan, 17-cyclopropylmethyl-6,7-didehydro-4,5α-epoxy-3,14β-dihydroxy-6',7'-benzo-6,7,2',3'-indolomorphinan, 17-allyl-6,7-didehydro-4,5α-epoxy-3,14β-dihydroxy-6',7'-benzo-6,7,2',3'-indolomorphinan, 17-cyclopropylmethyl-6,7-didehydro-4,5α-epoxy-14β-hydroxy-3-methoxy-6',7'-benzo-6,7,2',3'-indolomorphinan, 17-allyl-6,7-didehydro-4,5α-epoxy-14β-hydroxy-3-methoxy-6',7'-benzo-6,7,2',3'-indolomorphinan, 17-cyclopropylmethyl-6,7-didehydro-4,5α-epoxy-3,14β-dihydroxy-5',6'-benzo-6,7,2',3'-indolomorphinan, 17-allyl-6,7-didehydro-4,5α-epoxy-3,14β-dihydroxy-5',6'-benzo-6,7,2',3'-indolomorphinan, 17-cyclopropylmethyl-6,7-didehydro-4,5α-epoxy-14β-hydroxy-3-methoxy-5',6'-benzo-6,7,2',3'-indolomorphinan, 17-allyl-6,7-didehydro-4,5α-epoxy-14β-hydroxy-3-methoxy-5',6'-benzo-6,7,2',3'-indolomorphinan, 17-cyclopropylmethyl-6,7-didehydro-4,5α-epoxy-3,14β-dihydroxy-4',5'-benzo-6,7,2°,3'-indolomorphinan, 17-allyl-6,7-didehydro-4,5α-epoxy-3,14β-dihydroxy-4',5'-benzo-6,7,2',3'-indolomorphinan, 17-cyclopropylmethyl-6,7-didehydro-4,5α-epoxy-14β-hydroxy-3-methoxy-4',5'-benzo-6,7,2',3'-indolomorphinan, 17-allyl-6,7-didehydro-4,5α-epoxy-14β-hydroxy-3-methoxy-4',5'-benzo-6,7,2',3'-indolomorphinan, 17-cyclopropylmethyl-6,7-didehydro-4,5α-epoxy-3,14β-dihydroxy-[6',7'-b]-pyrido-6,7,2',3'-indolomorphinan, 17-allyl-6,7-didehydro-4,5α-epoxy-3,14β-dihydroxy-[6',7'-b]-pyrido-6,7,2',3'-indolomorphinan, 17-cyclopropylmethyl-6,7-didehydro-4,5α-epoxy-14β-hydroxy-3-methoxy-[6',7'-b]-pyrido-6,7,2',3'-indolomorphinan, 17-allyl-6,7-didehydro-4,5α-epoxy-14β-hydroxy-3-methoxy-[6',7'-b]-pyrido-6,7,2',3'-indolomorphinan, 17-cyclopropylmethyl-6,7-didehydro-4,5α-epoxy-3,14β-dihydroxy-[5',6'-b]-pyrido-6,7,2',3'-indolomorphinan, 17-allyl-6,7-didehydro-4,5α-epoxy-3,14β-dihydroxy-[5',6'-b]-pyrido-6,7,2',3'-indolomorphinan, 17-cyclopropylmethyl-6,7-didehydro-4,5α-epoxy-14β-hydroxy-3-methoxy-[5',6'-b]-pyrido-6,7,2',3'-indolomorphinan, 17-allyl-6,7-didehydro-4,5α-epoxy-14β-hydroxy-3-methoxy-[5',6'-b]-pyrido-6,7,2',3'-indolomorphinan, 17-cyclopropylmethyl-6,7-didehydro-4,5α-epoxy-3,14β-dihydroxy-[4',5'-b]-pyrido-6,7,2',3'-indolomorphinan, 17-allyl-6,7-didehydro-4,5α-epoxy-3,14β-dihydroxy-[4',5'-b]-pyrido-6,7,2',3'-indolomorphinan, 17-cyclopropylmethyl-6,7-didehydro-4,5α-epoxy-14β-hydroxy-3-methoxy-[4',5'-b]-pyrido-6,7,2',3'-indolomorphinan, 17-allyl-6,7-didehydro-4,5α-epoxy-14β-hydroxy-3-methoxy-[4',5'-b]-pyrido-6,7,2',3'-indolomorphinan, 17-cyclopropylmethyl-6,7-didehydro-4,5α-epoxy-3,14β-dihydroxy-[6',7'-c]-pyrido-6,7,2',3'-indolomorphinan, 17-allyl-6,7-didehydro-4,5α-epoxy-3,14β-dihydroxy-[6',7'-c]-pyrido-6,7,2',3'-indolomorphinan, 17-cyclopropylmethyl-6,7-didehydro-4,5α-epoxy-14β-hydroxy-3-methoxy-[6',7'-c]-pyrido-6,7,2',3'-indolomorphinan, 17-allyl-6,7-didehydro-4,5α-epoxy-14β-hydroxy-3-methoxy-[6',7'-c]-pyrido-6,7,2',3'-indolomorphinan, 17-cyclopropylmethyl-6,7-didehydro-4,5α-epoxy-3,14β-dihydroxy-[5',6'-c]-pyrido-6,7,2',3'-indolomorphinan, 17-allyl-6,7-didehydro-4,5α-epoxy-3,14β-dihydroxy-[5',6'-c]-pyrido-6,7,2',3'-indolomorphinan,
17-cyclopropylmethyl-6,7-didehydro-4,5α-epoxy-14β-hydroxy-3-methoxy-[5',6'-c]-pyrido-6,7,2',3'-indolomorphinan,
17-allyl-6,7-didehydro-4,5α-epoxy-14β-hydroxy-3-methoxy-[5',6'-c]-pyrido-6,7,2',3'-indolomorphinan,
17-cyclopropylmethyl-6,7-didehydro-4,5α-epoxy-3,14β-dihydroxy-[4',5'-c]-pyrido-6,7,2',3'-indolomorphinan,
17-allyl-6,7-didehydro-4,5α-epoxy-3,14β-dihydroxy-[4',5'-c]-pyrido-6,7,2',3'-indolomorphinan,
17-cyclopropylmethyl-6,7-didehydro-4,5α-epoxy-14β-hydroxy-3-methoxy-[4',5'-c]-pyrido-6,7,2',3'-indolomorphinan,
17-allyl-6,7-didehydro-4,5α-epoxy-14β-hydroxy-3-methoxy-[4',5'-c]-pyrido-6,7,2',3'-indolomorphinan,
17-cyclopropylmethyl-6,7-didehydro-4,5α-epoxy-3,14β-dihydroxy-[7',6'-b]-pyrido-6,7,2',3'-indolomorphinan,
17-allyl-6,7-didehydro-4,5α-epoxy-3,14β-dihydroxy-[7',6'-b]-pyrido-6,7,2',3'-indolomorphinan,
17-cyclopropylmethyl-6,7-didehydro-4,5α-epoxy-14β-hydroxy-3-methoxy-[7',6'-b]-pyrido-6,7,2',3'-indolomorphinan,
17-allyl-6,7-didehydro-4,5α-epoxy-14β-hydroxy-3-methoxy-[7',6'-b]-pyrido-6,7,2',3'-indolomorphinan,
17-cyclopropylmethyl-6,7-didehydro-4,5α-epoxy-3,14β-dihydroxy-[6',5'-b]-pyrido-6,7,2',3'-indolomorphinan,
17-allyl-6,7-didehydro-4,5α-epoxy-3,14β-dihydroxy-[6',5'-b]-pyrido-6,7,2',3'-indolomorphinan,
17-cyclopropylmethyl-6,7-didehydro-4,5α-epoxy-14β-hydroxy-3-methoxy-[6',5'-b]-pyrido-6,7,2',3'-indolomorphinan,
17-allyl-6,7-didehydro-4,5α-epoxy-14β-hydroxy-3-methoxy-[6',5'-b]-pyrido-6,7,2',3'-indolomorphinan,
17-cyclopropylmethyl-6,7-didehydro-4,5α-epoxy-3,14β-dihydroxy-[5',4'-b]-pyrido-6,7,2',3'-indolomorphinan,
17-allyl-6,7-didehydro-4,5α-epoxy-3,14β-dihydroxy-[5',4'-b]-pyrido-6,7,2',3'-indolomorphinan,
17-cyclopropylmethyl-6,7-didehydro-4,5α-epoxy-14β-hydroxy-3-methoxy-[5',4'-b]-pyrido-6,7,2',3'-indolomorphinan,
17-allyl-6,7-didehydro-4,5α-epoxy-14β-hydroxy-3-methoxy-[5',4'-b]-pyrido-6,7,2',3'-indolomorphinan,
17-cyclopropylmethyl-6,7-didehydro-4,5α-epoxy-3,14β-dihydroxy-[7',6'-c]-pyrido-6,7,2',3'-indolomorphinan,
17-allyl-6,7-didehydro-4,5α-epoxy-3,14β-dihydroxy-[7',6'-c]-pyrido-6,7,2',3'-indolomorphinan,
17-cyclopropylmethyl-6,7-didehydro-4,5α-epoxy-14β-hydroxy-3-methoxy-[7',6'-c]-pyrido-6,7,2',3'-indolomorphinan,
17-allyl-6,7-didehydro-4,5α-epoxy-14β-hydroxy-3-methoxy-[7',6'-c]-pyrido-6,7,2',3'-indolomorphinan,
17-cyclopropylmethyl-6,7-didehydro-4,5α-epoxy-3,14β-dihydroxy-[6',5'-c]-pyrido-6,7,2',3'-indolomorphinan,
17-allyl-6,7-didehydro-4,5α-epoxy-3,14β-dihydroxy-[6',5'-c]-pyrido-6,7,2',3'-indolomorphinan,
17-cyclopropylmethyl-6,7-didehydro-4,5α-epoxy-14β-hydroxy-3-methoxy-[6',5'-c]-pyrido-6,7,2',3'-indolomorphinan,
17-allyl-6,7-didehydro-4,5α-epoxy-14β-hydroxy-3-methoxy-[6',5'-c]-pyrido-6,7,2',3'-indolomorphinan,
17-cyclopropylmethyl-6,7-didehydro-4,5α-epoxy-3,14β-dihydroxy-[5',4'-c]-pyrido-6,7,2',3'-indolomorphinan,
17-allyl-6,7-didehydro-4,5α-epoxy-3,14β-dihydroxy-[5',4'-c]-pyrido-6,7,2',3'-indolomorphinan,
17-cyclopropylmethyl-6,7-didehydro-4,5α-epoxy-14β-hydroxy-3-methoxy-[5',4'-c]-pyrido-6,7,2',3'-indolomorphinan,
17-allyl-6,7-didehydro-4,5α-epoxy-14β-hydroxy-3-methoxy-[5',4'-c]-pyrido-6,7,2',3'-indolomorphinan,
17-cyclopropylmethyl-6,7-didehydro-4,5α-epoxy-3,14β-dihydroxy-1'-methyl-6',7'
17-cyclohexeno-6,7,2',3'-indolomorphinan,
17-allyl-6,7-didehydro-4,5α-epoxy-3,14β-dihydroxy-1'-methyl-6',7'-cyclohexeno-6,7,2',3'-indolomorphinan,
17-cyclopropylmethyl-6,7-didehydro-4,5α-epoxy-14β-hydroxy-3-methoxy-1'-methyl-6',7'-cyclohexeno-6,7,2',3'-indolomorphinan,
17-allyl-6,7-didehydro-4,5α-epoxy-14β-hydroxy-3-methoxy-1'-methyl-6',7'-cyclohexeno-6,7,2',3'-indolomorphinan,
17-cyclopropylmethyl-6,7-didehydro-4,5α-epoxy-3,14β-dihydroxy-1'-methyl-5',6'-cyclohexeno-6,7,2',3'-indolomorphinan,
17-allyl-6,7-didehydro-4,5α-epoxy-3,14β-dihydroxy-1'-methyl-5',6'-cyclohexeno-6,7,2',3'-indolomorphinan,
17-cyclopropylmethyl-6,7-didehydro-4,5α-epoxy-14β-hydroxy-3-methoxy-1'-methyl-5',6'-cyclohexeno-6,7,2',3'-indolomorphinan,
17-allyl-6,7-didehydro-4,5α-epoxy-14β-hydroxy-3-methoxy-1'-methyl-5',6'-cyclohexeno-6,7,2',3'-indolomorphinan,
17-cyclopropylmethyl-6,7-didehydro-4,5α-epoxy-3,14β-dihydroxy-1'-methyl-4',5'-cyclohexeno-6,7,2',3'-indolomorphinan,
17-allyl-6,7-didehydro-4,5α-epoxy-3,14β-dihydroxy-1'-methyl-4',5'-cyclohexeno-6,7,2',3'-indolomorphinan,
17-cyclopropylmethyl-6,7-didehydro-4,5α-epoxy-14β-hydroxy-3-methoxy-1'-methyl-4',5'-cyclohexeno-6,7,2',3'-indolomorphinan,
17-allyl-6,7-didehydro-4,5α-epoxy-14β-hydroxy-3-methoxy-1'-methyl-4',5'-cyclohexeno-6,7,2',3'-indolomorphinan,
17-cyclopropylmethyl-6,7-didehydro-4,5α-epoxy-3,14β-dihydroxy-1'-methyl-6',7'-cyclopenteno-6,7,2',3'-indolomorphinan,
17-allyl-6,7-didehydro-4,5α-epoxy-3,14β-dihydroxy-1'-methyl-6',7'-cyclopenteno-6,7,2',3'-indolomorphinan,
17-cyclopropylmethyl-6,7-didehydro-4,5α-epoxy-14β-hydroxy-3-methoxy-1'-methyl-6',7'-cyclopenteno-6,7,2',3'-indolomorphinan,
17-allyl-6,7-didehydro-4,5α-epoxy-14β-hydroxy-3-methoxy-1'-methyl-6',7'-cyclopenteno-6,7,2',3'-indolomorphinan,
17-cyclopropylmethyl-6,7-didehydro-4,5α-epoxy-3,14β-dihydroxy-1'-methyl-5',6'-cyclopenteno-6,7,2',3'-indolomorphinan,
17-allyl-6,7-didehydro-4,5α-epoxy-3,14β-dihydroxy-1'-methyl-5',6'-cyclopenteno-6,7,2',3'-indolomorphinan,
17-cyclopropylmethyl-6,7-didehydro-4,5α-epoxy-14β-hydroxy-3-methoxy-1'-methyl-5',6'-cyclopenteno-6,7,2',3'-indolomorphinan,
17-allyl-6,7-didehydro-4,5α-epoxy-14β-hydroxy-3-methoxy-1'-methyl-5',6'-cyclopenteno-6,7,2',3'-indolomorphinan,
17-cyclopropylmethyl-6,7-didehydro-4,5α-epoxy-3,14β-dihydroxy-1'-methyl-4',5'-cyclopenteno-6,7,2',3'-indolomorphinan,
17-allyl-6,7-didehydro-4,5α-epoxy-3,14β-dihydroxy-1'-methyl-4',5'-cyclopenteno-6,7,2',3'-indolomorphinan,
17-cyclopropylmethyl-6,7-didehydro-4,5α-epoxy-14β-hydroxy-3-methoxy-1'-methyl-4',5'-cyclopenteno-6,7,2',3'-indolomorphinan,
17-allyl-6,7-didehydro-4,5α-epoxy-14β-hydroxy-3-methoxy-1'-methyl-4',5'-cyclopenteno-6,7,2',3'-indolomorphinan, 17-cyclopropylmethyl-6,7-didehydro-4,5α-epoxy-3,14β-dihydroxy-1'-methyl-6',7'-cyclohepteno-6,7,2',3'-indolomorphinan.

17-allyl-6,7-didehydro-4,5α-epoxy-3,14β-dihydroxy-1'-methyl-6',7'-cyclohepteno-6,7,2',3'-indolomorphinan.

17-cyclopropylmethyl-6,7-didehydro-4,5α-epoxy-14β-hydroxy-3-methoxy-1'-methyl-6',7'-cyclohepteno-6,7,2',3'-indolomorphinan.

17-allyl-6,7-didehydro-4,5α-epoxy-14β-hydroxy-3-methoxy-1'-methyl-6',7'-cyclohepteno-6,7,2',3'-indolomorphinan.

17-cyclopropylmethyl-6,7-didehydro-4,5α-epoxy-3,14β-dihydroxy-1'-methyl-5',6'-cyclohepteno-6,7,2',3'-indolomorphinan.

17-allyl-6,7-didehydro-4,5α-epoxy-3,14β-dihydroxy-1'-methyl-5',6'-cyclohepteno-6,7,2',3'-indolomorphinan.

17-cyclopropylmethyl-6,7-didehydro-4,5α-epoxy-14β-hydroxy-3-methoxy-1'-methyl-5',6'-cyclohepteno-6,7,2',3'-indolomorphinan.

17-allyl-6,7-didehydro-4,5α-epoxy-14β-hydroxy-3-methoxy-1'-methyl-5',6'-cyclohepteno-6,7,2',3'-indolomorphinan.

17-cyclopropylmethyl-6,7-didehydro-4,5α-epoxy-3,14β-dihydroxy-1'-methyl-4',5'-cyclohepteno-6,7,2',3'-indolomorphinan.

17-allyl-6,7-didehydro-4,5α-epoxy-3,14β-dihydroxy-1'-methyl-4',5'-cyclohepteno-6,7,2',3'-indolomorphinan.

17-cyclopropylmethyl-6,7-didehydro-4,5α-epoxy-14β-hydroxy-3-methoxy-1'-methyl-4',5'-cyclohepteno-6,7,2',3'-indolomorphinan.

17-allyl-6,7-didehydro-4,5α-epoxy-14β-hydroxy-3-methoxy-1'-methyl-4',5'-cyclohepteno-6,7,2',3'-indolomorphinan.

17-cyclopropylmethyl-6,7-didehydro-4,5α-epoxy-3,14β-dihydroxy-1'-methyl-6',7'-benzo-6,7,2',3'-indolomorphinan.

17-allyl-6,7-didehydro-4,5α-epoxy-3,14β-dihydroxy-1'-methyl-6',7'-benzo-6,7,2',3'-indolomorphinan.

17-cyclopropylmethyl-6,7-didehydro-4,5α-epoxy-14β-hydroxy-3-methoxy-1'-methyl-6',7'-benzo-6,7,2',3'-indolomorphinan.

17-allyl-6,7-didehydro-4,5α-epoxy-14β-hydroxy-3-methoxy-1'-methyl-6',7'-benzo-6,7,2',3'-indolomorphinan.

17-cyclopropylmethyl-6,7-didehydro-4,5α-epoxy-3,14β-dihydroxy-1'-methyl-5',6'-benzo-6,7,2',3'-indolomorphinan.

17-allyl-6,7-didehydro-4,5α-epoxy-3,14β-dihydroxy-1'-methyl-5',6'-benzo-6,7,2',3'-indolomorphinan.

17-cyclopropylmethyl-6,7-didehydro-4,5α-epoxy-14β-hydroxy-3-methoxy-1'-methyl-5',6'-benzo-6,7,2',3'-indolomorphinan.

17-allyl-6,7-didehydro-4,5α-epoxy-14β-hydroxy-3-methoxy-1'-methyl-5',6'-benzo-6,7,2',3'-indolomorphinan.

17-cyclopropylmethyl-6,7-didehydro-4,5α-epoxy-3,14β-dihydroxy-1'-methyl-4',5'-benzo-6,7,2',3'-indolomorphinan.

17-allyl-6,7-didehydro-4,5α-epoxy-3,14β-dihydroxy-1'-methyl-4',5'-benzo-6,7,2',3'-indolomorphinan.

17-cyclopropylmethyl-6,7-didehydro-4,5α-epoxy-14β-hydroxy-3-methoxy-1'-methyl-4',5'-benzo-6,7,2',3'-indolomorphinan.

17-allyl-6,7-didehydro-4,5α-epoxy-14β-hydroxy-3-methoxy-1'-methyl-4',5'-benzo-6,7,2',3'-indolomorphinan.

17-cyclopropylmethyl-6,7-didehydro-4,5α-epoxy-3,14β-dihydroxy-1'-methyl-[6',7'-b]-pyrido-6,7,2',3'-indolomorphinan.

17-allyl-6,7-didehydro-4,5α-epoxy-3,14β-dihydroxy-1'-methyl-[6',7'-b]-pyrido-6,7,2',3'-indolomorphinan.

17-cyclopropylmethyl-6,7-didehydro-4,5α-epoxy-14β-hydroxy-3-methoxy-1'-methyl-[6',7'-b]-pyrido-6,7,2',3'-indolomorphinan.

17-allyl-6,7-didehydro-4,5α-epoxy-14β-hydroxy-3-methoxy-1'-methyl-[6',7'-b]-pyrido-6,7,2',3'-indolomorphinan.

17-cyclopropylmethyl-6,7-didehydro-4,5α-epoxy-3,14β-dihydroxy-1'-methyl-[5',6'-b]-pyrido-6,7,2',3'-indolomorphinan.

17-allyl-6,7-didehydro-4,5α-epoxy-3,14β-dihydroxy-1'-methyl-[5',6'-b]-pyrido-6,7,2',3'-indolomorphinan.

17-cyclopropylmethyl-6,7-didehydro-4,5α-epoxy-14β-hydroxy-3-methoxy-1'-methyl-[5',6'-b]-pyrido-6,7,2',3'-indolomorphinan.

17-allyl-6,7-didehydro-4,5α-epoxy-14β-hydroxy-3-methoxy-1'-methyl-[5',6'-b]-pyrido-6,7,2',3'-indolomorphinan.

17-cyclopropylmethyl-6,7-didehydro-4,5α-epoxy-3,14β-dihydroxy-1'-methyl-[4',5'-b]-pyrido-6,7,2',3'-indolomorphinan.

17-allyl-6,7-didehydro-4,5α-epoxy-3,14β-dihydroxy-1'-methyl-[4',5'-b]-pyrido-6,7,2',3'-indolomorphinan.

17-cyclopropylmethyl-6,7-didehydro-4,5α-epoxy-14β-hydroxy-3-methoxy-1'-methyl-[4',5'-b]-pyrido-6,7,2',3'-indolomorphinan.

17-allyl-6,7-didehydro-4,5α-epoxy-14β-hydroxy-3-methoxy-1'-methyl-[4',5'-b]-pyrido-6,7,2',3'-indolomorphinan.

17-cyclopropylmethyl-6,7-didehydro-4,5α-epoxy-3,14β-dihydroxy-1'-methyl-[6',7'-c]-pyrido-6,7,2',3'-indolomorphinan.

17-allyl-6,7-didehydro-4,5α-epoxy-3,14β-dihydroxy-1'-methyl-[6',7'-c]-pyrido-6,7,2',3'-indolomorphinan.

17-cyclopropylmethyl-6,7-didehydro-4,5α-epoxy-14β-hydroxy-3-methoxy-1'-methyl-[6',7'-c]-pyrido-6,7,2',3'-indolomorphinan.

17-allyl-6,7-didehydro-4,5α-epoxy-14β-hydroxy-3-methoxy-1'-methyl-[6',7'-c]-pyrido-6,7,2',3'-indolomorphinan.

17-cyclopropylmethyl-6,7-didehydro-4,5α-epoxy-3,14β-dihydroxy-1'-methyl-[5',6'-c]-pyrido-6,7,2',3'-indolomorphinan.

17-allyl-6,7-didehydro-4,5α-epoxy-3,14β-dihydroxy-1'-methyl-[5',6'-c]-pyrido-6,7,2',3'-indolomorphinan.

17-cyclopropylmethyl-6,7-didehydro-4,5α-epoxy-14β-hydroxy-3-methoxy-1'-methyl-[5',6'-c]-pyrido-6,7,2',3'-indolomorphinan.

17-allyl-6,7-didehydro-4,5α-epoxy-14β-hydroxy-3-methoxy-1'-methyl-[5',6'-c]-pyrido-6,7,2',3'-indolomorphinan.

17-cyclopropylmethyl-6,7-didehydro-4,5α-epoxy-3,14β-dihydroxy-1'-methyl-[4',5'-c]-pyrido-6,7,2',3'-indolomorphinan.

17-allyl-6,7-didehydro-4,5α-epoxy-3,14β-dihydroxy-1'-methyl-[4',5'-c]-pyrido-6,7,2',3'-indolomorphinan.

17-cyclopropylmethyl-6,7-didehydro-4,5α-epoxy-14β-hydroxy-3-methoxy-1'-methyl-[4',5'-c]-pyrido-6,7,2',3'-indolomorphinan.

17-allyl-6,7-didehydro-4,5α-epoxy-14β-hydroxy-3-methoxy-1'-methyl-[4',5'-c]-pyrido-6,7,2',3'-indolomorphinan.

17-cyclopropylmethyl-6,7-didehydro-4,5α-epoxy-3,14β-dihydroxy-1'-methyl-[7',6'-b]-pyrido-6,7,2',3'-indolomorphinan.

17-allyl-6,7-didehydro-4,5α-epoxy-3,14β-dihydroxy-1'-methyl-[7',6'-b]-pyrido-6,7,2',3'-indolomorphinan.

17-cyclopropylmethyl-6,7-didehydro-4,5α-epoxy-14β-hydroxy-3-methoxy-1'-methyl-[7',6'-b]-pyrido-6,7,2',3'-indolomorphinan, 17-allyl-6,7-didehydro-4,5α-epoxy-14β-hydroxy-3-methoxy-1'-methyl-[7',6'-b]-pyrido-6,7,2',3'-indolomorphinan, 17-cyclopropylmethyl-6,7-didehydro-4,5α-epoxy-3,14β-dihydroxy-1'-methyl-[6',5'-b]-pyrido-6,7,2',3'-indolomorphinan, 17-allyl-6,7-didehydro-4,5α-epoxy-3,14β-dihydroxy-1'-methyl-[6',5'-b]-pyrido-6,7,2',3'-indolomorphinan, 17-cyclopropylmethyl-6,7-didehydro-4,5α-epoxy-14β-hydroxy-3-methoxy-1'-methyl-[6',5'-b]-pyrido-6,7,2',3'-indolomorphinan, 17-allyl-6,7-didehydro-4,5α-epoxy-14β-hydroxy-3-methoxy-1'-methyl-[6',5'-b]-pyrido-6,7,2',3'-indolomorphinan, 17-cyclopropylmethyl-6,7-didehydro-4,5α-epoxy-3,14β-dihydroxy-1'-methyl-[5',4'-b]-pyrido-6,7,2',3'-indolomorphinan, 17-allyl-6,7-didehydro-4,5α-epoxy-3,14β-dihydroxy-1'-methyl-[5',4'-b]-pyrido-6,7,2',3'-indolomorphinan, 17-cyclopropylmethyl-6,7-didehydro-4,5α-epoxy-14β-hydroxy-3-methoxy-1'-methyl-[5',4'-b]-pyrido-6,7,2',3'-indolomorphinan, 17-allyl-6,7-didehydro-4,5α-epoxy-14β-hydroxy-3-methoxy-1'-methyl-[5',4'-b]-pyrido-6,7,2',3'-indolomorphinan, 17-cyclopropylmethyl-6,7-didehydro-4,5α-epoxy-3,14β-dihydroxy-1'-methyl-[7',6'-c]-pyrido-6,7,2',3'-indolomorphinan, 17-allyl-6,7-didehydro-4,5α-epoxy-3,14β-dihydroxy-1'-methyl-[7',6'-c]-pyrido-6,7,2',3'-indolomorphinan, 17-cyclopropylmethyl-6,7-didehydro-4,5α-epoxy-14β-hydroxy-3-methoxy-1'-methyl-[7',6'-c]-pyrido-6,7,2',3'-indolomorphinan, 17-allyl-6,7-didehydro-4,5α-epoxy-14β-hydroxy-3-methoxy-1'-methyl-[7',6'-c]-pyrido-6,7,2',3'-indolomorphinan, 17-cyclopropylmethyl-6,7-didehydro-4,5α-epoxy-3,14β-dihydroxy-1'-methyl-[6',5'-c]-pyrido-6,7,2',3'-indolomorphinan, 17-allyl-6,7-didehydro-4,5α-epoxy-3,14β-dihydroxy-1'-methyl-[6',5'-c]-pyrido-6,7,2',3'-indolomorphinan, 17-cyclopropylmethyl-6,7-didehydro-4,5α-epoxy-14β-hydroxy-3-methoxy-1'-methyl-[6',5'-c]-pyrido-6,7,2',3'-indolomorphinan, 17-allyl-6,7-didehydro-4,5α-epoxy-14β-hydroxy-3-methoxy-1'-methyl-[6',5'-c]-pyrido-6,7,2',3'-indolomorphinan, 17-cyclopropylmethyl-6,7-didehydro-4,5α-epoxy-3,14β-dihydroxy-1'-methyl-[5',4'-c]-pyrido-6,7,2',3'-indolomorphinan, 17-allyl-6,7-didehydro-4,5α-epoxy-3,14β-dihydroxy-1'-methyl-[5',4'-c]-pyrido-6,7,2',3'-indolomorphinan, 17-cyclopropylmethyl-6,7-didehydro-4,5α-epoxy-14β-hydroxy-3-methoxy-1'-methyl-[5',4'-c]-pyrido-6,7,2',3'-indolomorphinan, 17-allyl-6,7-didehydro-4,5α-epoxy-14β-hydroxy-3-methoxy-1'-methyl-[5',4'-c]-pyrido-6,7,2',3'-indolomorphinan, 17-cyclopropylmethyl-6,7-didehydro-4,5α-epoxy-3,14β-dihydroxy-4'-methyl-6',7'-cyclohexeno-6,7,2',3'-indolomorphinan, 17-allyl-6,7-didehydro-4,5α-epoxy-3,14β-dihydroxy-4'-methyl-6',7'-cyclohexeno-6,7,2',3'-indolomorphinan, 17-cyclopropylmethyl-6,7-didehydro-4,5α-epoxy-14β-hydroxy-3-methoxy-4'-methyl-6',7'-cyclohexeno-6,7,2',3'-indolomorphinan, 17-allyl-6,7-didehydro-4,5α-epoxy-14β-hydroxy-3-methoxy-4'-methyl-6',7'-cyclohexeno-6,7,2',3'-indolomorphinan, 17-cyclopropylmethyl-6,7-didehydro-4,5α-epoxy-3,14β-dihydroxy-5'-methyl-6',7'-cyclohexeno-6,7,2',3'-indolomorphinan, 17-allyl-6,7-didehydro-4,5α-epoxy-3,14β-dihydroxy-5'-methyl-6',7'-cyclohexeno-6,7,2',3'-indolomorphinan, 17-cyclopropylmethyl-6,7-didehydro-4,5α-epoxy-14β-hydroxy-3-methoxy-5'-methyl-6',7'-cyclohexeno-6,7,2',3'-indolomorphinan, 17-allyl-6,7-didehydro-4,5α-epoxy-14β-hydroxy-3-methoxy-5'-methyl-6',7'-cyclohexeno-6,7,2',3'-indolomorphinan, 17-cyclopropylmethyl-6,7-didehydro-4,5α-epoxy-3,14β-dihydroxy-3"-methyl-6',7'-cyclohexeno-6,7,2',3'-indolomorphinan, 17-allyl-6,7-didehydro-4,5α-epoxy-3,14β-dihydroxy-3"-methyl-6',7'-cyclohexeno-6,7,2',3'-indolomorphinan, 17-cyclopropylmethyl-6,7-didehydro-4,5α-epoxy-14β-hydroxy-3-methoxy-3"-methyl-6',7'-cyclohexeno-6,7,2',3'-indolomorphinan, 17-allyl-6,7-didehydro-4,5α-epoxy-14β-hydroxy-3-methoxy-3"-methyl-6',7'-cyclohexeno-6,7,2',3'-indolomorphinan, 17-cyclopropylmethyl-6,7-didehydro-4,5α-epoxy-3,14β-dihydroxy-4"-methyl-6',7'-cyclohexeno-6,7,2',3'-indolomorphinan, 17-allyl-6,7-didehydro-4,5α-epoxy-3,14β-dihydroxy-4"-methyl-6',7'-cyclohexeno-6,7,2',3'-indolomorphinan, 17-cyclopropylmethyl-6,7-didehydro-4,5α-epoxy-14β-hydroxy-3-methoxy-4"-methyl-6',7'-cyclohexeno-6,7,2',3'-indolomorphinan, 17-allyl-6,7-didehydro-4,5α-epoxy-145-hydroxy-3-methoxy-4"-methyl-6',7'-cyclohexeno-6,7,2',3'-indolomorphinan, 17-cyclopropylmethyl-6,7-didehydro-4,5α-epoxy-3,14β-dihydroxy-5"-methyl-6',7'-cyclohexeno-6,7,2',3'-indolomorphinan, 17-allyl-6,7-didehydro-4,5α-epoxy-3,14β-dihydroxy-5"-methyl-6',7'-cyclohexeno-6,7,2',3'-indolomorphinan, 17-cyclopropylmethyl-6,7-didehydro-4,5α-epoxy-14β-hydroxy-3-methoxy-5"-methyl-6',7'-cyclohexeno-6,7,2',3'-indolomorphinan, 17-allyl-6,7-didehydro-4,5α-epoxy-14β-hydroxy-3-methoxy-5"-methyl-6',7'-cyclohexeno-6,7,2',3'-indolomorphinan, 17-cyclopropylmethyl-6,7-didehydro-4,5α-epoxy-3,14β-dihydroxy-6"-methyl-6',7'-cyclohexeno-6,7,2',3'-indolomorphinan, 17-allyl-6,7-didehydro-4,5α-epoxy-3,14β-dihydroxy-6"-methyl-6',7'-cyclohexeno-6,7,2',3'-indolomorphinan, 17-cyclopropylmethyl-6,7-didehydro-4,5α-epoxy-14β-hydroxy-3-methoxy-6"-methyl-6',7'-cyclohexeno-6,7,2',3'-indolomorphinan, 17-allyl-6,7-didehydro-4,5α-epoxy-14β-hydroxy-3-methoxy-6"-methyl-6',7'-cyclohexeno-6,7,2',3'-indolomorphinan, 17-cyclopropylmethyl-6,7-didehydro-4,5α-epoxy-3,14β-dihydroxy-4'-bromo-6',7'-cyclohexeno-6,7,2',3'-indolomorphinan, 17-allyl-6,7-didehydro-4,5α-epoxy-3,14β-dihydroxy-4'-bromo-6',7'-cyclohexeno-6,7,2',3'-indolomorphinan, 17-cyclopropylmethyl-6,7-didehydro-4,5α-epoxy-14β-hydroxy-3-methoxy-4'-bromo-6',7'-cyclohexeno-6,7,2',3'-indolomorphinan, 17-allyl-6,7-didehydro-4,5α-epoxy-14β-hydroxy-3-methoxy-4'-bromo-6',7'-cyclohexeno-6,7,2',3'-indolomorphinan, 17-cyclopropylmethyl-6,7-didehydro-4,5α-epoxy-3,14β-dihydroxy-5'-bromo-6',7'-cyclohexeno-6,7,2',3'-indolomorphinan, 17-allyl-6,7-didehydro-4,5α-epoxy-3,14β-dihydroxy-5'-bromo-6',7'-cyclohexeno-6,7,2',3'-indolomorphinan, 17-cyclopropylmethyl-6,7-didehydro-4,5α-epoxy-14β-hydroxy-3-methoxy-5'-bromo-6',7'-cyclohexeno-6,7,2',3'-indolomorphinan, 17-allyl-6,7-didehydro-4,5α-epoxy-14β-hydroxy-3-methoxy-5'-bromo-6',7'-cyclohexeno-6,7,2',3'-indolomorphinan, 17-cyclopropylmethyl-6,7-didehydro-4,5α-epoxy-3,14β-dihydroxy-3"-bromo-6',7'-cyclohexeno-6,7,2',3'-indolomorphinan, 17-allyl-6,7-didehydro-4,5α-epoxy-3,14β-dihydroxy-3"-bromo-6',7'-cyclohexeno-6,7,2',3'-indolomorphinan, 17-cyclopropylmethyl-6,7-didehydro-4,5α-epoxy-14β-hydroxy-3-methoxy-3"-bromo-6',7'-cyclohexeno-6,7,2',3'-indolomorphinan, 17-allyl-6,7-didehydro-4,5α-epoxy-14β-hydroxy-3-methoxy-3"-bromo-6',7'-cyclohexeno-6,7,2',3'-indolomorphinan, 17-cyclopropylmethyl-6,7-didehydro-4,5α-epoxy-3,14β-dihydroxy-4"-bromo-6',7'-cyclohexeno-6,7,2',3'-indolomorphinan, 17-allyl-6,7-didehydro-4,5α-epoxy-3,14β-dihydroxy-4"-bromo-6',7'-cyclohexeno-6,7,2',3'-indolomorphinan, 17-cyclopropylmethyl-6,7-didehydro-4,5α-epoxy-14β-hydroxy-3-methoxy-4"-bromo-6',7'-cyclohexeno-6,7,2',3'-indolomorphinan, 17-allyl-6,7-didehydro-4,5α-epoxy-14β-hydroxy-3-methoxy-4"-bromo-6',7'-cyclohexeno-6,7,2',3'-indolomorphinan, 17-cyclopropylmethyl-6,7-didehydro-4,5α-epoxy-3,14β-dihydroxy-5"-bromo-6',7'-cyclohexeno-6,7,2',3'-indolomorphinan, 17-allyl-6,7-didehydro-4,5α-epoxy-3,14β-dihydroxy-5"-bromo-6',7'-cyclohexeno-6,7,2',3'-indolomorphinan, 17-cyclopropylmethyl-6,7-didehydro-4,5α-epoxy-14β-hydroxy-3-methoxy-5"-bromo-6',7'-cyclohexeno-6,7,2',3'-indolomorphinan, 17-allyl-6,7-didehydro-4,5α-epoxy-14β-hydroxy-3-methoxy-5"-bromo-6',7'-cyclohexeno-6,7,2',3'-indolomorphinan, 17-cyclopropylmethyl-6,7-didehydro-4,5α-epoxy-3,14β-dihydroxy-6"-bromo-6',7'-cyclohexeno-6,7,2',3'-indolomorphinan, 17-allyl-6,7-didehydro-4,5α-epoxy-3,14β-dihydroxy-6"-bromo-6',7'-cyclohexeno-6,7,2',3'-indolomorphinan, 17-cyclopropylmethyl-6,7-didehydro-4,5α-epoxy-14β-hydroxy-3-methoxy-6"-bromo-6',7'-cyclohexeno-6,7,2',3'-indolomorphinan, 17-allyl-6,7-didehydro-4,5α-epoxy-14β-hydroxy-3-methoxy-6"-bromo-6',7'-cyclohexeno-6,7,2',3'-indolomorphinan, 17-cyclopropylmethyl-6,7-didehydro-4,5α-epoxy-3,14β-dihydroxy-4'-methoxy-6',7'-cyclohexeno-6,7,2',3'-indolomorphinan, 17-allyl-6,7-didehydro-4,5α-epoxy-3,14β-dihydroxy-4'-methoxy-6',7'-cyclohexeno-6,7,2',3'-indolomorphinan, 17-cyclopropylmethyl-6,7-didehydro-4,5α-epoxy-14β-hydroxy-3,4'-dimethoxy-6',7'-cyclohexeno-6,7,2',3'-indolomorphinan, 17-allyl-6,7-didehydro-4,5α-epoxy-14β-hydroxy-3,4'-dimethoxy-6',7'-cyclohexeno-6,7,2',3'-indolomorphinan, 17-cyclopropylmethyl-6,7-didehydro-4,5α-epoxy-3,14β-dihydroxy-5'-methoxy-6',7'-cyclohexeno-6,7,2',3'-indolomorphinan, 17-allyl-6,7-didehydro-4,5α-epoxy-3,14β-dihydroxy-5'-methoxy-6',7'-cyclohexeno-6,7,2',3'-indolomorphinan, 17-cyclopropylmethyl-6,7-didehydro-4,5α-epoxy-14β-hydroxy-3,5'-dimethoxy-6',7'-cyclohexeno-6,7,2',3'-indolomorphinan, 17-allyl,6,7-didehydro-4,5α-epoxy-14β-hydroxy-3,5'-dimethoxy-6',7'-cyclohexeno-6,7,2',3'-indolomorphinan, 17-cyclopropylmethyl-6,7-didehydro-4,5α-epoxy-3,14β-dihydroxy-3"-methoxy-6',7'-cyclohexeno-6,7,2',3'-indolomorphinan, 17-allyl-6,7-didehydro-4,5α-epoxy-3,14β-dihydroxy-3"-methoxy-6',7'-cyclohexeno-6,7,2',3'-indolomorphinan, 17-cyclopropylmethyl-6,7-didehydro-4,5α-epoxy-14β-hydroxy-3,3"-dimethoxy-6',7'-cyclohexeno-6,7,2',3'-indolomorphinan, 17-allyl-6,7-didehydro-4,5α-epoxy-14β-hydroxy-3,3"-dimethoxy-6',7'-cyclohexeno-6,7,2',3'-indolomorphinan, 17-cyclopropylmethyl-6,7-didehydro-4,5α-epoxy-3,14β-dihydroxy-4"-methoxy-6',7'-cyclohexeno-6,7,2',3'-indolomorphinan, 17-allyl-6,7-didehydro-4,5α-epoxy-3,14β-dihydroxy-4"-methoxy-6',7'-cyclohexeno-6,7,2',3'-indolomorphinan, 17-cyclopropylmethyl-6,7-didehydro-4,5α-epoxy-14β-hydroxy-3,4"-dimethoxy-6',7'-cyclohexeno-6,7,2',3'-indolomorphinan, 17-allyl-6,7-didehydro-4,5α-epoxy-14β-hydroxy-3,4"-dimethoxy-6',7'-cyclohexeno-6,7,2',3'-indolomorphinan, 17-cyclopropylmethyl-6,7-didehydro-4,5α-epoxy-3,14β-dihydroxy-5"-methoxy-6',7'-cyclohexeno-6,7,2',3'-indolomorphinan, 17-allyl-6,7-didehydro-4,5α-epoxy-3,14β-dihydroxy-5"-methoxy-6',7'-cyclohexeno-6,7,2',3'-indolomorphinan, 17-cyclopropylmethyl-6,7-didehydro-4,5α-epoxy-14β-hydroxy-3,5"-dimethoxy-6',7'-cyclohexeno-6,7,2',3'-indolomorphinan, 17-allyl-6,7-didehydro-4,5α-epoxy-14β-hydroxy-3,5"-dimethoxy-6',7'-cyclohexeno-6,7,2',3'-indolomorphinan, 17-cyclopropylmethyl-6,7-didehydro-4,5α-epoxy-3,14β-dihydroxy-6"-methoxy-6',7'-cyclohexeno-6,7,2',3'-indolomorphinan, 17-allyl-6,7-didehydro-4,5α-epoxy-3,14β-dihydroxy-6"-methoxy-6',7'-cyclohexeno-6,7,2',3'-indolomorphinan, 17-cyclopropylmethyl-6,7-didehydro-4,5α-epoxy-14β-hydroxy-3,6"-dimethoxy-6',7'-cyclohexeno-6,7,2',3'-indolomorphinan, 17-allyl-6,7-didehydro-4,5α-epoxy-14β-hydroxy-3,6"-dimethoxy-6',7'-cyclohexeno-6,7,2',3'-indolomorphinan, 17-cyclopropylmethyl-6,7-didehydro-4,5α-epoxy-3,14β-dihydroxy-4'-nitro-6',7'-cyclohexeno-6,7,2',3'-indolomorphinan, 17-allyl-6,7-didehydro-4,5α-epoxy-3,14β-dihydroxy-4'-nitro-6',7'-cyclohexeno-6,7,2',3'-indolomorphinan, 17-cyclopropylmethyl-6,7-didehydro-4,5α-epoxy-14β-hydroxy-3-methoxy-4'-nitro-6',7'-cyclohexeno-6,7,2',3'-indolomorphinan, 17-allyl-6,7-didehydro-4,5α-epoxy-14β-hydroxy-3-methoxy-4'-nitro-6',7'-cyclohexeno-6,7,2',3'-indolomorphinan, 17-cyclopropylmethyl-6,7-didehydro-4,5α-epoxy-3,14β-dihydroxy-5'-nitro-6',7'-cyclohexeno-6,7,2',3'-indolomorphinan, 17-allyl-6,7-didehydro-4,5α-epoxy-3,14β-dihydroxy-5'-nitro-6',7'-cyclohexeno-6,7,2',3'-indolomorphinan, 17-cyclopropylmethyl-6,7-didehydro-4,5α-epoxy-14β-hydroxy-3-methoxy-5'-nitro-6',7'-cyclohexeno-6,7,2',3'-indolomorphinan, 17-allyl-6,7-didehydro-4,5α-epoxy-14β-hydroxy-3-methoxy-5'-nitro-6',7'-cyclohexeno-6,7,2',3'-indolomorphinan, 17-cyclopropylmethyl-6,7-didehydro-4,5α-epoxy-3,14β-dihydroxy-3"-nitro-6',7'-cyclohexeno-6,7,2',3'-indolomorphinan, 17-allyl-6,7-didehydro-4,5α-epoxy-3,14β-dihydroxy-3"-nitro-6',7'-cyclohexeno-6,7,2',3'-indolomorphinan, 17-cyclopropylmethyl-6,7-didehydro-4,5α-epoxy-14β-hydroxy-3-methoxy-3"-nitro-6',7'-cyclohexeno-6,7,2',3'-indolomorphinan, 17-allyl-6,7-didehydro-4,5α-epoxy-14β-hydroxy-3-methoxy-3"-nitro-6',7'-cyclohexeno-6,7,2,3+-indolomorphinan, 17-cyclopropylmethyl-6,7-didehydro-4,5α-epoxy-3,14β-dihydroxy-4"-nitro-6',7'-cyclohexeno-6,7,2',3'-indolomorphinan, 17-allyl-6,7-didehydro-4,5α-epoxy-3,14β-dihydroxy-4"-nitro-6',7'-cyclohexeno-6,7,2',3'-indolomorphinan, 17-cyclopropylmethyl-6,7-didehydro-4,5α-epoxy-14β-hydroxy-3-methoxy-4"-nitro-6',7'-cyclohexeno-6,7,2',3'-indolomorphinan, 17-allyl-6,7-didehydro-4,5α-epoxy-14β-hydroxy-3-methoxy-4"-nitro-6',7'-cyclohexeno-6,7,2',3'-indolomorphinan, 17-cyclopropylmethyl-6,7-didehydro-4,5α-epoxy-3,14β-dihydroxy-5"-nitro-6',7'-cyclohexeno-6,7,2',3'-indolomorphinan, 17-allyl-6,7-didehydro-4,5α-epoxy-3,14β-dihydroxy-5"-nitro-6',7'-cyclohexeno-6,7,2',3'-indolomorphinan, 17-cyclopropylmethyl-6,7-didehydro-4,5α-epoxy-14β-hydroxy-3-methoxy-5"-nitro-6',7'-cyclohexeno-6,7,2',3'-indolomorphinan, 17-allyl-6,7-didehydro-4,5α-epoxy-14β-hydroxy-3-methoxy-5"-nitro-6',7'-cyclohexeno-6,7,2',3'-indolomorphinan, 17-cyclopropylmethyl-6,7-didehydro-4,5α-epoxy-3,14β-dihydroxy-6"-nitro-6',7'-cyclohexeno-6,7,2',3'-indolomorphinan, 17-allyl-6,7-didehydro-4,5α-epoxy-3,14β-dihydroxy-6"-nitro-6',7'-cyclohexeno-6,7,2',3'-indolomorphinan, 17-cyclopropylmethyl-6,7-didehydro-4,5α-epoxy-14β-hydroxy-3-methoxy-6"-nitro-6',7'-cyclohexeno-6,7,2',3'-indolomorphinan, '

17-allyl-6,7-didehydro-4,5α-epoxy-14β-hydroxy-3-methoxy-6"-nitro-6',7'-cyclohexeno-6,7,2',3'-indolomorphinan, 17-cyclopropylmethyl-6,7-didehydro-4,5α-epoxy-3,14β-dihydroxy-4'-methoxycarbonyl-6',7'-cyclohexeno-6,7,2',3'-indolomorphinan, 17-allyl-6,7-didehydro-4,5α-epoxy-3,14β-dihydroxy-4'-methoxycarbonyl-6',7'-cyclohexeno-6,7,2',3'-indolomorphinan, 17-cyclopropylmethyl-6,7-didehydro-4,5α-epoxy-14β-hydroxy-3-methoxy-4'-methoxycarbonyl-6',7'-cyclohexeno-6,7,2',3'-indolomorphinan, 17-allyl-6,7-didehydro-4,5α-epoxy-14β-hydroxy-3-methoxy-4'-methoxycarbonyl-6',7'-cyclohexeno-6,7,2',3'-indolomorphinan, 17-cyclopropylmethyl-6,7-didehydro-4,5α-epoxy-3,14β-dihydroxy-5'-methoxycarbonyl-6',7'-cyclohexeno-6,7,2',3'-indolomorphinan, 17-allyl-6,7-didehydro-4,5α-epoxy-3,14β-dihydroxy-5'-methoxycarbonyl-6',7'-cyclohexeno-6,7,2',3'-indolomorphinan, 17-cyclopropylmethyl-6,7-didehydro-4,5α-epoxy-14β-hydroxy-3-methoxy-5'-methoxycarbonyl-6',7'-cyclohexeno-6,7,2',3'-indolomorphinan, 17-allyl-6,7-didehydro-4,5α-epoxy-14β-hydroxy-3-methoxy-5'-methoxycarbonyl-6',7'-cyclohexeno-6,7,2',3'-indolomorphinan, 17-cyclopropylmethyl-6,7-didehydro-4,5α-epoxy-3,14β-dihydroxy-3"-methoxycarbonyl-6',7'-cyclohexeno-6,7,2',3'-indolomorphinan, 17-allyl-6,7-didehydro-4,5α-epoxy-3,14β-dihydroxy-3"-methoxycarbonyl-6',7'-cyclohexeno-6,7,2',3'-indolomorphinan, 17-cyclopropylmethyl-6,7-didehydro-4,5α-epoxy-14β-hydroxy-3-methoxy-3"-methoxycarbonyl-6',7'-cyclohexeno-6,7,2',3'-indolomorphinan, 17-allyl-6,7-didehydro-4,5α-epoxy-14β-hydroxy-3-methoxy-3"-methoxycarbonyl-6',7'-cyclohexeno-6,7,2',3'-indolomorphinan, 17-cyclopropylmethyl-6,7-didehydro-4,5α-epoxy-3,14β-dihydroxy-4"-methoxycarbonyl-6',7'-cyclohexeno-6,7,2',3'-indolomorphinan, 17-allyl-6,7-didehydro-4,5α-epoxy-3,14β-dihydroxy-4"-methoxycarbonyl-6',7'-cyclohexeno-6,7,2',3'-indolomorphinan, 17-cyclopropylmethyl-6,7-didehydro-4,5α-epoxy-14β-hydroxy-3-methoxy-4"-methoxycarbonyl-6',7'-cyclohexeno-6,7,2',3'-indolomorphinan, 17-allyl-6,7-didehydro-4,5α-epoxy-14β-hydroxy-3-methoxy-4"-methoxycarbonyl-6',7'-cyclohexeno-6,7,2',3'-indolomorphinan, 17-cyclopropylmethyl-6,7-didehydro-4,5α-epoxy-3,14β-dihydroxy-5"-methoxycarbonyl-6',7'-cyclohexeno-6,7,2',3'-indolomorphinan, 17-allyl-6,7-didehydro-4,5α-epoxy-3,14β-dihydroxy-5"-methoxycarbonyl-6',7'-cyclohexeno-6,7,2',3'-indolomorphinan, 17-cyclopropylmethyl-6,7-didehydro-4,5α-epoxy-14β-hydroxy-3-methoxy-5"-methoxycarbonyl-6',7'-cyclohexeno-6,7,2',3'-indolomorphinan, 17-allyl-6,7-didehydro-4,5α-epoxy-14β-hydroxy-3-methoxy-5"-methoxycarbonyl-6',7'-cyclohexeno-6,7,2',3'-indolomorphinan, 17-cyclopropylmethyl-6,7-didehydro-4,5α-epoxy-3,14β-dihydroxy-6"-methoxycarbonyl-6',7'-cyclohexeno-6,7,2',3'-indolomorphinan, 17-allyl-6,7-didehydro-4,5α-epoxy-3,14β-dihydroxy-6"-methoxycarbonyl-6',7'-cyclohexeno-6,7,2',3'-indolomorphinan, 17-cyclopropylmethyl-6,7-didehydro-4,5α-epoxy-14β-hydroxy-3-methoxy-6"-methoxycarbonyl-6',7'-cyclohexeno-6,7,2',3'-indolomorphinan, 17-allyl-6,7-didehydro-4,5α-epoxy-14β-hydroxy-3-methoxy-6"-methoxycarbonyl-6',7'-cyclohexeno-6,7,2',3'-indolomorphinan, 17-cyclopropylmethyl-6,7-didehydro-4,5α-epoxy-3,14β-dihydroxy-4'-methyl-6',7'-benzo-6,7,2',3'-indolomorphinan, 17-allyl-6,7-didehydro-4,5α-epoxy-3,14β-dihydroxy-4'-methyl-6',7'-benzo-6,7,2',3'-indolomorphinan, 17-cyclopropylmethyl-6,7-didehydro-4,5α-epoxy-14β-hydroxy-3-methoxy-4'-methyl-6',7'-benzo-6,7,2',3'-indolomorphinan, 17-allyl-6,7-didehydro-4,5α-epoxy-14β-hydroxy-3-methoxy-4'-methyl-6',7'-benzo-6,7,2',3'-indolomorphinan, 17-cyclopropylmethyl-6,7-didehydro-4,5α-epoxy-3,14β-dihydroxy-5'-methyl-6',7'-benzo-6,7,2',3'-indolomorphinan, 17-allyl-6,7-didehydro-4,5α-epoxy-3,14β-dihydroxy-5'-methyl-6',7'-benzo-6,7,2',3'-indolomorphinan, 17-cyclopropylmethyl-6,7-didehydro-4,5α-epoxy-14β-hydroxy-3-methoxy-5'-methyl-6',7'-benzo-6,7,2',3'-indolomorphinan, 17-allyl-6,7-didehydro-4,5α-epoxy-14β-hydroxy-3-methoxy-5'-methyl-6',7'-benzo-6,7,2',3'-indolomorphinan, 17-cyclopropylmethyl-6,7-didehydro-4,5α-epoxy-3,14β-dihydroxy-3"-methyl-6',7'-benzo-6,7,2',3'-indolomorphinan, 17-allyl-6,7-didehydro-4,5α-epoxy-3,14β-dihydroxy-3"-methyl-6',7'-benzo-6,7,2',3'-indolomorphinan, 17-cyclopropylmethyl-6,7-didehydro-4,5α-epoxy-14β-hydroxy-3-methoxy-3"-methyl-6',7'-benzo-6,7,2',3'-indolomorphinan, 17-allyl-6,7-didehydro-4,5α-epoxy-14β-hydroxy-3-methoxy-3"-methyl-6',7'-benzo-6,7,2',3'-indolomorphinan, 17-cyclopropylmethyl-6,7-didehydro-4,5α-epoxy-3,14β-dihydroxy-4"-methyl-6',7'-benzo-6,7,2',3'-indolomorphinan, 17-allyl-6,7-didehydro-4,5α-epoxy-3,14β-dihydroxy-4"-methyl-6',7'-benzo-6,7,2',3'-indolomorphinan, 17-cyclopropylmethyl-6,7-didehydro-4,5α-epoxy-14β-hydroxy-3-methoxy-4"-methyl-6',7'-benzo-6,7,2',3'-indolomorphinan, 17-allyl-6,7-didehydro-4,5α-epoxy-14β-hydroxy-3-methoxy-4"-methyl-6',7'-benzo-6,7,2',3'-indolomorphinan, 17-cyclopropylmethyl-6,7-didehydro-4,5α-epoxy-3,14β-dihydroxy-5"-methyl-6',7'-benzo-6,7,2',3'-indolomorphinan, 17-allyl-6,7-didehydro-4,5α-epoxy-3,14β-dihydroxy-5"-methyl-6',7'-benzo-6,7,2',3'-indolomorphinan, 17-cyclopropylmethyl-6,7-didehydro-4,5α-epoxy-14β-hydroxy-3-methoxy-5"-methyl-6',7'-benzo-6,7,2',3'-indolomorphinan, 17-allyl-6,7-didehydro-4,5α-epoxy-14β-hydroxy-3-methoxy-5"-methyl-6',7'-benzo-6,7,2',3'-indolomorphinan, 17-cyclopropylmethyl-6,7-didehydro-4,5α-epoxy-3,14β-dihydroxy-6"-methyl-6',7'-benzo-6,7,2',3'-indolomorphinan, 17-allyl-6,7-didehydro-4,5α-epoxy-3,14β-dihydroxy-6"-methyl-6',7'-benzo-6,7,2',3'-indolomorphinan, 17-cyclopropylmethyl-6,7-didehydro-4,5α-epoxy-14β-hydroxy-3-methoxy-6"-methyl-6',7'-benzo-6,7,2',3'-indolomorphinan, 17-allyl-6,7-didehydro-4,5α-epoxy-14β-hydroxy-3-methoxy-6"-methyl-6',7'-benzo-6,7,2',3'-indolomorphinan, 17-cyclopropylmethyl-6,7-didehydro-4,5α-epoxy-3,14β-dihydroxy-4'-bromo-6',7'-benzo-6,7,2',3'-indolomorphinan, 17-allyl-6,7-didehydro-4,5α-epoxy-3,14β-dihydroxy-4'-bromo-6',7'-benzo-6,7,2',3'-indolomorphinan, 17-cyclopropylmethyl-6,7-didehydro-4,5α-epoxy-14β-hydroxy-3-methoxy-4'-bromo-6',7'-benzo-6,7,2',3'-indolomorphinan, 17-allyl-6,7-didehydro-4,5α-epoxy-14β-hydroxy-3-methoxy-4'-bromo-6',7'-benzo-6,7,2',3'-indolomorphinan, 17-cyclopropylmethyl-6,7-didehydro-4,5α-epoxy-3,14β-dihydroxy-5'-bromo-6',7'-benzo-6,7,2',3'-indolomorphinan, 17-allyl-6,7-didehydro-4,5α-epoxy-3,14β-dihydroxy-5'-bromo-6',7'-benzo-6,7,2',3'-indolomorphinan, 17-cyclopropylmethyl-6,7-didehydro-4,5α-epoxy-14β-hydroxy-3-methoxy-5'-bromo-6',7'-benzo-6,7,2',3'-indolomorphinan, 17-allyl-6,7-didehydro-4,5α-epoxy-14β-hydroxy-3-methoxy-5'-bromo-6',7'-benzo-6,7,2',3'-indolomorphinan, 17-cyclopropylmethyl-6,7-didehydro-4,5α-epoxy-3,14β-dihydroxy-3"-bromo-6',7'-benzo-6,7,2',3'-indolomorphinan, 17-allyl-6,7-didehydro-4,5α-epoxy-3,14β-dihydroxy-3"-bromo-6',7'-benzo-6,7,2',3'-indolomorphinan, 17-cyclopropylmethyl-6,7-didehydro-4,5α-epoxy-14β-hydroxy-3-methoxy-3"-bromo-6',7'-benzo-6,7,2',3'-indolomorphinan, 17-allyl-6,7-didehydro-4,5α-epoxy-14β-hydroxy-3-methoxy-3"-bromo-6',7'-benzo-6,7,2',3'-indolomorphinan, 17-cyclopropylmethyl-6,7-didehydro-4,5α-epoxy-3,14β-dihydroxy-4"-bromo-6',7'-benzo-6,7,2',3'-indolomorphinan, 17-allyl-6,7-didehydro-4,5α-epoxy-3,14β-dihydroxy-4"-bromo-6',7'-benzo-6,7,2',3'-indolomorphinan, 17-cyclopropylmethyl-6,7-didehydro-4,5α-epoxy-14β-hydroxy-3-methoxy-4"-bromo-6',7'-benzo-6,7,2',3'-indolomorphinan, 17-allyl-6,7-didehydro-4,5α-epoxy-14β-hydroxy-3-methoxy-4"-bromo-6',7'-benzo-6,7,2',3'-indolomorphinan, 17-cyclopropylmethyl-6,7-didehydro-4,5α-epoxy-3,14β-dihydroxy-5"-bromo-6',7'-benzo-6,7,2',3'-indolomorphinan, 17-allyl-6,7-didehydro-4,5α-epoxy-3,14β-dihydroxy-5"-bromo-6',7'-benzo-6,7,2',3'-indolomorphinan, 17-cyclopropylmethyl-6,7-didehydro-4,5α-epoxy-14β-hydroxy-3-methoxy-5"-bromo-6',7'-benzo-6,7,2',3'-indolomorphinan, 17-allyl-6,7-didehydro-4,5α-epoxy-14β-hydroxy-3-methoxy-5"-bromo-6',7'-benzo-6,7,2',3'-indolomorphinan, 17-cyclopropylmethyl-6,7-didehydro-4,5α-epoxy-3,14β-dihydroxy-6"-bromo-6',7'-benzo-6,7,2',3'-indolomorphinan, 17-allyl-6,7-didehydro-4,5α-epoxy-3,14β-dihydroxy-6"-bromo-6',7'-benzo-6,7,2',3'-indolomorphinan, 17-cyclopropylmethyl-6,7-didehydro-4,5α-epoxy-14β-hydroxy-3-methoxy-6"-bromo-6',7'-benzo-6,7,2',3'-indolomorphinan, 17-allyl-6,7-didehydro-4,5α-epoxy-14β-hydroxy-3-methoxy-6"-bromo-6',7'-benzo-6,7,2',3'-indolomorphinan, 17-cyclopropylmethyl-6,7-didehydro-4,5α-epoxy-3,14β-dihydroxy-4'-methoxy-6',7'-benzo-6,7,2',3'-indolomorphinan, 17-allyl-6,7-didehydro-4,5α-epoxy-3,14β-dihydroxy-4'-methoxy-6',7'-benzo-6,7,2', 3'-indolomorphinan, 17-cyclopropylmethyl-6,7-didehydro-4,5α-epoxy-14β-hydroxy-3,4'-dimethoxy-6',7'-benzo-6,7,2',3'-indolomorphinan, 17-allyl-6,7-didehydro-4,5α-epoxy-14β-hydroxy-3,4'-dimethoxy-6',7'-benzo-6,7,2',3'-indolomorphinan, 17-cyclopropylmethyl-6,7-didehydro-4,5α-epoxy-3,14β-dihydroxy-5'-methoxy-6',7'-benzo-6,7,2',3'-indolomorphinan, 17-allyl-6,7-didehydro-4,5α-epoxy-3,14β-dihydroxy-5'-methoxy-6',7'-benzo-6,7,2',3'-indolomorphinan, 17-cyclopropylmethyl-6,7-didehydro-4,5α-epoxy-14β-hydroxy-3,5'-dimethoxy-6',7'-benzo-6,7,2',3'-indolomorphinan, 17-allyl-6,7-didehydro-4,5α-epoxy-14β-hydroxy-3,5'-dimethoxy-6',7'-benzo-6,7,2',3'-indolomorphinan, 17-cyclopropylmethyl-6,7-didehydro-4,5α-epoxy-3,14β-dihydroxy-3"-methoxy-6',7'-benzo-6,7,2',3'-indolomorphinan, 17-allyl-6,7-didehydro-4,5α-epoxy-3,14β-dihydroxy-3"-methoxy-6',7'-benzo-6,7,2',3'-indolomorphinan, 17-cyclopropylmethyl-6,7-didehydro-4,5α-epoxy-14β-hydroxy-3,3"-dimethoxy-6',7'-benzo-6,7,2',3'-indolomorphinan, 17-allyl-6,7-didehydro-4,5α-epoxy-14β-hydroxy-3,3"-dimethoxy-6',7'-benzo-6,7,2',3'-indolomorphinan, 17-cyclopropylmethyl-6,7-didehydro-4,5α-epoxy-3,14β-dihydroxy-4"-methoxy-6',7'-benzo-6,7,2',3'-indolomorphinan, 17-allyl-6,7-didehydro-4,5α-epoxy-3,14β-dihydroxy-4"-methoxy-6',7'-benzo-6,7,2',3'-indolomorphinan, 17-cyclopropylmethyl-6,7-didehydro-4,5α-epoxy-14β-hydroxy-3,4"-dimethoxy-6',7'-benzo-6,7,2',3'-indolomorphinan, 17-allyl-6,7-didehydro-4,5α-epoxy-14β-hydroxy-3,4"-dimethoxy-6',7'-benzo-6,7,2',3'-indolomorphinan, 17-cyclopropylmethyl-6,7-didehydro-4,5α-epoxy-3,14β-dihydroxy-5"-methoxy-6',7'-benzo-6,7,2',3'-indolomorphinan, 17-allyl-6,7-didehydro-4,5α-epoxy-3,14β-dihydroxy-5"-methoxy-6',7'-benzo-6,7,2',3'-indolomorphinan, 17-cyclopropylmethyl-6,7-didehydro-4,5α-epoxy-14β-hydroxy-3,5"-dimethoxy-6',7'-benzo-6,7,2',3'-indolomorphinan, 17-allyl-6,7-didehydro-4,5α-epoxy-14β-hydroxy-3,5"-dimethoxy-6',7'-benzo-6,7,2',3'-indolomorphinan, 17-cyclopropylmethyl-6,7-didehydro-4,5α-epoxy-3,14β-dihydroxy-6"-methoxy-6',7'-benzo-6,7,2',3'-indolomorphinan, 17-allyl-6,7-didehydro-4,5α-epoxy-3,14β-dihydroxy-6,'-methoxy-6',7'-benzo-6,7,2',3'-indolomorphinan, 17-cyclopropylmethyl-6,7-didehydro-4,5α-epoxy-14β-hydroxy-3,6"-dimethoxy-6',7'-benzo-6,7,2',3'-indolomorphinan, 17-allyl-6,7-didehydro-4,5α-epoxy-14β-hydroxy-3,6"-dimethoxy-6',7'-benzo-6,7,2',3'-indolomorphinan, 17-cyclopropylmethyl-6,7-didehydro-4,5α-epoxy-3,14β-dihydroxy-4'-nitro-6',7'-benzo-6,7,2',3'-indolomorphinan, 17-allyl-6,7-didehydro-4,5α-epoxy-3,14β-dihydroxy-4'-nitro-6',7'-benzo-6,7,2',3'-indolomorphinan, 17-cyclopropylmethyl-6,7-didehydro-4,5α-epoxy-14β-hydroxy-3-methoxy-4'-nitro-6',7'-benzo-6,7,2',3'-indolomorphinan, 17-allyl-6,7-didehydro-4,5α-epoxy-14β-hydroxy-3-methoxy-4'-nitro-6',7'-benzo-6,7,2',3'-indolomorphinan, 17-cyclopropylmethyl-6,7-didehydro-4,5α-epoxy-3,14β-dihydroxy-5'-nitro-6',7'-benzo-6,7,2',3'-indolomorphinan, 17-allyl-6,7-didehydro-4,5α-epoxy-3,14β-dihydroxy-5'-nitro-6',7'-benzo-6,7,2',3'-indolomorphinan, 17-cyclopropylmethyl-6,7-didehydro-4,5α-epoxy-14β-hydroxy-3-methoxy-5'-nitro-6',7'-benzo-6,7,2',3'-indolomorphinan, 17-allyl-6,7-didehydro-4,5α-epoxy-14β-hydroxy-3-methoxy-5'-nitro-6',7'-benzo-6,7,2',3'-indolomorphinan, 17-cyclopropylmethyl-6,7-didehydro-4,5α-epoxy-3,14β-dihydroxy-3"-nitro-6',7'-benzo-6,7,2',3'-indolomorphinan, 17-allyl-6,7-didehydro-4,5α-epoxy-3,14β-dihydroxy-3"-nitro-6',7'-benzo-6,7,2',3'-indolomorphinan, 17-cyclopropylmethyl-6,7-didehydro-4,5α-epoxy-14β-hydroxy-3-methoxy-3"-nitro-6',7'-benzo-6,7,2',3'-indolomorphinan, 17-allyl-6,7-didehydro-4,5α-epoxy-14β-hydroxy-3-methoxy-3"-nitro-6',7'-benzo-6,7,2',3'-indolomorphinan, 17-cyclopropylmethyl-6,7-didehydro-4,5α-epoxy-3,14β-dihydroxy-4"-nitro-6',7'-benzo-6,7,2',3'-indolomorphinan, 17-allyl-6,7-didehydro-4,5α-epoxy-3,14β-dihydroxy-4"-nitro-6',7'-benzo-6,7,2',3'-indolomorphinan, 17-cyclopropylmethyl-6,7-didehydro-4,5α-epoxy-14β-hydroxy-3-methoxy-4"-nitro-6',7'-benzo-6,7,2',3'-indolomorphinan, 17-allyl-6,7-didehydro-4,5α-epoxy-14β-hydroxy-3-methoxy-4"-nitro-6',7'-benzo-6,7,2',3'-indolomorphinan, 17-cyclopropylmethyl-6,7-didehydro-4,5α-epoxy-3,14β-dihydroxy-5"-nitro-6',7'-benzo-6,7,2',3'-indolomorphinan, 17-allyl-6,7-didehydro-4,5α-epoxy-3,14β-dihydroxy-5,'-nitro-6',7'-benzo-6,7,2',3'-indolomorphinan, 17-cyclopropylmethyl-6,7-didehydro-4,5α-epoxy-14β-hydroxy-3-methoxy-5"-nitro-6',7'-benzo-6,7,2',3'-indolomorphinan, 17-allyl-6,7-didehydro-4,5α-epoxy-14β-hydroxy-3-methoxy-5"-nitro-6',7'-benzo-6,7,2',3'-indolomorphinan, 17-cyclopropylmethyl-6,7-didehydro-4,5α-epoxy-3,14β-dihydroxy-6"-nitro-6',7'-benzo-6,7,2',3'-indolomorphinan, 17-allyl-6,7-didehydro-4,5α-epoxy-3,14β-dihydroxy-6"-nitro-6',7'-benzo-6,7,2',3'-indolomorphinan, 17-cyclopropylmethyl-6,7-didehydro-4,5α-epoxy-14β-hydroxy-3-methoxy-6"-nitro-6',7'-benzo-6,7,2',3'-indolomorphinan, 17-allyl-6,7-didehydro-4,5α-epoxy-14β-hydroxy-3-methoxy-6"-nitro-6',7'-benzo-6,7,2',3'-indolomorphinan, 17-cyclopropylmethyl-6,7-didehydro-4,5α-epoxy-3,14β-dihydroxy-4'-methoxycarbonyl-6',7'-benzo-6,7,2',3'-indolomorphinan, 17-allyl-6,7-didehydro-4,5α-epoxy-3,14β-dihydroxy-4'-methoxycarbonyl-6',7'-benzo-6,7,2',3'-indolomorphinan, 17-cyclopropylmethyl-6,7-didehydro-4,5α-epoxy-14β-hydroxy-3-methoxy-4'-methoxycarbonyl-6',7'-benzo-6,7,2',3'-indolomorphinan, 17-allyl-6,7-didehydro-4,5α-epoxy-14β-hydroxy-3-methoxy-4'-methoxycarbonyl-6',7'-benzo-6,7,2',3'-indolomorphinan, 17-cyclopropylmethyl-6,7-didehydro-4,5α-epoxy-3,14β-dihydroxy-5'-methoxycarbonyl-6',7'-benzo-6,7,2',3'-indolomorphinan, 17-allyl-6,7-didehydro-4,5α-epoxy-3,14β-dihydroxy-5'-methoxycarbonyl-6',7'-benzo-6,7,2',3'-indolomorphinan, 17-cyclopropylmethyl-6,7-didehydro-4,5α-epoxy-14β-hydroxy-3-methoxy-5'-methoxycarbonyl-6',7'-benzo-6,7,2',3'-indolomorphinan, 17-allyl-6,7-didehydro-4,5α-epoxy-14β-hydroxy-3-methoxy-5'-methoxycarbonyl-6',7'-benzo-6,7,2',3'-indolomorphinan, 17-cyclopropylmethyl-6,7-didehydro-4,5α-epoxy-14β-dihydroxy-3"-methoxycarbonyl-6',7'-benzo-6,7,2',3'-indolomorphinan, 17-allyl-6,7-didehydro-4,5α-epoxy-3,14β-dihydroxy-3"-methoxycarbonyl-6',7'-benzo-6,7,2',3'-indolomorphinan, 17-cyclopropylmethyl-6,7-didehydro-4,5α-epoxy-14β-hydroxy-3-methoxy-3"-methoxycarbonyl-6',7'-benzo-6,7,2',3'-indolomorphinan, 17-allyl-6,7-didehydro-4,5α-epoxy-14β-hydroxy-3-methoxy-3"-methoxycarbonyl-6',7'-benzo-6,7,2',3'-indolomorphinan, 17-cyclopropylmethyl-6,7-didehydro-4,5α-epoxy-3,14β-dihydroxy-4"-methoxycarbonyl-6',7'-benzo-6,7,2',3'-indolomorphinan, 17-allyl-6,7-didehydro-4,5α-epoxy-3,14β-dihydroxy-4"-methoxycarbonyl-6',7'-benzo-6,7,2',3'-indolomorphinan, 17-cyclopropylmethyl-6,7-didehydro-4,5α-epoxy-14β-hydroxy-3-methoxy-4"-methoxycarbonyl-6',7'-benzo-6,7,2',3'-indolomorphinan, 17-allyl-6,7-didehydro-4,5α-epoxy-14β-hydroxy-3-
  methoxy-4"-methoxycarbonyl-6',7'-benzo-6,7,2',3'-
  indolomorphinan,
17-cyclopropylmethyl-6,7-didehydro-4,5α-epoxy-3,14β-
  dihydroxy-5"-methoxycarbonyl-6',7'-benzo-6,7,2',3'-
  indolomorphinan,
17-allyl-6,7-didehydro-4,5α-epoxy-3,14β-dihydroxy-5"-
  methoxycarbonyl-6',7'-benzo-6,7,2',3'-indolomorphinan,
17-cyclopropylmethyl-6,7-didehydro-4,5α-epoxy-14β-
  hydroxy-3-methoxy-5"-methoxycarbonyl-6',7'-benzo-6,
  7,2',3'-indolomorphinan,
17-allyl-6,7-didehydro-4,5α-epoxy-14β-hydroxy-3-
  methoxy-5"-methoxycarbonyl-6',7'-benzo-6,7,2',3'-
  indolomorphinan,
17-cyclopropylmethyl-6,7-didehydro-4,5α-epoxy-3,14β-
  dihydroxy-6"-methoxycarbonyl-6',7'-benzo-6,7,2',3'-
  indolomorphinan,
17-allyl-6,7-didehydro-4,5α-epoxy-3,14β-dihydroxy-6"-
  methoxycarbonyl-6',7'-benzo-6,7,2',3'-indolomorphinan,
17-cyclopropylmethyl-6,7-didehydro-4,5α-epoxy-14β-
  hydroxy-3-methoxy-6"-methoxycarbonyl-6',7'-benzo-6,
  7,2',3'-indolomorphinan,
17-allyl-6,7-didehydro-4,5α-epoxy-14β-hydroxy-3-
  methoxy-6"-methoxycarbonyl-6',7'-benzo-6,7,2',3'-
  indolomorphinan,
17-cyclopropylmethyl-6,7-didehydro-4,5α-epoxy-3,14β-
  dihydroxy-4'-methyl-[6',7'-b]-pyrido-6,7,2',3'-
  indolomorphinan,
17-allyl-6,7-didehydro-4,5α-epoxy-3,14β-dihydroxy-4'-
  methyl-[6',7'-b]-pyrido-6,7,2',3'-indolomorphinan,
17-cyclopropylmethyl-6,7-didehydro-4,5α-epoxy-14β-
  hydroxy-3-methoxy-4'-methyl-[6',7'-b]-pyrido-6,7,2',3'-
  indolomorphinan,
17-allyl-6,7-didehydro-4,5α-epoxy-14β-hydroxy-3-
  methoxy-4'-methyl-[6',7'-b]-pyrido-6,7,2',3'-
  indolomorphinan,
17-cyclopropylmethyl-6,7-didehydro-4,5α-epoxy-3,14β-
  dihydroxy-5'-methyl-[6',7'-b]-pyrido-6,7,2',3'-
  indolomorphinan,
17-allyl-6,7-didehydro-4,5α-epoxy-3,14β-dihydroxy-5'-
  methyl-[6',7'-b]-pyrido-6,7,2',3'-indolomorphinan,
17-cyclopropylmethyl-6,7-didehydro-4,5α-epoxy-14β-
  hydroxy-3-methoxy-5'-methyl-[6',7'-b]-pyrido-6,7,2',3'-
  indolomorphinan,
17-allyl-6,7-didehydro-4,5α-epoxy-14β-hydroxy-3-
  methoxy-5'-methyl-[6',7'-b]-pyrido-6,7,2',3'-
  indolomorphinan,
17-cyclopropylmethyl-6,7-didehydro-4,5α-epoxy-3,14β-
  dihydroxy-4"-methyl-[6',7'-b]-pyrido-6,7,2',3'-
  indolomorphinan,
17-allyl-6,7-didehydro-4,5α-epoxy-3,14β-dihydroxy-4"-
  methyl-[6',7'-b]-pyrido-6,7,2',3'-indolomorphinan,
17-cyclopropylmethyl-6,7-didehydro-4,5α-epoxy-14β-
  hydroxy-3-methoxy-4"-methyl-[6',7'-b]-pyrido-6,7,2',3'-
  indolomorphinan,
17-allyl-6,7-didehydro-4,5α-epoxy-14β-hydroxy-3-
  methoxy-4"-methyl-[6',7'-b]-pyrido-6,7,2',3'-
  indolomorphinan,
17-cyclopropylmethyl-6,7-didehydro-4,5α-epoxy-3,14β-
  dihydroxy-5"-methyl-[6',7'-b]-pyrido-6,7,2',3'-
  indolomorphinan,
17-allyl-6,7-didehydro-4,5α-epoxy-3,14β-dihydroxy-5"-
  methyl-[6',7'-b]-pyrido-6,7,2',3'-indolomorphinan,
17-cyclopropylmethyl-6,7-didehydro-4,5α-epoxy-14β-
  hydroxy-3-methoxy-5"-methyl-[6',7'-b]-pyrido-6,7,2',3'-
  indolomorphinan,
17-allyl-6,7-didehydro-4,5α-epoxy-14β-hydroxy-3-
  methoxy-5"-methyl-[6',7'-b]-pyrido-6,7,2',3'-
  indolomorphinan,
17-cyclopropylmethyl-6,7-didehydro-4,5α-epoxy-3,14β-
  dihydroxy-6"-methyl-[6',7'-b]-pyrido-6,7,2',3'-
  indolomorphinan,
17-allyl-6,7-didehydro-4,5α-epoxy-3,14β-dihydroxy-6"-
  methyl-[6',7'-b]-pyrido-6,7,2',3'-indolomorphinan,
17-cyclopropylmethyl-6,7-didehydro-4,5α-epoxy-14β-
  hydroxy-3-methoxy-6"-methyl-[6',7'-b]-pyrido-6,7,2',3'-
  indolomorphinan,
17-allyl-6,7-didehydro-4,5α-epoxy-14β-hydroxy-3-
  methoxy-6"-methyl-[6',7'-b]-pyrido-6,7,2',3'-
  indolomorphinan,
17-cyclopropylmethyl-6,7-didehydro-4,5α-epoxy-3,14β-
  dihydroxy-4'-bromo-[6',7'-b]-pyrido-6,7,2',3'-
  indolomorphinan,
17-allyl-6,7-didehydro-4,5α-epoxy-3,14β-dihydroxy-4'-
  bromo-[6',7'-b]-pyrido-6,7,2',3'-indolomorphinan,
17-cyclopropylmethyl-6,7-didehydro-4,5α-epoxy-14β-
  hydroxy-3-methoxy-4'-bromo-[6',7'-b]-pyrido-6,7,2',3'-
  indolomorphinan,
17-allyl-6,7-didehydro-4,5α-epoxy-14β-hydroxy-3-
  methoxy-4'-bromo-[6',7'-b]-pyrido-6,7,2',3'-
  indolomorphinan,
17-cyclopropylmethyl-6,7-didehydro-4,5α-epoxy-3,14β-
  dihydroxy-5'-bromo-[6',7'-b]-pyrido-6,7,2',3'-
  indolomorphinan,
17-allyl-6,7-didehydro-4,5α-epoxy-3,14β-dihydroxy-5'-
  bromo-[6',7'-b]-pyrido-6,7,2',3'-indolomorphinan,
17-cyclopropylmethyl-6,7-didehydro-4,5α-epoxy-14β-
  hydroxy-3-methoxy-5'-bromo-[6',7'-b]-pyrido-6,7,2',3'-
  indolomorphinan,
17-allyl-6,7-didehydro-4,5α-epoxy-14β-hydroxy-3-
  methoxy-5'-bromo-[6',7'-b]-pyrido-6,7,2',3'-
  indolomorphinan,
17-cyclopropylmethyl-6,7-didehydro-4,5α-epoxy-3,14β-
  dihydroxy-4"-bromo-[6',7'-b]-pyrido-6,7,2',3'-
  indolomorphinan,
17-allyl-6,7-didehydro-4,5α-epoxy-3,14β-dihydroxy-4"-
  bromo-[6',7'-b]-pyrido-6,7,2',3'-indolomorphinan,
17-cyclopropylmethyl-6,7-didehydro-4,5α-epoxy-14β-
  hydroxy-3-methoxy-4"-bromo-[6',7'-b]-pyrido-6,7,2',3'-
  indolomorphinan,
17-allyl-6,7-didehydro-4,5α-epoxy-14β-hydroxy-3-
  methoxy-4"-bromo-[6',7'-b]-pyrido-6,7,2',3'-
  indolomorphinan,
17-cyclopropylmethyl-6,7-didehydro-4,5=-epoxy-3,14β-
  dihydroxy-5"-bromo-[6',7'-b]-pyrido-6,7,2',3'-
  indolomorphinan,
17-allyl-6,7-didehydro-4,5α-epoxy-3,14β-dihydroxy-5"-
  bromo-[6',7'-b]-pyrido-6,7,2',3'-indolomorphinan,
17-cyclopropylmethyl-6,7-didehydro-4,5α-epoxy-14β-
  hydroxy-3-methoxy-5"-bromo-[6',7'-b]-pyrido-6,7,2',3'-
  indolomorphinan,
17-allyl-6,7-didehydro-4,5α-epoxy-14β-hydroxy-3-
  methoxy-5"-bromo-[6',7'-b]-pyrido-6,7,2',3'-
  indolomorphinan,
17-cyclopropylmethyl-6,7-didehydro-4,5α-epoxy-3,14β-
  dihydroxy-6"-bromo-[6',7'-b]-pyrido-6,7,2',3'-
  indolomorphinan,
17-allyl-6,7-didehydro-4,5α-epoxy-3,14β-dihydroxy-6"-
  bromo-[6',7'-b]-pyrido-6,7,2',3'-indolomorphinan,
17-cyclopropylmethyl-6,7-didehydro-4,5α-epoxy-14β-
  hydroxy-3-methoxy-6"-bromo-[6',7'-b]-pyrido-6,7,2',3'-
  indolomorphinan,
17-allyl-6,7-didehydro-4,5α-epoxy-14β-hydroxy-3-
  methoxy-6"-bromo-[6',7'-b]-pyrido-6,7,2',3'-
  indolomorphinan,
17-cyclopropylmethyl-6,7-didehydro-4,5α-epoxy-3,14β-
  dihydroxy-4'-methoxy-[6',7'-b]-pyrido-6,7,2',3'-
  indolomorphinan, 17-allyl-6,7-didehydro-4,5α-epoxy-3,14β-dihydroxy-4'-methoxy-[6',7'-b]-pyrido-6,7,2',3'-indolomorphinan, 17-cyclopropylmethyl-6,7-didehydro-4,5α-epoxy-14β-hydroxy-3,4'-dimethoxy-[6',7'-b]-pyrido-6,7,2',3'-indolomorphinan, 17-allyl-6,7-didehydro-4,5α-epoxy-14β-hydroxy-3,4'-dimethoxy-[6',7'-b]-pyrido-6,7,2',3'-indolomorphinan, 17-cyclopropylmethyl-6,7-didehydro-4,5α-epoxy-3,14β-dihydroxy-5'-methoxy-[6',7'-b]-pyrido-6,7,2',3'-indolomorphinan, 17-allyl-6,7-didehydro-4,5α-epoxy-3,14β-dihydroxy-5'-methoxy-[6',7'-b]-pyrido-6,7,2',3'-indolomorphinan, 17-cyclopropylmethyl-6,7-didehydro-4,5α-epoxy-14β-hydroxy-3,5'-dimethoxy-[6',7'-b]-pyrido-6,7,2',3'-indolomorphinan, 17-allyl-6,7-didehydro-4,5α-epoxy-14β-hydroxy-3,5'-dimethoxy-[6',7'-b]-pyrido-6,7,2',3'-indolomorphinan, 17-cyclopropylmethyl-6,7-didehydro-4,5α-epoxy-3,14β-dihydroxy-4"-methoxy-[6',7'-b]-pyrido-6,7,2',3'-indolomorphinan, 17-allyl-6,7-didehydro-4,5α-epoxy-3,14β-dihydroxy-4,'-methoxy-[6',7'-b]-pyrido-6,7,2',3'-indolomorphinan, 17-cyclopropylmethyl-6,7-didehydro-4,5α-epoxy-14β-hydroxy-3,4"-dimethoxy-[6',7'-b]-pyrido-6,7,2',3'-indolomorphinan, 17-allyl-6,7-didehydro-4,5α-epoxy-14β-hydroxy-3,4"-dimethoxy-[6',7'-b]-pyrido-6,7,2',3'-indolomorphinan, 17-cyclopropylmethyl-6,7-didehydro-4,5α-epoxy-3,14β-dihydroxy-5"-methoxy-[6',7'-b]-pyrido-6,7,2',3'-indolomorphinan, 17-allyl-6,7-didehydro-4,5α-epoxy-3,14β-dihydroxy-5,'-methoxy-[6',7'-b]-pyrido-6,7,2',3'-indolomorphinan, 17-cyclopropylmethyl-6,7-didehydro-4,5α-epoxy-14β-hydroxy-3,5"-dimethoxy-[6',7'-b]-pyrido-6,7,2',3'-indolomorphinan, 17-allyl-6,7-didehydro-4,5α-epoxy-14β-hydroxy-3,5"-dimethoxy-[6',7'-b]-pyrido-6,7,2',3'-indolomorphinan, 17-cyclopropylmethyl-6,7-didehydro-4,5α-epoxy-3,14β-dihydroxy-6"-methoxy-[6',7'-b]-pyrido-6,7,2',3'-indolomorphinan, 17-allyl-6,7-didehydro-4,5α-epoxy-3,14β-dihydroxy-6"-methoxy-[6',7'-b]-pyrido-6,7,2',3'-indolomorphinan, 17-cyclopropylmethyl-6,7-didehydro-4,5α-epoxy-14β-hydroxy-3,6"-dimethoxy-[6',7'-b]-pyrido-6,7,2',3'-indolomorphinan, 17-allyl-6,7-didehydro-4,5α-epoxy-14β-hydroxy-3,6"-dimethoxy-[6',7'-b]-pyrido-6,7,2',3'-indolomorphinan, 17-cyclopropylmethyl-6,7-didehydro-4,5α-epoxy-3,14β-dihydroxy-4'-nitro-[6',7'-b]-pyrido-6,7,2',3'-indolomorphinan, 17-allyl-6,7-didehydro-4,5α-epoxy-3,14β-dihydroxy-4'-nitro-[6',7'-b]-pyrido-6,7,2',3'-indolomorphinan, 17-cyclopropylmethyl-6,7-didehydro-4,5α-epoxy-14β-hydroxy-3-methoxy-4'-nitro-[6',7'-b]-pyrido-6,7,2',3'-indolomorphinan, 17-allyl-6,7-didehydro-4,5α-epoxy-14β-hydroxy-3-methoxy-4'-nitro-[6',7'-b]-pyrido-6,7,2',3'-indolomorphinan, 17-cyclopropylmethyl-6,7-didehydro-4,5α-epoxy-3,14β-dihydroxy-5'-nitro-[6',7'-b]-pyrido-6,7,2',3'-indolomorphinan, 17-allyl-6,7-didehydro-4,5α-epoxy-3,14β-dihydroxy-5'-nitro-[6',7'-b]-pyrido-6,7,2',3'-indolomorphinan, 17-cyclopropylmethyl-6,7-didehydro-4,5α-epoxy-14β-hydroxy-3-methoxy-5'-nitro-[6',7'-b]-pyrido-6,7,2',3'-indolomorphinan, 17-allyl-6,7-didehydro-4,5α-epoxy-14β-hydroxy-3-methoxy-5'-nitro-[6',7'-b]-pyrido-6,7,2',3'-indolomorphinan, 17-cyclopropylmethyl-6,7-didehydro-4,5α-epoxy-3,14β-dihydroxy-4"-nitro-[6',7'-b]-pyrido-6,7,2',3'-indolomorphinan, 17-allyl-6,7-didehydro-4,5α-epoxy-3,14β-dihydroxy-4"-nitro-[6',7'-b]-pyrido-6,7,2',3'-indolomorphinan, 17-cyclopropylmethyl-6,7-didehydro-4,5α-epoxy-14β-hydroxy-3-methoxy-4"-nitro-[6',7'-b]-pyrido-6,7,2',3'-indolomorphinan, 17-allyl-6,7-didehydro-4,5α-epoxy-14β-hydroxy-3-methoxy-4"-nitro-[6',7'-b]-pyrido-6,7,2',3'-indolomorphinan, 17-cyclopropylmethyl-6,7-didehydro-4,5α-epoxy-3,14β-dihydroxy-5"-nitro-[6',7'-b]-pyrido-6,7,2',3'-indolomorphinan, 17-allyl-6,7-didehydro-4,5α-epoxy-3,14β-dihydroxy-5"-nitro-[6',7'-b]-pyrido-6,7,2',3'-indolomorphinan, 17-cyclopropylmethyl-6,7-didehydro-4,5α-epoxy-14β-hydroxy-3-methoxy-5"-nitro-[6',7'-b]-pyrido-6,7,2',3'-indolomorphinan, 17-allyl-6,7-didehydro-4,5α-epoxy-14β-hydroxy-3-methoxy-5"-nitro-[6',7'-b]-pyrido-6,7,2',3'-indolomorphinan, 17-cyclopropylmethyl-6,7-didehydro-4,5α-epoxy-3,14β-dihydroxy-6"-nitro-[6',7'-b]-pyrido-6,7,2',3'-indolomorphinan, 17-allyl-6,7-didehydro-4,5α-epoxy-3,14β-dihydroxy-6"-nitro-[6',7'-b]-pyrido-6,7,2',3'-indolomorphinan, 17-cyclopropylmethyl-6,7-didehydro-4,5α-epoxy-14β-hydroxy-3-methoxy-6"-nitro-[6',7'-b]-pyrido-6,7,2',3'-indolomorphinan, 17-allyl-6,7-didehydro-4,5α-epoxy-14β-hydroxy-3-methoxy-6"-nitro-[6',7'-b]-pyrido-6,7,2',3'-indolomorphinan, 17-cyclopropylmethyl-6,7-didehydro-4,5α-epoxy-3,14β-dihydroxy-4'-methoxycarbonyl-[6',7'-b]-pyrido-6,7,2',3'-indolomorphinan, 17-allyl-6,7-didehydro-4,5α-epoxy-3,14β-dihydroxy-4'-methoxycarbonyl-[6',7'-b]-pyrido-6,7,2',3'-indolomorphinan, 17-cyclopropylmethyl-6,7-didehydro-4,5α-epoxy-14β-hydroxy-3-methoxy-4'-methoxycarbonyl-[6',7'-b]-pyrido-6,7,2',3'-indolomorphinan, 17-allyl-6,7-didehydro-4,5α-epoxy-14β-hydroxy-3-methoxy-4'-methoxycarbonyl-[6',7'-b]-pyrido-6,7,2',3'-indolomorphinan, 17-cyclopropylmethyl-6,7-didehydro-4,5α-epoxy-3,14β-dihydroxy-5'-methoxycarbonyl-[6',7'-b]-pyrido-6,7,2',3'-indolomorphinan, 17-allyl-6,7-didehydro-4,5α-epoxy-3,14β-dihydroxy-5'-methoxycarbonyl-[6',7'-b]-pyrido-6,7,2',3'-indolomorphinan, 17-cyclopropylmethyl-6,7-didehydro-4,5α-epoxy-14β-hydroxy-3-methoxy-5'-methoxycarbonyl-[6',7'-b]-pyrido-6,7,2',3'-indolomorphinan, 17-allyl-6,7-didehydro-4,5α-epoxy-14β-hydroxy-3-methoxy-5'-methoxycarbonyl-[6',7'-b]-pyrido-6,7,2',3'-indolomorphinan, 17-cyclopropylmethyl-6,7-didehydro-4,5α-epoxy-3,14β-dihydroxy-4"-methoxycarbonyl-[6',7'-b]-pyrido-6,7,2',3'-indolomorphinan, 17-allyl-6,7-didehydro-4,5α-epoxy-3,14β-dihydroxy-4"-methoxycarbonyl-[6',7'-b]-pyrido-6,7,2',3'-indolomorphinan, 17-cyclopropylmethyl-6,7-didehydro-4,5α-epoxy-14β-hydroxy-3-methoxy-4"-methoxycarbonyl-[6',7'-b]-pyrido-6,7,2',3'-indolomorphinan, 17-allyl-6,7-didehydro-4,5α-epoxy-14β-hydroxy-3-methoxy-4"-methoxycarbonyl-[6',7'-b]-pyrido-6,7,2',3'-indolomorphinan, 17-cyclopropylmethyl-6,7-didehydro-4,5α-epoxy-3,14β-dihydroxy-5"-methoxycarbonyl-[6',7'-b]-pyrido-6,7,2',3'-indolomorphinan, 17-allyl-6,7-didehydro-4,5α-epoxy-3,14β-dihydroxy-5"-methoxycarbonyl-[6',7'-b]-pyrido-6,7,2',3'-indolomorphinan, 17-cyclopropylmethyl-6,7-didehydro-4,5α-epoxy-14β-hydroxy-3-methoxy-5"-methoxycarbonyl-[6',7'-b]-pyrido-6,7,2',3'-indolomorphinan, 17-allyl-6,7-didehydro-4,5α-epoxy-14β-hydroxy-3-methoxy-5"-methoxycarbonyl-[6',7'-b]-pyrido-6,7,2',3'-indolomorphinan, 17-cyclopropylmethyl-6,7-didehydro-4,5α-epoxy-3,14β-dihydroxy-6"-methoxycarbonyl-[6',7'-b]-pyrido-6,7,2',3'-indolomorphinan, 17-allyl-6,7-didehydro-4,5α-epoxy-3,14β-dihydroxy-6,'-methoxycarbonyl-[6',7'-b]-pyrido-6,7,2',3'-indolomorphinan, 17-cyclopropylmethyl-6,7-didehydro-4,5α-epoxy-14β-hydroxy-3-methoxy-6"-methoxycarbonyl-[6',7'-b]-pyrido-6,7,2',3'-indolomorphinan, 17-allyl-6,7-didehydro-4,5α-epoxy-14β-hydroxy-3-methoxy-6"-methoxycarbonyl-[6',7'-b]-pyrido-6,7,2',3'-indolomorphinan, 17-cyclopropylmethyl-6,7-didehydro-4,5α-epoxy-3,14β-dihydroxy-4'-methyl-[6',7'-c]-pyrido-6,7,2',3'-indolomorphinan, 17-allyl-6,7-didehydro-4,5α-epoxy-3,14β-dihydroxy-4'-methyl-[6',7'-c]-pyrido-6,7,2',3'-indolomorphinan, 17-cyclopropylmethyl-6,7-didehydro-4,5α-epoxy-14β-hydroxy-3-methoxy-4'-methyl-[6',7'-c]-pyrido-6,7,2',3'-indolomorphinan, 17-allyl-6,7-didehydro-4,5α-epoxy-14β-hydroxy-3-methoxy-4'-methyl-[6',7'-c]-pyrido-6,7,2',3'-indolomorphinan, 17-cyclopropylmethyl-6,7-didehydro-4,5α-epoxy-3,14β-dihydroxy-5'-methyl-[6',7'-c]-pyrido-6,7,2',3'-indolomorphinan, 17-allyl-6,7-didehydro-4,5α-epoxy-3,14β-dihydroxy-5'-methyl-[6',7'-c]-pyrido-6,7,2',3'-indolomorphinan, 17-cyclopropylmethyl-6,7-didehydro-4,5α-epoxy-14β-hydroxy-3-methoxy-5'-methyl-[6',7'-c]-pyrido-6,7,2',3'-indolomorphinan, 17-allyl-6,7-didehydro-4,5α-epoxy-14β-hydroxy-3-methoxy-5'-methyl-[6',7'-c]-pyrido-6,7,2',3'-indolomorphinan, 17-cyclopropylmethyl-6,7-didehydro-4,5α-epoxy-3,14β-dihydroxy-2"-methyl-[6',7'-c]-pyrido-6,7,2',3'-indolomorphinan, 17-allyl-6,7-didehydro-4,5α-epoxy-3,14β-dihydroxy-2,'-methyl-[6',7'-c]-pyrido-6,7,2',3'-indolomorphinan, 17-cyclopropylmethyl-6,7-didehydro-4,5α-epoxy-14β-hydroxy-3-methoxy-2"-methyl-[6',7'-c]-pyrido-6,7,2',3'-indolomorphinan, 17-allyl-6,7-didehydro-4,5α-epoxy-14β-hydroxy-3-methoxy-2"-methyl-[6',7'-c]-pyrido-6,7,2',3'-indolomorphinan, 17-cyclopropylmethyl-6,7-didehydro-4,5α-epoxy-3,14β-dihydroxy-5"-methyl-[6',7'-c]-pyrido-6,7,2',3'-indolomorphinan, 17-allyl-6,7-didehydro-4,5α-epoxy-3,14β-dihydroxy-5"-methyl-[6',7'-c]-pyrido-6,7,2',3'-indolomorphinan, 17-cyclopropylmethyl-6,7-didehydro-4,5α-epoxy-14β-hydroxy-3-methoxy-5"-methyl-[6',7'-c]-pyrido-6,7,2',3'-indolomorphinan, 17-allyl-6,7-didehydro-4,5α-epoxy-14β-hydroxy-3-methoxy-5"-methyl-[6',7'-c]-pyrido-6,7,2',3'-indolomorphinan, 17-cyclopropylmethyl-6,7-didehydro-4,5α-epoxy-3,14β-dihydroxy-6"-methyl-[6',7'-c]-pyrido-6,7,2',3'-indolomorphinan, 17-allyl-6,7-didehydro-4,5α-epoxy-3,14β-dihydroxy-6"-methyl-[6',7'-c]-pyrido-6,7,2',3'-indolomorphinan, 17-cyclopropylmethyl-6,7-didehydro-4,5α-epoxy-14β-hydroxy-3-methoxy-6"-methyl-[6',7'-c]-pyrido-6,7,2',3'-indolomorphinan, 17-allyl-6,7-didehydro-4,5α-epoxy-14β-hydroxy-3-methoxy-6"-methyl-[6',7'-c]-pyrido-6,7,2',3'-indolomorphinan, 17-cyclopropylmethyl-6,7-didehydro-4,5α-epoxy-3,14β-dihydroxy-4'-bromo-[6',7'-c]-pyrido-6,7,2',3'-indolomorphinan, 17-allyl-6,7-didehydro-4,5α-epoxy-3,14β-dihydroxy-4'-bromo-[6',7'-c]-pyrido-6,7,2',3'-indolomorphinan, 17-cyclopropylmethyl-6,7-didehydro-4,5α-epoxy-14β-hydroxy-3-methoxy-4'-bromo-[6',7'-c]-pyrido-6,7,2',3'-indolomorphinan, 17-allyl-6,7-didehydro-4,5α-epoxy-14β-hydroxy-3-methoxy-4'-bromo-[6',7'-c]-pyrido-6,7,2',3'-indolomorphinan, 17-cyclopropylmethyl-6,7-didehydro-4,5α-epoxy-3,14β-dihydroxy-5'-bromo-[6',7'-c]-pyrido-6,7,2',3'-indolomorphinan, 17-allyl-6,7-didehydro-4,5α-epoxy-3,14β-dihydroxy-5'-bromo-[6',7'-c]-pyrido-6,7,2',3'-indolomorphinan, 17-cyclopropylmethyl-6,7-didehydro-4,5α-epoxy-14β-hydroxy-3-methoxy-5'-bromo-[6',7'-c]-pyrido-6,7,2',3'-indolomorphinan, 17-allyl-6,7-didehydro-4,5α-epoxy-14β-hydroxy-3-methoxy-5'-bromo-[6',7'-c]-pyrido-6,7,2',3'-indolomorphinan, 17-cyclopropylmethyl-6,7-didehydro-4,5α-epoxy-3,14β-dihydroxy-2"-bromo-[6',7'-c]-pyrido-6,7,2',3'-indolomorphinan, 17-allyl-6,7-didehydro-4,5α-epoxy-3,14β-dihydroxy-2"-bromo-[6',7'-c]-pyrido-6,7,2',3'-indolomorphinan, 17-cyclopropylmethyl-6,7-didehydro-4,5α-epoxy-14β-hydroxy-3-methoxy-2"-bromo-[6',7'-c]-pyrido-6,7,2',3'-indolomorphinan, 17-allyl-6,7-didehydro-4,5α-epoxy-14β-hydroxy-3-methoxy-2"-bromo-[6',7'-c]-pyrido-6,7,2',3'-indolomorphinan, 17-cyclopropylmethyl-6,7-didehydro-4,5α-epoxy-3,14β-dihydroxy-5"-bromo-[6',7'-c]-pyrido-6,7,2',3'-indolomorphinan, 17-allyl-6,7-didehydro-4,5α-epoxy-3,14β-dihydroxy-5"-bromo-[6',7'-c]-pyrido-6,7,2',3'-indolomorphinan, 17-cyclopropylmethyl-6,7-didehydro-4,5α-epoxy-14β-hydroxy-3-methoxy-5"-bromo-[6',7'-c]-pyrido-6,7,2',3'-indolomorphinan, 17-allyl-6,7-didehydro-4,5α-epoxy-14β-hydroxy-3-methoxy-5"-bromo-[6',7'-c]-pyrido-6,7,2',3'-indolomorphinan, 17-cyclopropylmethyl-6,7-didehydro-4,5α-epoxy-3,14β-dihydroxy-6"-bromo-[6',7'-c]-pyrido-6,7,2',3'-indolomorphinan, 17-allyl-6,7-didehydro-4,5α-epoxy-3,14β-dihydroxy-6"-bromo-[6',7'-c]-pyrido-6,7,2',3'-indolomorphinan, 17-cyclopropylmethyl-6,7-didehydro-4,5α-epoxy-14β-hydroxy-3-methoxy-6"-bromo-[6',7'-c]-pyrido-6,7,2',3'-indolomorphinan, 17-allyl-6,7-didehydro-4,5α-epoxy-14β-hydroxy-3-methoxy-6"-bromo-[6',7'-c]-pyrido-6,7,2',3'-indolomorphinan, 17-cyclopropylmethyl-6,7-didehydro-4,5α-epoxy-3,14β-dihydroxy-4'-methoxy-[6',7'-c]-pyrido-6,7,2',3'-indolomorphinan, 17-allyl-6,7-didehydro-4,5α-epoxy-3,14β-dihydroxy-4'-methoxy-[6',7'-c]-pyrido-6,7,2',3'-indolomorphinan, 17-cyclopropylmethyl-6,7-didehydro-4,5α-epoxy-14β-hydroxy-3,4'-dimethoxy-[6',7'-c]-pyrido-6,7,2',3'-indolomorphinan, 17-allyl-6,7-didehydro-4,5α-epoxy-14β-hydroxy-3,4'-dimethoxy-[6',7'-c]-pyrido-6,7,2',3'-indolomorphinan, 17-cyclopropylmethyl-6,7-didehydro-4,5α-epoxy-3,14β-dihydroxy-5'-methoxy-[6',7'-c]-pyrido-6,7,2',3'-indolomorphinan, 17-allyl-6,7-didehydro-4,5α-epoxy-3,14β-dihydroxy-5'-methoxy-[6',7'-c]-pyrido-6,7,2',3'-indolomorphinan, 17-cyclopropylmethyl-6,7-didehydro-4,5α-epoxy-14β-hydroxy-3,5'-dimethoxy-[6',7'-c]-pyrido-6,7,2',3'-indolomorphinan, 17-allyl-6,7-didehydro-4,5α-epoxy-14β-hydroxy-3,5'-dimethoxy-[6',7'-c]-pyrido-6,7,2',3'-indolomorphinan, 17-cyclopropylmethyl-6,7-didehydro-4,5α-epoxy-3,14β-dihydroxy-2"-methoxy-[6',7'-c]-pyrido-6,7,2',3'-indolomorphinan, 17-allyl-6,7-didehydro-4,5α-epoxy-3,14β-dihydroxy-2"-methoxy-[6',7'-c]-pyrido-6,7,2',3'-indolomorphinan, 17-cyclopropylmethyl-6,7-didehydro-4,5α-epoxy-14β-hydroxy-3,2"-dimethoxy-[6',7'-c]-pyrido-6,7,2',3'-indolomorphinan, 17-allyl-6,7-didehydro-4,5α-epoxy-14β-hydroxy-3,2"-dimethoxy-[6',7'-c]-pyrido-6,7,2',3'-indolomorphinan, 17-cyclopropylmethyl-6,7-didehydro-4,5α-epoxy-3,14β-dihydroxy-5"-methoxy-[6',7'-c]-pyrido-6,7,2',3'-indolomorphinan, 17-allyl-6,7-didehydro-4,5α-epoxy-3,14β-dihydroxy-5"-methoxy-[6',7'-c]-pyrido-6,7,2',3'-indolomorphinan, 17-cyclopropylmethyl-6,7-didehydro-4,5α-epoxy-14β-hydroxy-3,5"-dimethoxy-[6',7'-c]-pyrido-6,7,2',3'-indolomorphinan, 17-allyl-6,7-didehydro-4,5α-epoxy-14β-hydroxy-3,5"-dimethoxy-[6',7'-c]-pyrido-6,7,2',3'-indolomorphinan, 17-cyclopropylmethyl-6,7-didehydro-4,5α-epoxy-3,14β-dihydroxy-6"-methoxy-[6',7'-c]-pyrido-6,7,2',3'-indolomorphinan, 17-allyl-6,7-didehydro-4,5α-epoxy-3,14β-dihydroxy-6"-methoxy-[6',7'-c]-pyrido-6,7,2',3'-indolomorphinan, 17-cyclopropylmethyl-6,7-didehydro-4,5α-epoxy-14β-hydroxy-3,6"-dimethoxy-[6',7'-c]-pyrido-6,7,2',3'-indolomorphinan, 17-allyl-6,7-didehydro-4,5α-epoxy-14β-hydroxy-3,6"-dimethoxy-[6',7'-c]-pyrido-6,7,2',3'-indolomorphinan, 17-cyclopropylmethyl-6,7-didehydro-4,5α-epoxy-3,14β-dihydroxy-4'-nitro-[6',7'-c]-pyrido-6,7,2',3'-indolomorphinan, 17-allyl-6,7-didehydro-4,5α-epoxy-3,14β-dihydroxy-4'-nitro-[6',7'-c]-pyrido-6,7,2',3'-indolomorphinan, 17-cyclopropylmethyl-6,7-didehydro-4,5α-epoxy-14β-hydroxy-3-methoxy-4'-nitro-[6',7'-c]-pyrido-6,7,2',3'-indolomorphinan, 17-allyl-6,7-didehydro-4,5α-epoxy-14β-hydroxy-3-methoxy-4'-nitro-[6',7'-c]-pyrido-6,7,2',3'-indolomorphinan, 17-cyclopropylmethyl-6,7-didehydro-4,5α-epoxy-3,14β-dihydroxy-5'-nitro-[6',7'-c]-pyrido-6,7,2',3'-indolomorphinan, 17-allyl-6,7-didehydro-4,5α-epoxy-3,14β-dihydroxy-5'-nitro-[6',7'-c]-pyrido-6,7,2',3'-indolomorphinan, 17-cyclopropylmethyl-6,7-didehydro-4,5α-epoxy-14β-hydroxy-3-methoxy-5'-nitro-[6',7'-c]-pyrido-6,7,2',3'-indolomorphinan, 17-allyl-6,7-didehydro-4,5α-epoxy-14β-hydroxy-3-methoxy-5'-nitro-[6',7'-c]-pyrido-6,7,2',3'-indolomorphinan, 17-cyclopropylmethyl-6,7-didehydro-4,5α-epoxy-3,14β-dihydroxy-2"-nitro-[6',7'-c]-pyrido-6,7,2',3'-indolomorphinan, 17-allyl-6,7-didehydro-4,5α-epoxy-3,14β-dihydroxy-2"-nitro-[6',7'-c]-pyrido-6,7,2',3'-indolomorphinan, 17-cyclopropylmethyl-6,7-didehydro-4,5α-epoxy-14β-hydroxy-3-methoxy-2"-nitro-[6',7'-c]-pyrido-6,7,2',3'-indolomorphinan, 17-allyl-6,7-didehydro-4,5α-epoxy-14β-hydroxy-3-methoxy-2"-nitro-[6',7'-c]-pyrido-6,7,2',3'-indolomorphinan, 17-cyclopropylmethyl-6,7-didehydro-4,5α-epoxy-3,14β-dihydroxy-5"-nitro-[6',7'-c]-pyrido-6,7,2',3'-indolomorphinan, 17-allyl-6,7-didehydro-4,5α-epoxy-3,14β-dihydroxy-5"-nitro-[6',7'-c]-pyrido-6,7,2',3'-indolomorphinan, 17-cyclopropylmethyl-6,7-didehydro-4,5α-epoxy-14β-hydroxy-3-methoxy-5"-nitro-[6',7'-c]-pyrido-6,7,2',3'-indolomorphinan, 17-allyl-6,7-didehydro-4,5α-epoxy-14β-hydroxy-3-methoxy-5"-nitro-[6',7'-c]-pyrido-6,7,2',3'-indolomorphinan, 17-cyclopropylmethyl-6,7-didehydro-4,5α-epoxy-3,14β-dihydroxy-6"-nitro-[6',7'-c]-pyrido-6,7,2',3'-indolomorphinan, 17-allyl-6,7-didehydro-4,5α-epoxy-3,14β-dihydroxy-6"-nitro-[6',7'-c]-pyrido-6,7,2',3'-indolomorphinan, 17-cyclopropylmethyl-6,7-didehydro-4,5α-epoxy-14β-hydroxy-3-methoxy-6"-nitro-[6',7'-c]-pyrido-6,7,2',3'-indolomorphinan, 17-allyl-6,7-didehydro-4,5α-epoxy-14β-hydroxy-3-methoxy-6"-nitro-[6',7'-c]-pyrido-6,7,2',3'-indolomorphinan, 17-cyclopropylmethyl-6,7-didehydro-4,5α-epoxy-3,14β-dihydroxy-4'-methoxycarbonyl-[6',7'-c]-pyrido-6,7,2',3'-indolomorphinan, 17-allyl-6,7-didehydro-4,5α-epoxy-3,14β-dihydroxy-4'-methoxycarbonyl-[6',7'-c]-pyrido-6,7,2',3'-indolomorphinan, 17-cyclopropylmethyl-6,7-didehydro-4,5α-epoxy-14β-hydroxy-3-methoxy-4'-methoxycarbonyl-[6',7'-c]-pyrido-6,7,2',3'-indolomorphinan, 17-allyl-6,7-didehydro-4,5α-epoxy-14β-hydroxy-3-methoxy-4'-methoxycarbonyl-[6',7'-c]-pyrido-6,7,2',3'-indolomorphinan, 17-cyclopropylmethyl-6,7-didehydro-4,5α-epoxy-3,14β-dihydroxy-5'-methoxycarbonyl-[6',7'-c]-pyrido-6,7,2',3'-indolomorphinan, 17-allyl-6,7-didehydro-4,5α-epoxy-3,14β-dihydroxy-5'-methoxycarbonyl-[6',7'-c]-pyrido-6,7,2',3'-indolomorphinan, 17-cyclopropylmethyl-6,7-didehydro-4,5α-epoxy-14β-hydroxy-3-methoxy-5'-methoxycarbonyl-[6',7'-c]-pyrido-6,7,2',3'-indolomorphinan, 17-allyl-6,7-didehydro-4,5α-epoxy-14β-hydroxy-3-methoxy-5'-methoxycarbonyl-[6',7'-c]-pyrido-6,7,2',3'-indolomorphinan, 17-cyclopropylmethyl-6,7-didehydro-4,5α-epoxy-3,14β-dihydroxy-2"-methoxycarbonyl-[6',7'-c]-pyrido-6,7,2',3'-indolomorphinan, 17-allyl-6,7-didehydro-4,5α-epoxy-3,14β-dihydroxy-2"-methoxycarbonyl-[6',7'-c]-pyrido-6,7,2',3'-indolomorphinan, 17-cyclopropylmethyl-6,7-didehydro-4,5α-epoxy-14β-hydroxy-3-methoxy-2"-methoxycarbonyl-[6',7'-c]-pyrido-6,7,2',3'-indolomorphinan, 17-allyl-6,7-didehydro-4,5α-epoxy-14β-hydroxy-3-methoxy-2"-methoxycarbonyl-[6',7'-c]-pyrido-6,7,2',3'-indolomorphinan, 17-cyclopropylmethyl-6,7-didehydro-4,5α-epoxy-,14β-dihydroxy-5"-methoxycarbonyl-[6',7'-c]-pyrido-6,7,2',3'-indolomorphinan, 17-allyl-6,7-didehydro-4,5α-epoxy-3,14β-dihydroxy-5"-methoxycarbonyl-[6',7'-c]-pyrido-6,7,2',3'-indolomorphinan, 17-cyclopropylmethyl-6,7-didehydro-4,5α-epoxy-14β-hydroxy-3-methoxy-5"-methoxycarbonyl-[6',7'-c]-pyrido-6,7,2',3'-indolomorphinan, 17-allyl-6,7-didehydro-4,5α-epoxy-14β-hydroxy-3-methoxy-5"-methoxycarbonyl-[6',7'-c]-pyrido-6,7,2',3'-indolomorphinan, 17-cyclopropylmethyl-6,7-didehydro-4,5α-epoxy-3,14β-dihydroxy-6"-methoxycarbonyl-[6',7'-c]-pyrido-6,7,2',3'-indolomorphinan, 17-allyl-6,7-didehydro-4,5α-epoxy-3,14β-dihydroxy-6"-methoxycarbonyl-[6',7'-c]-pyrido-6,7,2',3'-indolomorphinan, 17-cyclopropylmethyl-6,7-didehydro-4,5α-epoxy-14β-hydroxy-3-methoxy-6"-methoxycarbonyl-[6',7'-c]-pyrido-6,7,2',3'-indolomorphinan, and 17-allyl-6,7-didehydro-4,5α-epoxy-14β-hydroxy-3-methoxy-6"-methoxycarbonyl-[6',7'-c]-pyrido-6,7,2',3'-indolomorphinan.

Further, among the compounds represented by formula (Ib), the compound wherein $R^1$ is cyclopropylmethyl, $R^2$ and $R^3$ are hydroxy and $R^7$ is hydrogen, that is, the Compound 3 of the formula:

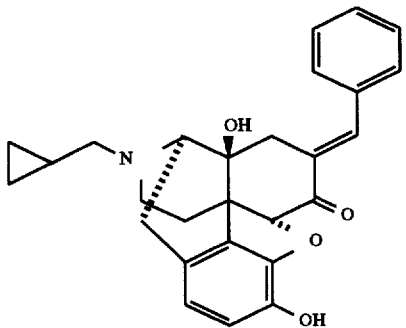

3 that is, 17-cyclopropylmethyl-4,5α-epoxy-3,14β-dihydroxy-6-keto-7-benzylidene-morphinan (benzylidenenaltrexone: abbreviated BNTX) is also a preferred compound.

Further, among the compounds of the formula (Ic), the compound wherein $R^1$ is cyclopropylmethyl, $R^2$ and $R^3$ are hydroxy, and $R^4$, $R^5$, $R^6$ and $R^7$ are hydrogen, that is, the Compound 4 of the formula:

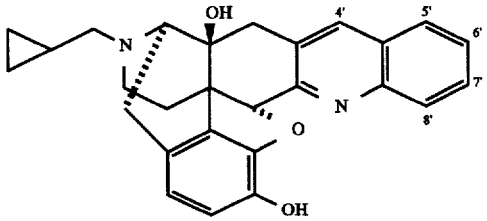

4 is named
17-cyclopropylmethyl-6,7-didehydro-4,5α-epoxy-3,14β-dihydroxy-6,7,2',3'-quinolinomorphinan.

According to this nomenclature, specific examples of the compounds according to the present invention include
17-allyl-6,7-didehydro-4,5α-epoxy-3,14β-dihydroxy-6,7,2',3'-quinolinomorphinan, 17-cyclopropylmethyl-6,7-didehydro-4,5α-epoxy-14β-hydroxy-3-methoxy-6,7,2',3'-quinolinomorphinan, 17-allyl-6,7-didehydro-4,5α-epoxy-14β-hydroxy-3-methoxy-6,7,2',3'-quinolinomorphinan, 17-cyclopropylmethyl-6,7-didehydro-4,5α-epoxy-3,14β-dihydroxy-6,7,2',3'-quinoxalinomorphinan, 17-allyl-6,7-didehydro-4,5α-epoxy-3,14β-dihydroxy-6,7,2',3'-quinoxalinomorphinan, 17-cyclopropylmethyl-6,7-didehydro-4,5α-epoxy-14β-hydroxy-3-methoxy-6,7,2',3'-quinoxalinomorphinan, 17-allyl-6,7-didehydro-4,5α-epoxy-14β-hydroxy-3-methoxy-6,7,2',3'-quinoxalinomorphinan, 17-cyclopropylmethyl-6,7-didehydro-4,5α-epoxy-3,14β-dihydroxy-5'-methyl-6,7,2',3'-quinolinomorphinan, 17-allyl-6,7-didehydro-4,5α-epoxy-3,14β-dihydroxy-5'-methyl-6,7,2',3'-quinolinomorphinan, 17-cyclopropylmethyl-6,7-didehydro-4,5α-epoxy-14β-hydroxy-3-methoxy-5'-methyl-6,7,2',3'-quinolinomorphinan, 17-allyl-6,7-didehydro-4,5α-epoxy-14β-hydroxy-3-methoxy-5'-methyl-6,7,2',3'-quinolinomorphinan, 17-cyclopropylmethyl-6,7-didehydro-4,5α-epoxy-3,14β-dihydroxy-6'-methyl-6,7,2',3'-quinolinomorphinan, 17-allyl-6,7-didehydro-4,5α-epoxy-3,14β-dihydroxy-6'-methyl-6,7,2',3'-quinolinomorphinan, 17-cyclopropylmethyl-6,7-didehydro-4,5α-epoxy-14β-hydroxy-3-methoxy-6'-methyl-6,7,2',3'-quinolinomorphinan, 17-allyl-6,7-didehydro-4,5α-epoxy-14β-hydroxy-3-methoxy-6'-methyl-6,7,2',3'-quinolinomorphinan, 17-cyclopropylmethyl-6,7-didehydro-4,5α-epoxy-3,14β-dihydroxy-7'-methyl-6,7,2',3'-quinolinomorphinan, 17-allyl-6,7-didehydro-4,5α-epoxy-3,14β-dihydroxy-7'-methyl-6,7,2',3'-quinolinomorphinan, 17-cyclopropylmethyl-6,7-didehydro-4,5α-epoxy-14β-hydroxy-3-methoxy-7'-methyl-6,7,2',3'-quinolinomorphinan, 17-allyl-6,7-didehydro-4,5α-epoxy-14β-hydroxy-3-methoxy-7'-methyl-6,7,2',3'-quinolinomorphinan, 17-cyclopropylmethyl-6,7-didehydro-4,5α-epoxy-3,14β-dihydroxy-8'-methyl-6,7,2',3'-quinolinomorphinan, 17-allyl-6,7-didehydro-4,5α-epoxy-3,14β-dihydroxy-8'-methyl-6,7,2',3'-quinolinomorphinan, 17-cyclopropylmethyl-6,7-didehydro-4,5α-epoxy-14β-hydroxy-3-methoxy-8'-methyl-6,7,2',3'-quinolinomorphinan, 17-allyl-6,7-didehydro-4,5α-epoxy-14β-hydroxy-3-methoxy-8'-methyl-6,7,2',3'-quinolinomorphinan, 17-cyclopropylmethyl-6,7-didehydro-4,5α-epoxy-3,14β-dihydroxy-5'-bromo-6,7,2',3'-quinolinomorphinan, 17-allyl-6,7-didehydro-4,5α-epoxy-3,14β-dihydroxy-5'-bromo-6,7,2',3'-quinolinomorphinan, 17-cyclopropylmethyl-6,7-didehydro-4,5α-epoxy-14β-hydroxy-3-methoxy-5'-bromo-6,7,2',3'-quinolinomorphinan, 17-allyl-6,7-didehydro-4,5α-epoxy-14β-hydroxy-3-methoxy-5'-bromo-6,7,2',3'-quinolinomorphinan, 17-cyclopropylmethyl-6,7-didehydro-4,5α-epoxy-3,14β-dihydroxy-6'-bromo-6,7,2',3'-quinolinomorphinan, 17-allyl-6,7-didehydro-4,5α-epoxy-3,14β-dihydroxy-6'-bromo-6,7,2',3'-quinolinomorphinan, 17-cyclopropylmethyl-6,7-didehydro-4,5α-epoxy-14β-hydroxy-3-methoxy-6'-bromo-6,7,2',3'-quinolinomorphinan, 17-allyl-6,7-didehydro-4,5α-epoxy-14β-hydroxy-3-methoxy-6'-bromo-6,7,2',3'-quinolinomorphinan, 17-cyclopropylmethyl-6,7-didehydro-4,5α-epoxy-3,14β-dihydroxy-7'-bromo-6,7,2',3'-quinolinomorphinan, 17-allyl-6,7-didehydro-4,5α-epoxy-3,14β-dihydroxy-7'-bromo-6,7,2',3'-quinolinomorphinan, 17-cyclopropylmethyl-6,7-didehydro-4,5α-epoxy-14β-hydroxy-3-methoxy-7'-bromo-6,7,2',3'-quinolinomorphinan, 17-allyl-6,7-didehydro-4,5α-epoxy-14β-hydroxy-3-methoxy-7'-bromo-6,7,2',3'-quinolinomorphinan, 17-cyclopropylmethyl-6,7-didehydro-4,5α-epoxy-3,14β-dihydroxy-8'-bromo-6,7,2',3'-quinolinomorphinan, 17-allyl-6,7-didehydro-4,5α-epoxy-3,14β-dihydroxy-8'-bromo-6,7,2',3'-quinolinomorphinan, 17-cyclopropylmethyl-6,7-didehydro-4,5α-epoxy-14β-hydroxy-3-methoxy-8'-bromo-6,7,2',3'-quinolinomorphinan, 17-allyl-6,7-didehydro-4,5α-epoxy-14β-hydroxy-3-methoxy-8'-bromo-6,7,2',3'-quinolinomorphinan, 17-cyclopropylmethyl-6,7-didehydro-4,5α-epoxy-3,14β-dihydroxy-5'-methoxy-6,7,2',3'-quinolinomorphinan, 17-allyl-6,7-didehydro-4,5α-epoxy-3,14β-dihydroxy-5'-methoxy-6,7,2',3'-quinolinomorphinan, 17-cyclopropylmethyl-6,7-didehydro-4,5α-epoxy-14β-hydroxy-3-methoxy-5'-methoxy-6,7,2',3'-quinolinomorphinan, 17-allyl-6,7-didehydro-4,5α-epoxy-14β-hydroxy-3-methoxy-5'-methoxy-6,7,2',3'-quinolinomorphinan, 17-cyclopropylmethyl-6,7-didehydro-4,5α-epoxy-3,14β-dihydroxy-6'-methoxy-6,7,2',3'-quinolinomorphinan, 17-allyl-6,7-didehydro-4,5α-epoxy-3,14β-dihydroxy-6'-methoxy-6,7,2',3'-quinolinomorphinan, 17-cyclopropylmethyl-6,7-didehydro-4,5α-epoxy-14β-hydroxy-3-methoxy-6'-methoxy-6,7,2',3'-quinolinomorphinan, 17-allyl-6,7-didehydro-4,5α-epoxy-14β-hydroxy-3-methoxy-6'-methoxy-6,7,2',3'-quinolinomorphinan, 17-cyclopropylmethyl-6,7-didehydro-4,5α-epoxy-3,14β-dihydroxy-7'-methoxy-6,7,2',3'-quinolinomorphinan, 17-allyl-6,7-didehydro-4,5α-epoxy-3,14β-dihydroxy-7'-methoxy-6,7,2',3'-quinolinomorphinan, 17-cyclopropylmethyl-6,7-didehydro-4,5α-epoxy-14β-hydroxy-3-methoxy-7'-methoxy-6,7,2',3'-quinolinomorphinan, 17-allyl-6,7-didehydro-4,5α-epoxy-14β-hydroxy-3-methoxy-7'-methoxy-6,7,2',3'-quinolinomorphinan, 17-cyclopropylmethyl-6,7-didehydro-4,5α-epoxy-3,14β-dihydroxy-8'-methoxy-6,7,2',3'-quinolinomorphinan, 17-allyl-6,7-didehydro-4,5α-epoxy-3,14β-dihydroxy-8'-methoxy-6,7,2',3'-quinolinomorphinan, 17-cyclopropylmethyl-6,7-didehydro-4,5α-epoxy-14β-hydroxy-3-methoxy-8'-methoxy-6,7,2',3'-quinolinomorphinan, 17-allyl-6,7-didehydro-4,5α-epoxy-14β-hydroxy-3-methoxy-8'-methoxy-6,7,2',3'-quinolinomorphinan, 17-cyclopropylmethyl-6,7-didehydro-4,5α-epoxy-3,14β-dihydroxy-5'-nitro-6,7,2',3'-quinolinomorphinan, 17-allyl-6,7-didehydro-4,5α-epoxy-3,14β-dihydroxy-5'-nitro-6,7,2',3'-quinolinomorphinan, 17-cyclopropylmethyl-6,7-didehydro-4,5α-epoxy-14β-hydroxy-3-methoxy-5'-nitro-6,7,2',3'-quinolinomorphinan, 17-allyl-6,7-didehydro-4,5α-epoxy-14β-hydroxy-3-methoxy-5'-nitro-6,7,2',3'-quinolinomorphinan, 17-cyclopropylmethyl-6,7-didehydro-4,5α-epoxy-3,14β-dihydroxy-6'-nitro-6,7,2',3'-quinolinomorphinan, 17-allyl-6,7-didehydro-4,5α-epoxy-3,14β-dihydroxy-6'-nitro-6,7,2',3'-quinolinomorphinan, 17-cyclopropylmethyl-6,7-didehydro-4,5α-epoxy-14β-hydroxy-3-methoxy-6'-nitro-6,7,2',3'-quinolinomorphinan, 17-allyl-6,7-didehydro-4,5α-epoxy-14β-hydroxy-3-methoxy-6'-nitro-6,7,2',3'-quinolinomorphinan, 17-cyclopropylmethyl-6,7-didehydro-4,5α-epoxy-3,14β-dihydroxy-7'-nitro-6,7,2',3'-quinolinomorphinan, 17-allyl-6,7-didehydro-4,5α-epoxy-3,14β-dihydroxy-7'-nitro-6,7,2',3'-quinolinomorphinan, 17-cyclopropylmethyl-6,7-didehydro-4,5α-epoxy-14β-hydroxy-3-methoxy-7'-nitro-6,7,2',3'-quinolinomorphinan, 17-allyl-6,7-didehydro-4,5α-epoxy-14β-hydroxy-3-methoxy-7'-nitro-6,7,2',3'-quinolinomorphinan, 17-cyclopropylmethyl-6,7-didehydro-4,5α-epoxy-3,14β-dihydroxy-8'-nitro-6,7,2',3'-quinolinomorphinan, 17-allyl-6,7-didehydro-4,5α-epoxy-3,14β-dihydroxy-8'-nitro-6,7,2',3'-quinolinomorphinan, 17-cyclopropylmethyl-6,7-didehydro-4,5α-epoxy-14β-hydroxy-3-methoxy-8'-nitro-6,7,2',3'-quinolinomorphinan, 17-allyl-6,7-didehydro-4,5α-epoxy-14β-hydroxy-3-methoxy-8'-nitro-6,7,2',3'-quinolinomorphinan, 17-cyclopropylmethyl-6,7-didehydro-4,5α-epoxy-3,14β-dihydroxy-5'-methoxycarbonyl-6,7,2',3'-quinolinomorphinan, 17-allyl-6,7-didehydro-4,5α-epoxy-3,14β-dihydroxy-5'-methoxycarbonyl-6,7,2',3'-quinolinomorphinan, 17-cyclopropylmethyl-6,7-didehydro-4,5α-epoxy-14β-hydroxy-3-methoxy-5'-methoxycarbonyl-6,7,2',3'-quinolinomorphinan, 17-allyl-6,7-didehydro-4,5α-epoxy-14β-hydroxy-3-methoxy-5'-methoxycarbonyl-6,7,2',3'-quinolinomorphinan, 17-cyclopropylmethyl-6,7-didehydro-4,5α-epoxy-3,14β-dihydroxy-6'-methoxycarbonyl-6,7,2',3'-quinolinomorphinan, 17-allyl-6,7-didehydro-4,5α-epoxy-3,14β-dihydroxy-6'-methoxycarbonyl-6,7,2',3'-quinolinomorphinan, 17-cyclopropylmethyl-6,7-didehydro-4,5α-epoxy-14β-hydroxy-3-methoxy-6'-methoxycarbonyl-6,7,2',3'-quinolinomorphinan, 17-allyl-6,7-didehydro-4,5α-epoxy-14β-hydroxy-3-methoxy-6'-methoxycarbonyl-6,7,2',3'-quinolinomorphinan, 17-cyclopropylmethyl-6,7-didehydro-4,5α-epoxy-3,14β-dihydroxy-7'-methoxycarbonyl-6,7,2',3'-quinolinomorphinan, 17-allyl-6,7-didehydro-4,5α-epoxy-3,14β-dihydroxy-7'-methoxycarbonyl-6,7,2',3'-quinolinomorphinan, 17-cyclopropylmethyl-6,7-didehydro-4,5α-epoxy-14β-hydroxy-3-methoxy-7'-methoxycarbonyl-6,7,2',3'-quinolinomorphinan, 17-allyl-6,7-didehydro-4,5α-epoxy-14β-hydroxy-3-methoxy-7'-methoxycarbonyl-6,7,2',3'-quinolinomorphinan, 17-cyclopropylmethyl-6,7-didehydro-4,5α-epoxy-3,14β-dihydroxy-8'-methoxycarbonyl-6,7,2',3'-quinolinomorphinan, 17-allyl-6,7-didehydro-4,5α-epoxy-3,14β-dihydroxy-8'-methoxycarbonyl-6,7,2',3'-quinolinomorphinan, 17-cyclopropylmethyl-6,7-didehydro-4,5α-epoxy-14β-hydroxy-3-methoxy-8'-methoxycarbonyl-6,7,2',3'-quinolinomorphinan and 17-allyl-6,7-didehydro-4,5α-epoxy-14β-hydroxy-3-methoxy-8'-methoxycarbonyl-6,7,2',3'-quinolinomorphinan.

However, the above description does not intend to limit the present invention.

The compounds of the formula (I) which are used in the present invention may be produced by known methods (P. S. Portoghese, J. Med. Chem. Vol. 31, No. 2, 281, 1988; P. S.

Portoghese, J. Med. Chem. Vol. 34, No. 4, 1292, 1991; P. S. Portoghese, J. Med. Chem. Vol. 34, No. 5, 1715, 1991). In these known methods, the compounds of the formula (I) are produced according to the following reaction equation.

acid salt, ethanesulfonic acid salt, benzenesulfonic acid salt, p-toluenesulfonic acid salt and camphorsulfonic acid salt. Among these, hydrochloric acid salt, hydrobromic acid salt, phosphoric acid salt, tartaric acid salt, methanesulfonic acid

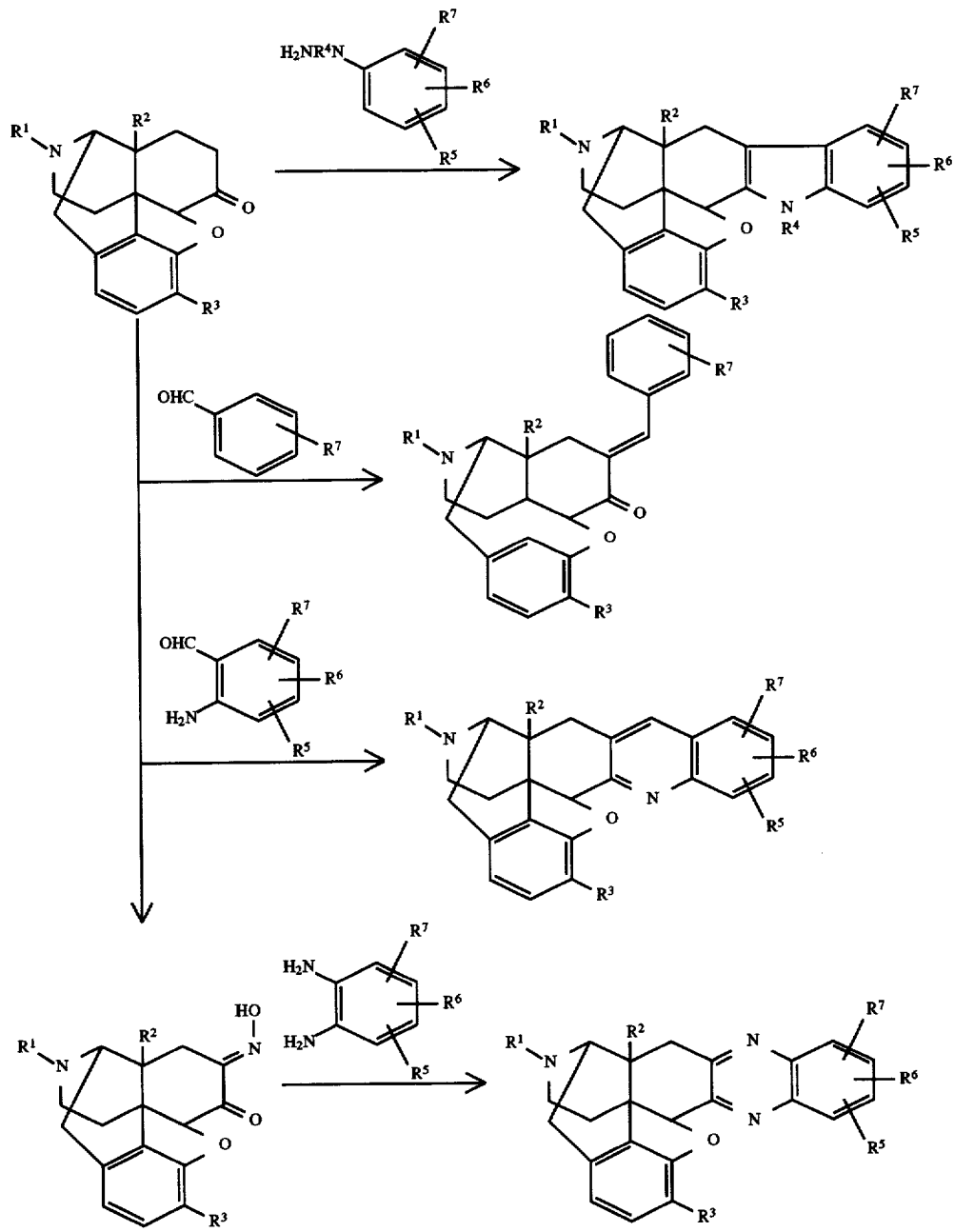

Preferred examples of the pharmaceutically acceptable salts which may be employed in the present invention include inorganic acids such as hydrochloric acid salt, sulfuric acid salt, nitric acid salt, hydrobromic acid salt, hydroiodic acid salt and phosphoric acid salt; organic carboxylic acid salts such as acetic acid salt, oxalic acid salt, mandelic acid salt, benzoic acid salt, phthalic acid salt, glutaric acid salt, fumaric acid salt, tartaric acid salt, malic acid salt, lactic acid salt, succinic acid salt and maleic acid salt; and organic sulfonic acid salts such as methanesulfonic salt and the like are preferred, although the salts are not restricted thereto.

The antitussive according to the present invention may be clinically applied in the form of a free base or a salt thereof. Alternatively, the active compound may be admixed with one or more appropriate vehicles such as stabilizers, buffer agents, diluents, isotonic agents, antiseptic agents and the like. The antitussive may be formulated in the form of injection solutions; formulations for oral administration such as tablets, capsules, granules, powders, syrups and the like; formulations for colorectal administration such as suppositories; and formulations for topical administration such as ointments, creams and patches. Among these, injection solutions and oral formulations are preferred.

The antitussive according to the present invention may preferably contain the above-described effective ingredient in an amount of 0.0001–90% by weight. Although the dose of administration may be appropriately selected depending on the object of administration, administration route and symptoms of the patient, in case of injection solution, the dose may be 1 μg–0.1 g/day and in case of oral administration, the dose may be 10 μg–1 g/day. The antitussive may be administered in one time per day or in several times per day.

The present invention will now be described by way of examples thereof. However, the examples should not be interpreted as limiting the present invention.

PRODUCTION EXAMPLE 1

17-cyclopropylmethyl-6,7-didehydro-4,5α-epoxy-3, 14β-dihydroxy-[6',7'-b]-pyrido-6,7,2',3'-indolomorphinan 5

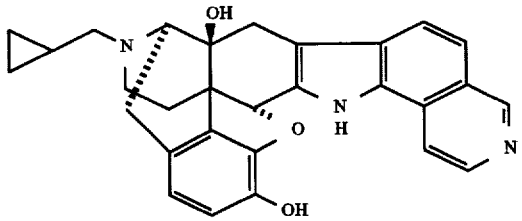

A mixture of 1.34 g of naltrexone hydrochloric acid salt, 0.64 g of 5-hydrazinoisoquinoline, 0.71 ml of methanesulfonic acid and 21 ml of ethanol was heated to reflux to obtain a compound containing indole moiety. The resulting compound was purified by silica gel column chromatography (chloroform saturated with ammonia/methanol=20/1, 15/1) to obtain a free base, and the obtained free base was converted to a salt in chloroform/methanol to obtain 1.53 g of methanesulfonic acid salt of the captioned compound (yield: 64%).

mp>280° C. (decomposed)

NMR (400 MHz, DMSO-d6) δ 0.42–0.80 (4H, m), 1.07–1.18 (1H, m), 1.90 (1H, brd, J=11.7 Hz), 2.36 (6H, s), 2.64–2.83 (2H, m), 2.67 (1H, d, J=16.1 Hz), 2.95–3.05(1H, m), 3.13–3.24 (1H, m), 3.19 (1H, d, J=16.1 Hz), 3.29 (1H, dd, J=6.8, 20.0 Hz), 3.30–3.53 (2H, m), 3.50 (1H, d, J=20.0 Hz), 4.16 (1H, d, J=6.8 Hz), 5.92 (1H, s), 6.47 (1H, brs), 6.64 (1H, d, J=8.3 Hz), 6.67 (1H, d, J=8.3 Hz), 7.97 (1H, d, J=8.8 Hz), 8.00 (1H, d, J=8.8 Hz), 8.75 (1H, d, J=6.8 Hz), 8.83 (1H, d, J=6.8 Hz), 9.00 (1H, brs), 9.32 (1H, brs), 9.74 (1H, s), 13.37 (1H, s).

IR(KBr) ν 3400, 1638, 1388, 1330, 1199 ,1116, 1052, 785 cm$^{-1}$

Mass (FAB) m/z 466 ((M+H)$^{+}$).

Elementary Analysis: $C_{29}H_{27}N_3O_3 \cdot 2.1CH_3SO_3H \cdot 0.4H_2O$ Calcd.: C, 55.37; H, 5.41; N, 6.23; S, 9.98 Found: C, 55.54; H, 5.71; N, 6.32; S, 9.71

PRODUCTION EXAMPLE 2

17-cyclopropylmethyl-6,7-didehydro-4,5α-epoxy-3, 14β-dihydroxy-6',7'-cyclohexeno-6,7,2',3'-indolomorphinan 2

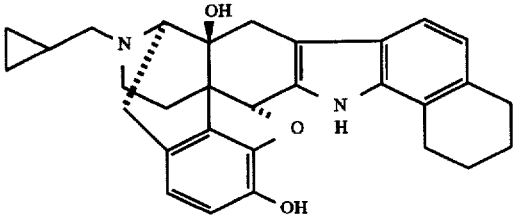

The same procedure as in Production Example 1 was repeated except that 1-hydrazino-5,6,7,8-tetrahydronaphthalene was used in place of 5-hydrazinoisoquinoline to obtain methanesulfonic acid salt of the captioned compound (yield: 32%).

mp>235° C. (decomposed)

NMR (500 MHz, CDCl3, data for free base) δ 0.13–0.20 (2H, m), 0.53–0.61 (2H, m), 0.85–0.93 (1H, m), 1.77–1.89 (5H, m), 2.30 (1H, dt, J=3.5, 12.5 Hz), 2.38–2.47 (2H, m), 2.46 (1H, dd, J=6.4, 12.5 Hz), 2.60 (1H, dd, J=1.1, 15.7 Hz), 2.67–2.86 (6H, m), 2.86 (1H, d, J=15.6 Hz), 3.12 (1H, d, J=18.3 Hz), 3.36 (1H,d, J=6.6Hz), 5.04 (2H, brs), 5.71 (1H, s), 6.53 (1H, d, J=8.1 Hz), 6.60 (1H, d, J=8.1 Hz), 6.74 (1H, d, J=8.1 Hz), 7.14 (1H, d, J=8.1 Hz), 8.06 (1H, s).

IR(KBr) ν 3400, 1510, 1460, 1207, 1048 cm$^{-1}$

Mass (EI) m/z 468 (M$^{+}$).

Elementary Analysis: $C_{30}H_{32}N_2O_3 \cdot CH_3SO_3H \cdot 0.6H_2O$ Calcd.: C, 64.70; H, 6.51; N, 4.87; S, 5.57 Found: C, 64.33; H, 6.54; N, 4.95; S, 5.83

PRODUCTION EXAMPLE 3

17-cyclopropylmethyl-6,7-didehydro-4,5α-epoxy-14β-hydroxy-3-methoxy-[6',7'-b]-pyrido-6,7,2',3'-indolomorphinan 6

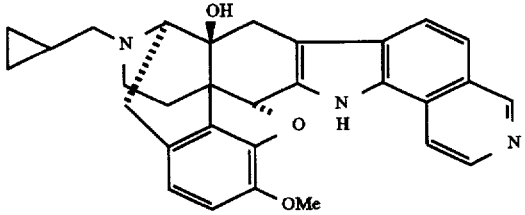

The same procedure as in Production Example 1 was repeated except that naltrexone-3-methyl ether was used in place of naltrexone hydrochloric acid salt to obtain methanesulfonic acid salt of the captioned compound (yield: 83%).

mp: 245°–255° C. (decomposed)

NMR (400 MHz, DMSO-d6) δ 0.44–0.56 (2H, m), 0.66 (1H, m), 0.76 (1H, m), 1.14 (1H, m), 1.92 (1H, d, J=10.7 Hz), 2.35 (5.1H, s), 2.64–2.80 (3H, m), 3.02 (1H, m), 3.15–3.25 (2H, m), 3.4–3.6 (3H, m), 3.69 (3H, s), 4.18 (1H, d, J=6.4 Hz), 5.99 (1H, s), 6.78 (1H, d, J=8.3 Hz), 6.85 (1H, d, J=8.3 Hz), 7.98 (1H, d, J=8.8 Hz), 8.01 (1H, d, J=8.8 Hz), 8.76 (1H, d, J=6.8 Hz), 8.83 (1H, d, J=6.8 Hz), 9.76 (1H, s)

IR(KBr) ν 3400, 1638, 1510, 1199, 1052, 897 cm$^{-1}$

Mass (FAB) m/z 480 ((M+H)$^{+}$).

Elementary Analysis: $C_{30}H_{29}N_3O_3 \cdot 1.7CH_3SO_3H \cdot 2.3H_2O$
Calcd.: C, 55.63; H, 5.95; N, 6.14; S, 7.97 Found: C, 55.86; H, 5.79; N, 5.92; S, 7.97

PRODUCTION EXAMPLE 4

17-cyclopropylmethyl-6,7-didehydro-4,5α-epoxy-14β-hydroxy-3-methoxy-6,7,2',3'-indolomorphinan 7

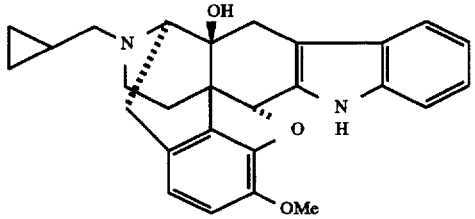

The same procedure as in Production Example 1 was repeated except that naltrexone-3-methyl ether was used in place of naltrexone hydrochloric acid salt, and phenylhydrazine was used in place of 5-hydrazinoquinoline to obtain methanesulfonic acid of the captioned compound (yield: 76%).

mp>300° C.

NMR (50 MHz, DMSO-d6) δ 0.42–0.55 (2H, m), 0.63 (1H, m), 0.74 (1H, m), 1.11 (1H, m), 1.84 (1H, d, J=13.4 Hz), 2.31 (3H, s), 2.50–2.73 (3H, m), 2.94–3.00 (2H, m), 3.13 (1H, m), 3.3–3.6 (3H, m), 3.68 (3H, s), 4.11 (1H, d, J=6.7 Hz), 5.75 (1H, s), 6.73 (1H, d, J=8.5 Hz), 6.81 (1H, d, J=8.3 Hz), 6.97 (1H, t, J=7.9 Hz), 7.11 (1H, t, J=7.3 Hz), 7.35 (2H, d, J=9.2 Hz)

IR(KBr) ν 3400, 1509, 1458, 1210, 1050 cm$^{-1}$

Mass (FAB) m/z 429 ((M+H)$^+$).

Elementary Analysis: $C_{27}H_{28}N_2O_3 \cdot CH_3SO_3H \cdot 0.2H_2O$
Calcd.: C, 63.66; H, 6.18; N, 5.30; S, 6.07 Found: C, 63.65; H, 6.20; N, 5.20; S, 5.92

EXAMPLES

Test Animals

SD male rats (body weight: 250–350 g) were used under non-anesthesic condition.

Measurement of Respiration and Coughs

Respiration and cough were measured by plestimography. The body plestimograph used has a plastic cylinder having a diameter of 7.5 cm and a length of 15 cm, and consists of a cylindrical part in which the body of the rat is inserted and a cap part which covers the head. In the upper portion of the cylinder, a vent was formed so as to connect a respiration flow meter. To tightly close the cylinder, a collar made of rubber or celluloid was put on the neck of the rat. In the cap part, an inlet for introducing capsaicin and a ventilating hole were formed. The respiration of the rats was measured by measuring the movement of the thorax due to the respiration in terms of the change in the inner volume of the cylinder by the respiration flow meter. Since the thorax vigorously moves when a cough is induced, a large change in the inner volume of the cylinder is temporarily caused. This large change is distinguished from the normal respiration and measured by the respiration flow meter. The number of this large change was measured, which is defined as the number of cough.

Example 1

Induction of Cough

Capsaicin (30 μM) was converted to mist by ultrasonic nebulizer and the mist was sent by an artificial respirator into the cap covering the head of the rat through a silicone tube, thereby inducing cough. Capsaicin was transferred by the artificial respirator for inhalation at a dose of 20 ml/time and at a rate of 30 times/min.

Experimental Schedule

The rats were made to inhale capsaicin for 5 minutes at 15 minutes before the administration of the test compound. Induction of cough was confirmed during the inhalation of capsaicin. The rats were made to inhale capsaicin for 5 minutes at 15, 60 and 120 minutes after administration of the compound, and the number of induced cough was measured during this period. The antitussive effect was evaluated in terms of the suppression rate, that is, the ratio of the number of cough after administration of the test compound to the number of cough before administration of the compound. The measured suppression rates were compared using Mann Whiteny U-test. If there is a difference at significant level (P<0.05), the difference was evaluated as significant. Capsaicin was dissolved in 10% ethanol and 10% Tween 80 and diluted with saline. The test compound was dissolved in saline. In any case, the test compound was intraperitoneally administered.

Effects by Compound 1 (naltrindole: NTI) on Cough Reflection

Figure 2:
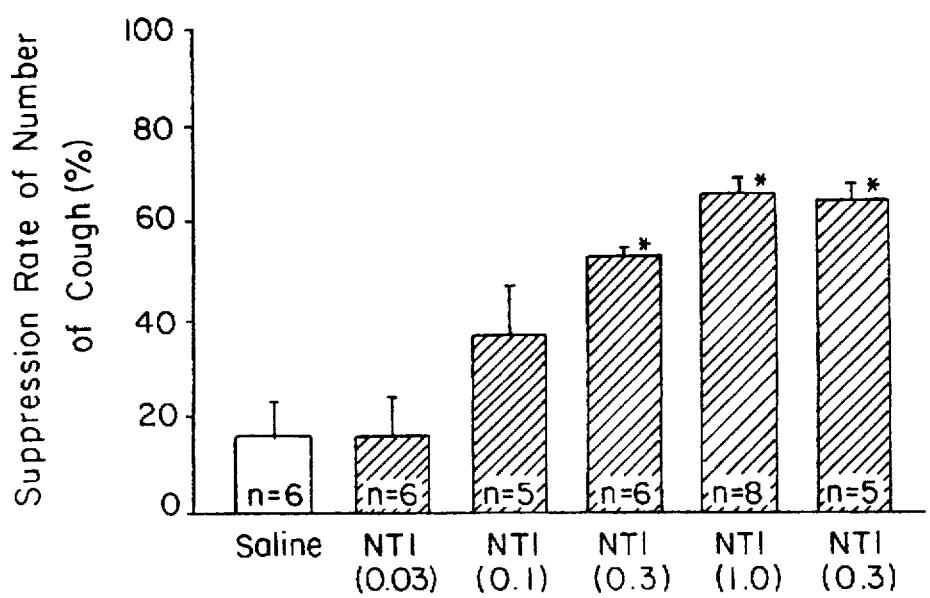
FIG. 2 shows the suppression rate of number of cough after 15 minutes from the administration of Compound 1.

By inhalation of capsaicin, stable cough at a rate of 22.5±1.2 times/5 minutes was induced. This cough was not influenced by administration of saline at all. By administration of Compound 1 (NTI: 1 mg/kg), a significant antitussive effect was observed. The peak of the antitussive effect was 15 minutes after administration of the compound and then the antitussive effect was reduced with time. However, a significant antitussive effect was observed even 120 minutes after the administration of the test compound when compared with the results obtained for the group to which saline was administered (FIG. 1). The cough-suppression rate by Compound 1 at 15 minutes after administration at varying dosage is shown in FIG. 2. Compound 1 showed dose-dependent antitussive effect within the dose range of 0.03 mg/kg to 1 mg/kg. The antitussive effect by Compound 1 (1 mg/kg) was substantially identical to that by morphine (0.3 mg/kg).

In FIG. 1, each value indicates mean±S.E. of at least 5 cases of the suppression rate of the number of cough. The symbol "○" indicates the results for the group to which saline was administered, and the symbol "●" indicates the results for the group to which Compound 1 (1 mg/kg, i.p.) was administered. The symbol "★" indicates the cases where P<0.05 with respect to the results for the saline-administered group.

In FIG. 2, each value indicates mean±S.E. of at least 5 cases of the suppression rate of the number of cough. "NTI" indicates the results of Compound 1 and "MOR" indicates the results of morphine. The values in parentheses indicate administration dose (mg/kg, i.p.). The symbol "★" indicates the same meaning as in FIG. 1.

Example 2

By the same method as in Example 1, the effect by Compound 3 (benzylidenenaltrexone: BNTX) which is a δ1-antagonist was examined. The results are shown in FIG. 3.

In FIG. 3, each value indicates mean±S.E. of at least 5 cases of the suppression rate of the number of tussis. The symbol "●" indicates the results of the saline-administered group and the symbol "○" indicates the results of the Compound 3-administered group (3 mg/kg, i.p.). The symbol "☆" indicates the same meaning as in FIG. 1.

Example 3

Induction of Cough

Capsaicin (60 μM) was converted to mist by ultrasonic nebulizer and the mist was sent by an artificial respirator into the cap covering the head of the rat through a silicone tube, thereby inducing cough. Capsaicin was transferred by the artificial respirator for inhalation at a dose of 10 ml/time and at a rate of 70 times/min.

Experimental Schedule

The rats were made to inhale capsaicin for 5 minutes at 270 minutes before the administration of the test compound. Induction of cough was confirmed during the inhalation of capsaicin. The rats were made to inhale capsaicin for 5 minutes at 30 minutes after administration of the test compound, and the number of induced cough during this period was measured. The antitussive effect was evaluated in terms of the suppression rate, that is, the ratio of the number of cough after administration of the test compound to the number of cough before administration of the test compound. Capsaicin was dissolved in saline. The test compounds were dissolved in aqueous 10% DMSO solution. In any case, the test compounds were intraperitoneally administered. The effectiveness of each of the test compounds is shown in terms of $ED_{50}$ value which means the dose at which the number of cough is suppressed to half.

| Test Compound | $ED_{50}$ (μg/kg) |
|---|---|
| 2 | 39.5 |
| 4 | 984 |
| 5 | 79.7 |
| 6 | 41.3 |
| 7 | 63.9 |

We claim:

1. A method for suppressing cough in a subject suffering from coughing comprising administering to a subject suffering from coughing an amount effective for decreasing the frequency of coughing of an antitussive comprising as the antitussive-effective ingredient a δ-opioid antagonist, or a pharmaceutically acceptable salt thereof.

2. A method for suppressing cough in a subject suffering from coughing comprising administering to a subject suffering from coughing an amount effective for decreasing the frequency of coughing of a composition comprising a δ-opioid antagonist represented by the formula (I):

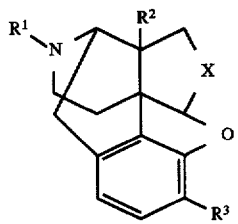

(I)

wherein $R^1$ represents $C_1$–$C_5$ alkyl, $C_4$–$C_7$ cycloalkylalkyl, $C_5$–$C_7$ cycloalkenylalkyl, $C_6$–$C_{12}$ aryl, $C_7$–$C_{13}$ aralkyl, $C_4$–$C_7$ alkenyl, allyl, $C_1$–$C_5$ furan-2-ylalkyl or $C_1$–$C_5$ thiophene-2-ylalkyl; $R^2$ represents hydrogen, hydroxy, $C_1$–$C_5$ alkanoyloxy, $C_1$–$C_5$ alkoxy, $C_7$–$C_{13}$ arylcarbonyloxy or $C_7$–$C_{13}$ aralkyloxy; $R^3$ represents hydrogen, hydroxy, $C_1$–$C_5$ alkanoyloxy, $C_1$–$C_5$ alkoxy, $C_7$–$C_{13}$ arylcarbonyloxy or $C_7$–$C_{13}$ aralkyloxy; x represents

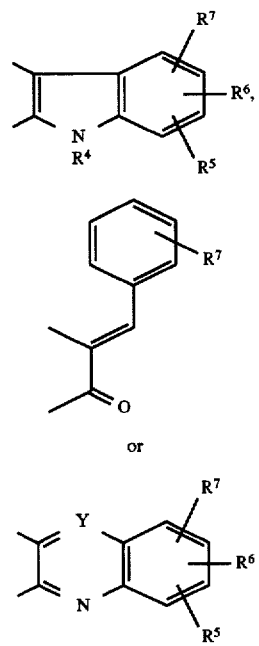

wherein $R^4$ represents hydrogen, $C_1$–$C_5$ alkyl or $C_7$–$C_{13}$ aralkyl; $R^5$, $R^6$ and $R^7$ independently represent hydrogen, fluorine, chlorine, bromine, nitro, $C_1$–$C_5$ alkyl, $C_1$–$C_5$ alkoxy, isothiocyanato, iodine, trifluoromethyl, trifluoromethoxy, cyano, phenyl, $C_1$–$C_3$ hydroxyalkyl, $SR^8$, $SOR^8$, $SO_2R^8$, $(CH_2)_mCO_2R^8$, wherein m represents an integer of 0–3. $R^8$ represents $C_1$–$C_5$ alkyl, $SO_2NR^9R^{10}$, $CONR^9R^{10}$, $(CH_2)_nNR^9R^{10}$, wherein n represents an integer of 0–3. $R^9$ and $R^{10}$ independently represent hydrogen, $C_1$–$C_5$ alkyl or $C_4$–$C_6$ cycloalkylalkyl, or $R^7$ is as defined above and binds $R^5$ and $R^6$ to form (1) $C_3$–$C_6$ alkylene, with the proviso that one or more of the hydrogen atoms in the alkylene moiety may be substituted with $R^{11}$, wherein $R^{11}$ represents $C_1$–$C_5$ alkyl, $C_1$–$C_5$ alkoxy, $C_1$–$C_5$ alkanoyl, $C_1$–$C_5$ hydroxyalkyl, $SR^8$, $SOR^8$, $SO_2R^8$, $(CH_2)_mCO_2R^8$, $SO_2NR^9R^{10}$, $CONR^9R^{10}$, $(CH_2)_nNR^9R^{10}$, wherein m, n, $R^8$, $R^9$ and $R^{10}$ are defined as above, said alkylene being bound to adjacent carbon atoms in the benzene ring to form a ring, or (2) —S=T—U=V—, wherein S, T, U and V represent nitrogen or CH, the CH hydrogen may be substituted with $R^{12}$, wherein $R^{12}$ represents fluorine, chlorine, bromine, nitro, $C_1$–$C_5$ alkyl, $C_1$–$C_5$ alkoxy, isothiocyanato, iodine, trifluoromethyl, trifluoromethoxy, cyano, phenyl, $C_1$–$C_3$ hydroxyalkyl, $SR^8$, $SOR^8$, $SO_2R^8$, $(CH_2)_mCO_2R^8$, $SO_2NR^9R^{10}$, $CONR^9R^{10}$, or $(CH_2)_nNR^9R^{10}$, wherein m, n, $R^8$, $R^9$ and $R^{10}$ are defined as above, said —S=T—U=V— being bound to adjacent carbon atoms in the benzene ring to form a ring and Y is N or CH; the formula (I) including (+) isomers, (−) isomers and racemates;

and a pharmaceutically acceptable carrier.

3. The method according to claim 2, wherein $R^5$, $R^6$ and $R^7$ are not simultaneously hydrogen.

4. The method according to claim 2, wherein x is

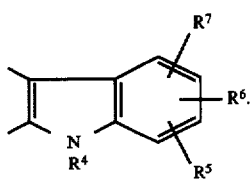

5. The method according to claim 2, wherein x is

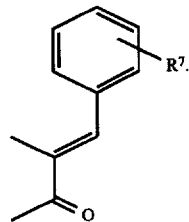

6. The method according to claim 2, wherein X is

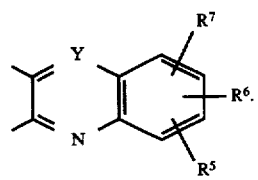

7. The method according to claim 4, wherein $R^5$, $R^6$ and $R^7$ are not simultaneously hydrogen.

8. The method according to claim 5, wherein $R^5$, $R^6$ and $R^7$ are not simultaneously hydrogen.

9. The method according to claim 6, wherein $R^5$, $R^6$ and $R^7$ are not simultaneously hydrogen.

10. A method for suppressing cough in a subject suffering from coughing comprising administering to a subject suffering from coughing an amount effective for decreasing the frequency of coughing of a composition comprising a δ-opioid antagonist represented by the formula (I):

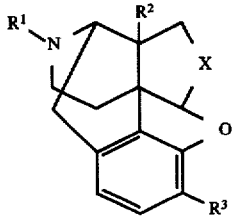

(I)

wherein $R^1$ represents $C_1$–$C_5$ alkyl, $C_4$–$C_7$ cycloalkylalkyl, $C_5$–$C_7$ cycloalkenylalkyl, $C_6$–$C_{12}$ aryl, $C_7$–$C_{13}$ aralkyl, $C_4$–$C_7$ alkenyl, allyl, $C_1$–$C_5$ furan-2-ylalkyl or $C_1$–$C_5$ thiophene-2-ylalkyl; $R^2$ represents hydrogen, hydroxy, $C_1$–$C_5$ alkanoyloxy, $C_1$–$C_5$ alkoxy, $C_7$–$C_{13}$ arylcarbonyloxy or $C_7$–$C_{13}$ aralkyloxy; $R^3$ represents hydrogen, hydroxy, $C_1$–$C_5$ alkanoyloxy, $C_1$–$C_5$ alkoxy, $C_7$–$C_{13}$ arylcarbonyloxy or $C_7$–$C_{13}$ aralkyloxy; x represents

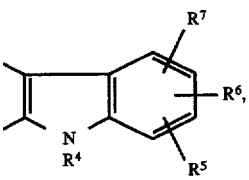

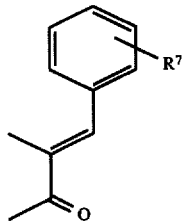

or

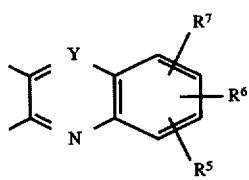

wherein $R^4$ represents hydrogen, $C_1$–$C_5$ alkyl or $C_7$–$C_{13}$ aralkyl; $R^5$, $R^6$ and $R^7$ independently represent hydrogen, fluorine, chlorine, bromine, nitro, $C_1$–$C_5$ alkyl, $C_1$–$C_5$ alkoxy, isothiocyanato, iodine, trifluoromethyl, trifluoromethoxy, cyano, phenyl, $C_1$–$C_3$ hydroxyalkyl, $SR^8$, $SOR^8$, $SO_2R^8$, $(CH_2)_mCO_2R^8$, wherein m represents an integer of 0–3, $R^8$ represents $C_1$–$C_5$ alkyl, $SO_2NR^9R^{10}$, $CONR^9R^{10}$, $(CH_2)_nNR^9R^{10}$, wherein n represents an integer of 0–3, $R^9$ and $R^{10}$ independently represent hydrogen, $C_1$–$C_5$ alkyl or $C_4$–$C_6$ cycloalkylalkyl, or $R^7$ is as defined above and binds $R^5$ and $R^6$ to form (1) $C_3$–$C_6$ alkylene, wherein one or more of the hydrogen atoms in the alkylene moiety may be substituted with $R^{11}$, wherein $R^{11}$ represents $C_1$–$C_5$ alkyl, $C_1$–$C_5$ alkoxy, $C_1$–$C_5$ alkanoyl, $C_1$–$C_5$ hydroxyalkyl, $SR^8$, $SOR^8$, $SO_2R^8$, $(CH_2)_mCO_2R^8$, $SO_2NR^9R^{10}$, $CONR^9R^{10}$, $(CH_2)_nNR^9R^{10}$, wherein m, n, $R^8$, $R^9$ and $R^{10}$ are defined as above, said alkylene being bound to adjacent carbon atoms in the benzene ring to form a ring, or (2) —S═T—U═V—, wherein S, T, U and V represent nitrogen or CH, the CH hydrogen may be substituted with $R^{12}$, wherein $R^{12}$ represents fluorine, chlorine, bromine, nitro, $C_1$–$C_5$ alkyl, $C_1$–$C_5$ alkoxy, isothiocyanato, iodine, trifluoromethyl, trifluoromethoxy, cyano, phenyl, $C_1$–$C_3$ hydroxyalkyl, $SR^8$, $SOR^8$, $SO_2R^8$, $(CH_2)_mCO_2R^8$, $SO_2NR^9R^{10}$, $CONR^9R^{10}$, or $(CH_2)_nNR^9R^{10}$, wherein m, n, $R^8$, $R^9$ and $R^{10}$ are defined as above, said —S═T—U═V— being bound to adjacent carbon atoms in the benzene ring to form a ring and Y is N or CH; the formula (I) including (+) isomers, (−) isomers and racemates;

and a pharmaceutically acceptable carrier;

wherein said δ-opioid antagonist is present in an amount effective for suppressing cough.

11. The method according to claim 10, wherein $R^5$, $R^6$ and $R^7$ are not simultaneously hydrogen.

* * * * *